(12) United States Patent
Stone et al.

(10) Patent No.: US 8,920,414 B2
(45) Date of Patent: Dec. 30, 2014

(54) TUNED RF ENERGY AND ELECTRICAL TISSUE CHARACTERIZATION FOR SELECTIVE TREATMENT OF TARGET TISSUES

(75) Inventors: Corbett W. Stone, San Diego, CA (US); Michael F. Hoey, Shoreview, MN (US); Tom A. Steinke, San Diego, CA (US); Raphael M. Michel, San Diego, CA (US); Arthur G. Blanck, Ramona, CA (US); Marlene Kay Truesdale, Monument, CO (US); Bret Herscher, Cupertino, CA (US)

(73) Assignee: Vessix Vascular, Inc., Laguna Hills, CA (US)

( * ) Notice: Subject to any disclaimer, the term of this patent is extended or adjusted under 35 U.S.C. 154(b) by 1958 days.

(21) Appl. No.: 11/975,651

(22) Filed: Oct. 18, 2007

(65) Prior Publication Data
US 2008/0125772 A1  May 29, 2008

Related U.S. Application Data

(60) Provisional application No. 60/921,973, filed on Apr. 4, 2007, provisional application No. 60/852,787, filed on Oct. 18, 2006.

(51) Int. Cl.
*A61B 18/18* (2006.01)

(52) U.S. Cl.
USPC ............... 606/41; 606/42; 600/381; 600/372; 600/373; 600/547

(58) Field of Classification Search
USPC .......... 606/32–35, 41–50; 600/372, 373, 381, 600/547
See application file for complete search history.

(56) References Cited

U.S. PATENT DOCUMENTS

| 1,167,014 | A | 1/1916 | O'Brien |
| 2,505,358 | A | 4/1950 | Gusberg et al. |
| 2,701,559 | A | 2/1955 | Cooper |

(Continued)

FOREIGN PATENT DOCUMENTS

| CA | 2384866 A1 | 5/2001 |
| CN | 101583323 A | 11/2009 |

(Continued)

OTHER PUBLICATIONS

Brown et al., "Radiofrequencey capacitivie heaters: the effect of coupling medium resistivity on power absorption along a mouse leg," Phys. Med. Biol., 1993, 38:1-12, abstract.

(Continued)

*Primary Examiner* — Michael Peffley
*Assistant Examiner* — Khadijeh Vahdat
(74) *Attorney, Agent, or Firm* — Seager, Tufte & Wickhem, LLC

(57) ABSTRACT

A catheter and catheter system can use energy tailored for remodeling and/or removal of target material along a body lumen, often of atherosclerotic material of a blood vessel of a patient. An elongate flexible catheter body with a radially expandable structure may have a plurality of electrodes or other electrosurgical energy delivery surfaces to radially engage atherosclerotic material when the structure expands. An atherosclerotic material detector system may measure and/or characterize the atherosclerotic material and its location, optionally using impedance monitoring.

27 Claims, 62 Drawing Sheets
(24 of 62 Drawing Sheet(s) Filed in Color)

(56) References Cited

U.S. PATENT DOCUMENTS

| | | |
|---|---|---|
| 3,108,593 A | 10/1963 | Glassman |
| 3,108,594 A | 10/1963 | Glassman |
| 3,540,431 A | 11/1970 | Mobin-Uddin |
| 3,952,747 A | 4/1976 | Kimmell, Jr. |
| 3,996,938 A | 12/1976 | Clark, III |
| 4,046,150 A | 9/1977 | Schwartz et al. |
| 4,290,427 A | 9/1981 | Chin |
| 4,587,975 A | 5/1986 | Salo et al. |
| 4,682,596 A | 7/1987 | Bales et al. |
| 4,709,698 A | 12/1987 | Johnston et al. |
| 4,770,653 A | 9/1988 | Shturman |
| 4,785,806 A | 11/1988 | Deckelbaum |
| 4,799,479 A | 1/1989 | Spears |
| 4,862,886 A | 9/1989 | Clarke et al. |
| 4,955,377 A | 9/1990 | Lennox et al. |
| 4,976,711 A | 12/1990 | Parins et al. |
| 5,053,033 A | 10/1991 | Clarke |
| 5,071,424 A | 12/1991 | Reger |
| 5,074,871 A | 12/1991 | Groshong |
| 5,098,429 A | 3/1992 | Sterzer |
| 5,098,431 A | 3/1992 | Rydell |
| 5,102,402 A | 4/1992 | Dror et al. |
| RE33,925 E | 5/1992 | Bales et al. |
| 5,109,859 A | 5/1992 | Jenkins |
| 5,129,396 A | 7/1992 | Rosen et al. |
| 5,156,151 A | 10/1992 | Imran |
| 5,156,610 A | 10/1992 | Reger |
| 5,158,564 A | 10/1992 | Schnepp-Pesch et al. |
| 5,178,620 A | 1/1993 | Eggers et al. |
| 5,178,625 A | 1/1993 | Groshong |
| 5,190,540 A | 3/1993 | Lee |
| 5,191,883 A | 3/1993 | Lennox et al. |
| 5,211,651 A | 5/1993 | Reger et al. |
| 5,254,098 A | 10/1993 | Ulrich et al. |
| 5,263,493 A | 11/1993 | Avitall |
| 5,277,201 A | 1/1994 | Stern |
| 5,282,484 A | 2/1994 | Reger |
| 5,286,254 A | 2/1994 | Shapland et al. |
| 5,304,171 A | 4/1994 | Gregory et al. |
| 5,304,173 A | 4/1994 | Kittrell et al. |
| 5,322,064 A | 6/1994 | Lundquist |
| 5,330,518 A | 7/1994 | Neilson et al. |
| 5,345,936 A | 9/1994 | Pomeranz et al. |
| 5,383,917 A | 1/1995 | Desai et al. |
| 5,409,000 A | 4/1995 | Imran |
| 5,419,767 A | 5/1995 | Eggers et al. |
| 5,453,091 A | 9/1995 | Taylor et al. |
| 5,454,809 A | 10/1995 | Janssen |
| 5,474,530 A | 12/1995 | Passafaro et al. |
| 5,496,311 A | 3/1996 | Abele et al. |
| 5,496,312 A | 3/1996 | Klicek |
| 5,498,261 A | 3/1996 | Strul |
| 5,540,681 A | 7/1996 | Strul |
| 5,545,161 A | 8/1996 | Imran |
| 5,562,100 A | 10/1996 | Kittrell |
| 5,571,122 A | 11/1996 | Kelly et al. |
| 5,571,151 A | 11/1996 | Gregory |
| 5,573,531 A | 11/1996 | Gregory |
| 5,573,533 A | 11/1996 | Strul |
| 5,599,346 A | 2/1997 | Edwards et al. |
| 5,609,606 A | 3/1997 | O'Boyle |
| 5,626,576 A | 5/1997 | Janssen |
| 5,643,297 A | 7/1997 | Nordgren et al. |
| 5,647,847 A | 7/1997 | Lafontaine et al. |
| 5,649,923 A | 7/1997 | Gregory et al. |
| 5,662,671 A | 9/1997 | Barbut et al. |
| 5,665,062 A | 9/1997 | Houser |
| 5,665,098 A | 9/1997 | Kelly et al. |
| 5,681,282 A | 10/1997 | Eggers |
| 5,693,043 A | 12/1997 | Kittrell et al. |
| 5,697,369 A | 12/1997 | Long, Jr. et al. |
| 5,697,909 A | 12/1997 | Eggers et al. |
| 5,713,942 A | 2/1998 | Stern et al. |
| 5,749,914 A | 5/1998 | Janssen |
| 5,755,753 A | 5/1998 | Knowlton |
| 5,775,338 A | 7/1998 | Hastings |
| 5,776,174 A | 7/1998 | Van Tassel |
| 5,792,105 A | 8/1998 | Lin et al. |
| 5,807,306 A | 9/1998 | Shapland et al. |
| 5,817,092 A | 10/1998 | Behl |
| 5,817,144 A | 10/1998 | Gregory |
| 5,848,969 A | 12/1998 | Panescu et al. |
| 5,860,974 A | 1/1999 | Abele |
| 5,869,127 A | 2/1999 | Zhong |
| 5,871,524 A | 2/1999 | Knowlton |
| 5,876,369 A | 3/1999 | Houser |
| 5,876,374 A | 3/1999 | Alba et al. |
| 5,876,397 A | 3/1999 | Edelman et al. |
| 5,904,651 A | 5/1999 | Swanson et al. |
| 5,906,636 A | 5/1999 | Casscells |
| 5,919,219 A | 7/1999 | Knowlton |
| 5,934,284 A | 8/1999 | Plaia et al. |
| 5,948,011 A | 9/1999 | Knowlton |
| 5,954,717 A | 9/1999 | Behl et al. |
| 5,999,678 A | 12/1999 | Murphy-Chutorian et al. |
| 6,010,522 A | 1/2000 | Barbut et al. |
| 6,019,757 A | 2/2000 | Scheldrup |
| 6,032,675 A | 3/2000 | Rubinsky |
| 6,033,357 A | 3/2000 | Ciezki et al. |
| 6,033,398 A | 3/2000 | Farley et al. |
| 6,036,689 A | 3/2000 | Tu et al. |
| 6,041,260 A | 3/2000 | Stern et al. |
| 6,050,994 A | 4/2000 | Sherman |
| 6,056,744 A | 5/2000 | Edwards |
| 6,056,746 A | 5/2000 | Goble et al. |
| 6,081,749 A | 6/2000 | Ingle et al. |
| 6,083,159 A | 7/2000 | Driscoll et al. |
| 6,091,995 A | 7/2000 | Ingle et al. |
| 6,117,128 A | 9/2000 | Gregory |
| 6,120,516 A | 9/2000 | Selmon et al. |
| 6,123,702 A | 9/2000 | Swanson et al. |
| 6,123,718 A | 9/2000 | Tu et al. |
| 6,129,725 A | 10/2000 | Tu et al. |
| 6,142,991 A | 11/2000 | Schatzberger |
| 6,152,899 A | 11/2000 | Farley et al. |
| 6,156,046 A | 12/2000 | Passafaro et al. |
| 6,161,048 A | 12/2000 | Sluijter et al. |
| 6,165,187 A | 12/2000 | Reger |
| 6,183,468 B1 | 2/2001 | Swanson et al. |
| 6,190,379 B1 | 2/2001 | Heuser et al. |
| 6,191,862 B1 | 2/2001 | Swanson et al. |
| 6,197,021 B1 | 3/2001 | Panescu et al. |
| 6,200,266 B1 | 3/2001 | Shokrollahi et al. |
| 6,203,561 B1 | 3/2001 | Ramee et al. |
| 6,211,247 B1 | 4/2001 | Goodman |
| 6,216,704 B1 | 4/2001 | Ingle et al. |
| 6,219,577 B1 | 4/2001 | Brown, III et al. |
| 6,228,076 B1 | 5/2001 | Winston et al. |
| 6,231,516 B1 | 5/2001 | Keilman et al. |
| 6,241,753 B1 | 6/2001 | Knowlton |
| 6,258,087 B1 | 7/2001 | Edwards et al. |
| 6,287,323 B1 | 9/2001 | Hammerslag |
| 6,293,942 B1 | 9/2001 | Goble et al. |
| 6,299,379 B1 | 10/2001 | Lewis |
| 6,299,623 B1 | 10/2001 | Wulfman |
| 6,309,379 B1 | 10/2001 | Willard et al. |
| 6,309,399 B1 | 10/2001 | Barbut et al. |
| 6,311,090 B1 | 10/2001 | Knowlton |
| 6,319,242 B1 | 11/2001 | Patterson et al. |
| 6,319,251 B1 | 11/2001 | Tu et al. |
| 6,325,799 B1 | 12/2001 | Goble |
| 6,328,699 B1 | 12/2001 | Eigler et al. |
| 6,350,276 B1 | 2/2002 | Knowlton |
| 6,353,751 B1 | 3/2002 | Swanson et al. |
| 6,364,840 B1 | 4/2002 | Crowley |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,389,311 B1 | 5/2002 | Whayne et al. |
| 6,391,024 B1 | 5/2002 | Sun et al. |
| 6,394,956 B1 | 5/2002 | Chandrasekaran et al. |
| 6,405,090 B1 | 6/2002 | Knowlton |

(56) References Cited

U.S. PATENT DOCUMENTS

| | | |
|---|---|---|
| 6,409,723 B1 | 6/2002 | Edwards |
| 6,413,255 B1 | 7/2002 | Stern |
| 6,421,559 B1 | 7/2002 | Pearlman |
| 6,423,057 B1 | 7/2002 | He et al. |
| 6,425,912 B1 | 7/2002 | Knowlton |
| 6,427,089 B1 | 7/2002 | Knowlton |
| 6,430,446 B1 | 8/2002 | Knowlton |
| 6,438,424 B1 | 8/2002 | Knowlton |
| 6,445,939 B1 | 9/2002 | Swanson et al. |
| 6,453,202 B1 | 9/2002 | Knowlton |
| 6,454,775 B1 | 9/2002 | Demarais et al. |
| 6,458,098 B1 | 10/2002 | Kanesaka |
| 6,461,378 B1 | 10/2002 | Knowlton |
| 6,470,216 B1 | 10/2002 | Knowlton |
| 6,482,202 B1 | 11/2002 | Goble et al. |
| 6,485,489 B2 | 11/2002 | Teirstein et al. |
| 6,488,679 B1 | 12/2002 | Swanson et al. |
| 6,497,711 B1 | 12/2002 | Plaia et al. |
| 6,508,765 B2 | 1/2003 | Suorsa et al. |
| 6,511,496 B1 | 1/2003 | Huter et al. |
| 6,522,926 B1 | 2/2003 | Kieval et al. |
| 6,524,274 B1 | 2/2003 | Rosenthal et al. |
| 6,540,761 B2 | 4/2003 | Houser |
| 6,552,796 B2 | 4/2003 | Magnin et al. |
| 6,558,381 B2 | 5/2003 | Ingle et al. |
| 6,558,382 B2 | 5/2003 | Jahns et al. |
| 6,569,109 B2 | 5/2003 | Sakurai et al. |
| 6,569,177 B1 | 5/2003 | Dillard et al. |
| 6,570,659 B2 | 5/2003 | Schmitt |
| 6,582,423 B1 | 6/2003 | Thapliyal et al. |
| 6,589,238 B2 | 7/2003 | Edwards et al. |
| 6,592,526 B1 | 7/2003 | Lenker |
| 6,605,061 B2 | 8/2003 | Vantassel et al. |
| 6,632,193 B1 | 10/2003 | Davison et al. |
| 6,652,515 B1 | 11/2003 | Maguire et al. |
| 6,673,066 B2 | 1/2004 | Werneth |
| 6,673,290 B1 | 1/2004 | Whayne et al. |
| 6,690,181 B1 | 2/2004 | Dowdeswell et al. |
| 6,692,490 B1 | 2/2004 | Edwards |
| 6,706,037 B2 | 3/2004 | Zvuloni et al. |
| 6,714,822 B2 | 3/2004 | King et al. |
| 6,720,350 B2 | 4/2004 | Kunz et al. |
| 6,736,811 B2 | 5/2004 | Panescu et al. |
| 6,760,616 B2 | 7/2004 | Hoey |
| 6,769,433 B2 | 8/2004 | Zikorus et al. |
| 6,771,996 B2 | 8/2004 | Bowe et al. |
| 6,786,904 B2 | 9/2004 | Doscher |
| 6,807,444 B2 | 10/2004 | Tu et al. |
| 6,829,497 B2 | 12/2004 | Mogul |
| 6,837,886 B2 | 1/2005 | Collins et al. |
| 6,845,267 B2 | 1/2005 | Harrison et al. |
| 6,849,073 B2 | 2/2005 | Hoey et al. |
| 6,853,425 B2 | 2/2005 | Kim et al. |
| 6,926,716 B2 | 8/2005 | Baker et al. |
| 6,932,776 B2 | 8/2005 | Carr |
| 6,936,047 B2 | 8/2005 | Nasab et al. |
| 6,953,425 B2 | 10/2005 | Brister |
| 6,955,174 B2 | 10/2005 | Joye |
| 6,958,075 B2 | 10/2005 | Mon et al. |
| 6,962,584 B1 | 11/2005 | Stone |
| 6,964,660 B2 | 11/2005 | Maguire et al. |
| 6,972,024 B1 | 12/2005 | Kilpatrick |
| 7,008,667 B2 | 3/2006 | Chudzik et al. |
| 7,011,508 B2 | 3/2006 | Lum |
| 7,104,987 B2 | 9/2006 | Biggs et al. |
| 7,137,980 B2 | 11/2006 | Buysse et al. |
| 7,162,303 B2 | 1/2007 | Levin et al. |
| 7,192,427 B2 | 3/2007 | Chapelon et al. |
| 7,200,445 B1 | 4/2007 | Dalbec et al. |
| 7,252,664 B2 | 8/2007 | Nasab et al. |
| 7,288,096 B2 | 10/2007 | Chin |
| 7,291,146 B2 | 11/2007 | Steinke et al. |
| 7,326,235 B2 | 2/2008 | Edwards |
| 7,425,212 B1 | 9/2008 | Danek et al. |
| 7,426,409 B2 | 9/2008 | Casscells, III et al. |
| 7,497,858 B2 | 3/2009 | Chapelon et al. |
| 7,556,624 B2 | 7/2009 | Laufer et al. |
| 7,617,005 B2 | 11/2009 | Demarais et al. |
| 7,632,268 B2 | 12/2009 | Edwards et al. |
| 7,653,438 B2 | 1/2010 | Deem et al. |
| 7,691,080 B2 | 4/2010 | Seward et al. |
| 7,717,948 B2 | 5/2010 | Demarais et al. |
| 7,854,734 B2 | 12/2010 | Biggs et al. |
| 7,862,565 B2 | 1/2011 | Eder et al. |
| 7,901,400 B2 | 3/2011 | Wham et al. |
| 7,942,874 B2 | 5/2011 | Eder et al. |
| 2001/0051774 A1 | 12/2001 | Littrup et al. |
| 2002/0062123 A1 | 5/2002 | McClurken et al. |
| 2002/0072686 A1* | 6/2002 | Hoey et al. .............. 600/547 |
| 2002/0077592 A1 | 6/2002 | Barry |
| 2002/0082552 A1 | 6/2002 | Ding et al. |
| 2002/0087156 A1 | 7/2002 | Maguire et al. |
| 2002/0091381 A1 | 7/2002 | Edwards |
| 2002/0103445 A1* | 8/2002 | Rahdert et al. ............ 600/549 |
| 2002/0107511 A1 | 8/2002 | Collins et al. |
| 2002/0143324 A1 | 10/2002 | Edwards |
| 2003/0004510 A1 | 1/2003 | Wham et al. |
| 2003/0028114 A1 | 2/2003 | Casscells, III et al. |
| 2003/0050635 A1 | 3/2003 | Truckai et al. |
| 2003/0060857 A1 | 3/2003 | Perrson et al. |
| 2003/0060858 A1 | 3/2003 | Kieval et al. |
| 2003/0114791 A1 | 6/2003 | Rosenthal et al. |
| 2003/0195501 A1 | 10/2003 | Sherman et al. |
| 2003/0212394 A1 | 11/2003 | Pearson et al. |
| 2003/0220639 A1 | 11/2003 | Chapelson et al. |
| 2003/0229384 A1 | 12/2003 | Mon |
| 2004/0006333 A1 | 1/2004 | Arnold et al. |
| 2004/0006359 A1 | 1/2004 | Laguna |
| 2004/0064093 A1 | 4/2004 | Hektner et al. |
| 2004/0073206 A1 | 4/2004 | Foley et al. |
| 2004/0111016 A1 | 6/2004 | Casscells, III et al. |
| 2004/0122421 A1 | 6/2004 | Wood |
| 2004/0181165 A1 | 9/2004 | Hoey et al. |
| 2004/0186468 A1 | 9/2004 | Edwards |
| 2005/0010208 A1 | 1/2005 | Winston et al. |
| 2005/0015125 A1 | 1/2005 | Mioduski et al. |
| 2005/0033136 A1 | 2/2005 | Govari et al. |
| 2005/0090820 A1 | 4/2005 | Cornelius et al. |
| 2005/0096647 A1 | 5/2005 | Steinke et al. |
| 2005/0203434 A1 | 9/2005 | Kassab |
| 2005/0251116 A1 | 11/2005 | Steinke et al. |
| 2006/0085054 A1 | 4/2006 | Zikorus et al. |
| 2006/0089638 A1 | 4/2006 | Carmel |
| 2006/0149166 A1 | 7/2006 | Zvuloni |
| 2006/0184060 A1 | 8/2006 | Belacazar et al. |
| 2006/0235286 A1 | 10/2006 | Stone et al. |
| 2006/0246143 A1 | 11/2006 | Ege |
| 2006/0280858 A1 | 12/2006 | Kokish |
| 2007/0078435 A1 | 4/2007 | Stone et al. |
| 2007/0173805 A1 | 7/2007 | Weinberg et al. |
| 2007/0173899 A1 | 7/2007 | Levin et al. |
| 2007/0197891 A1 | 8/2007 | Shachar et al. |
| 2007/0265687 A1 | 11/2007 | Deem et al. |
| 2008/0161801 A1 | 7/2008 | Steinke et al. |
| 2008/0188912 A1 | 8/2008 | Stone et al. |
| 2008/0188913 A1 | 8/2008 | Stone et al. |
| 2008/0262489 A1* | 10/2008 | Steinke ..................... 606/33 |
| 2009/0018609 A1 | 1/2009 | DeLorenzo |
| 2009/0062873 A1 | 3/2009 | Wu et al. |
| 2009/0074828 A1 | 3/2009 | Alexis et al. |
| 2010/0076299 A1 | 3/2010 | Gustus et al. |
| 2010/0125239 A1 | 5/2010 | Perry et al. |
| 2010/0125268 A1 | 5/2010 | Gustus et al. |
| 2010/0137952 A1 | 6/2010 | Demarais et al. |
| 2010/0160906 A1 | 6/2010 | Jarrard |
| 2010/0204560 A1 | 8/2010 | Salahieh et al. |
| 2010/0249702 A1 | 9/2010 | Magana et al. |
| 2010/0286684 A1 | 11/2010 | Hata et al. |
| 2010/0324472 A1 | 12/2010 | Wulfman |
| 2011/0092880 A1 | 4/2011 | Gertner |
| 2011/0104061 A1 | 5/2011 | Seward |
| 2011/0118598 A1 | 5/2011 | Gertner |
| 2011/0118600 A1 | 5/2011 | Gertner |
| 2011/0118726 A1 | 5/2011 | De La Rama |

(56) References Cited

U.S. PATENT DOCUMENTS

| | | | |
|---|---|---|---|
| 2011/0178403 A1 | 7/2011 | Weng et al. |
| 2011/0207758 A1 | 8/2011 | Sobotka |
| 2011/0270238 A1 | 11/2011 | Rizq et al. |
| 2011/0306851 A1 | 12/2011 | Wang |
| 2011/0307034 A1 | 12/2011 | Hastings et al. |
| 2011/0319809 A1 | 12/2011 | Smith |
| 2012/0029496 A1 | 2/2012 | Smith |
| 2012/0029500 A1 | 2/2012 | Jenson |
| 2012/0029509 A1 | 2/2012 | Smith |
| 2012/0029511 A1 | 2/2012 | Smith |
| 2012/0029512 A1 | 2/2012 | Willard et al. |
| 2012/0157987 A1 | 6/2012 | Steinke et al. |
| 2012/0157989 A1 | 6/2012 | Stone et al. |
| 2012/0158101 A1 | 6/2012 | Stone et al. |

FOREIGN PATENT DOCUMENTS

| | | | |
|---|---|---|---|
| CN | 102271607 A | 12/2011 |
| DE | 102005041601 A1 | 4/2007 |
| DE | 102008048616 A1 | 4/2010 |
| EP | 558297 A2 | 9/1993 |
| EP | 647435 A1 | 4/1995 |
| EP | 634910 B1 | 8/1997 |
| EP | 868884 A2 | 10/1998 |
| EP | 1005838 A1 | 6/2000 |
| EP | 1053720 A1 | 11/2000 |
| EP | 1064886 A1 | 1/2001 |
| EP | 1181895 A2 | 2/2002 |
| EP | 1297795 A1 | 6/2002 |
| EP | 1264613 A2 | 12/2002 |
| EP | 1286625 A1 | 3/2003 |
| EP | 1332724 A1 | 8/2003 |
| EP | 866675 B1 | 10/2003 |
| EP | 1433448 A1 | 6/2004 |
| EP | 1442719 A1 | 8/2004 |
| EP | 1547537 A1 | 6/2005 |
| EP | 1634542 A1 | 3/2006 |
| EP | 1698296 A1 | 6/2006 |
| EP | 1709922 A1 | 10/2006 |
| EP | 1946712 A1 | 7/2008 |
| EP | 1961394 A2 | 8/2008 |
| EP | 1715798 B1 | 4/2009 |
| EP | 2092957 A1 | 8/2009 |
| EP | 2208506 A1 | 7/2010 |
| EP | 2241279 A1 | 10/2010 |
| EP | 2329859 A1 | 6/2011 |
| GB | 2313062 A | 11/1997 |
| GB | 2453601 A | 4/2009 |
| JP | 1995-213621 A | 8/1995 |
| JP | 1995-313603 A | 12/1995 |
| JP | 2003-510126 A | 3/2003 |
| WO | WO 91/03207 A1 | 3/1991 |
| WO | WO 91/17731 A1 | 11/1991 |
| WO | WO 92/22239 A1 | 12/1992 |
| WO | WO 93/20747 | 10/1993 |
| WO | WO 93/20770 A2 | 10/1993 |
| WO | WO 94/18896 A1 | 9/1994 |
| WO | WO 94/28809 A1 | 12/1994 |
| WO | WO 95/01751 A1 | 1/1995 |
| WO | WO 96/34559 A1 | 11/1996 |
| WO | WO 97/03604 A1 | 2/1997 |
| WO | WO 97/17104 | 5/1997 |
| WO | WO 97/20510 A1 | 6/1997 |
| WO | WO 97/32532 A1 | 9/1997 |
| WO | WO 97/40760 A1 | 11/1997 |
| WO | WO 97/45156 A2 | 12/1997 |
| WO | WO 98/18393 A1 | 5/1998 |
| WO | WO 98/29030 A1 | 7/1998 |
| WO | WO 98/34565 A1 | 8/1998 |
| WO | WO 98/35638 A1 | 8/1998 |
| WO | WO 98/40023 A1 | 9/1998 |
| WO | WO 99/00060 | 1/1999 |
| WO | WO 99/16370 A1 | 4/1999 |
| WO | WO 99/21608 A1 | 5/1999 |
| WO | WO 99/34741 A1 | 7/1999 |
| WO | WO 99/44522 A1 | 9/1999 |
| WO | WO 00/01313 A1 | 1/2000 |
| WO | WO 00/10475 A1 | 3/2000 |
| WO | WO 00/51513 A1 | 9/2000 |
| WO | WO 00/59394 A1 | 10/2000 |
| WO | WO 00/62727 A1 | 10/2000 |
| WO | WO 00/64387 A1 | 11/2000 |
| WO | WO 00/69376 A1 | 11/2000 |
| WO | WO 00/72909 A1 | 12/2000 |
| WO | WO 01/22897 A1 | 4/2001 |
| WO | WO 01/37746 A1 | 5/2001 |
| WO | WO 01/87172 A1 | 5/2001 |
| WO | WO 01/74255 A | 10/2001 |
| WO | WO 01/87154 A1 | 11/2001 |
| WO | WO 01/95820 A1 | 12/2001 |
| WO | WO 02/15807 A1 | 2/2002 |
| WO | WO 02/28475 A1 | 4/2002 |
| WO | WO 02/39915 A1 | 5/2002 |
| WO | WO 02/058549 A1 | 8/2002 |
| WO | WO 02/080766 A2 | 10/2002 |
| WO | WO 02/087679 | 11/2002 |
| WO | WO 02/089686 | 11/2002 |
| WO | WO 03/077781 A1 | 9/2003 |
| WO | WO 2004/047659 A2 | 6/2004 |
| WO | WO 2004/049976 A1 | 6/2004 |
| WO | WO 2004/064606 A2 | 8/2004 |
| WO | WO 2004/069300 A2 | 8/2004 |
| WO | WO 2004/076146 A2 | 9/2004 |
| WO | WO 2004/098694 A1 | 11/2004 |
| WO | WO 2004/105807 A2 | 12/2004 |
| WO | WO 2005/037070 A2 | 4/2005 |
| WO | WO 2005/041748 | 5/2005 |
| WO | WO 2005/074829 A1 | 8/2005 |
| WO | WO 2006/041881 A2 | 4/2006 |
| WO | WO 2006/105121 A2 | 10/2006 |
| WO | WO 2006/116198 A2 | 11/2006 |
| WO | WO 2007/011634 A1 | 1/2007 |
| WO | WO 2007/014063 A2 | 2/2007 |
| WO | WO 2007/047870 A2 | 4/2007 |
| WO | WO 2007/113865 A1 | 10/2007 |
| WO | WO 2007/135431 A2 | 11/2007 |
| WO | WO 2007/146215 A2 | 12/2007 |
| WO | WO 2008/003058 A2 | 1/2008 |
| WO | WO 2008/009972 A2 | 1/2008 |
| WO | WO 2008/010150 A2 | 1/2008 |
| WO | WO 2008/036281 A2 | 3/2008 |
| WO | WO 2008/049084 A2 | 4/2008 |
| WO | WO 2008/061152 A2 | 5/2008 |
| WO | WO 2009/036471 A1 | 3/2009 |
| WO | WO 2009/082635 A1 | 7/2009 |
| WO | WO 2009/088678 A1 | 7/2009 |
| WO | WO 2009/113064 A2 | 9/2009 |
| WO | WO 2009/137819 A1 | 11/2009 |
| WO | WO 2010/042653 A1 | 4/2010 |
| WO | WO 2010/048007 A1 | 4/2010 |
| WO | WO 2010/056771 A1 | 5/2010 |
| WO | WO 2010/057043 A1 | 5/2010 |
| WO | WO 2010/070766 A1 | 6/2010 |
| WO | WO 2010/099207 A1 | 9/2010 |
| WO | WO 2010/120944 A2 | 10/2010 |
| WO | WO 2010/134503 A1 | 11/2010 |
| WO | WO 2011/055143 A2 | 5/2011 |
| WO | WO 2011/060339 A1 | 5/2011 |
| WO | WO 2011/126580 A2 | 10/2011 |

OTHER PUBLICATIONS

Carrington, "Future of CVI: its all about the plaque," Diagnostic Imaging Special Edition Forum, retrieved online on Sep. 3, 2003, <http://dimag.com/specialedition/cardiacimg.html>, 5 pgs.

Cimino, "Preventing plaque attack," retrieved online on Sep. 3, 2003, <http://Masshightech.com/displayarticledetail.ap?art_id=52283 &cat_id=10>, 3 pgs.

Dahm et al., "Relation of degree of laser debulking of in-stent restenosis as a predictor of restenosis rate," Am. J. Cardiol., 90:68-70, 2002.

De Korte et al., "Characterization of placque components with intravascular ultrasounds elastography in human femoral and coronary arteries in vitro," Circulation 2000, 102:617-23.

(56) References Cited

OTHER PUBLICATIONS

Durney et al., Radiofrequency Radiation Dosimetry Handbook (with table of contents), Oct. 1986, 4th ed., 7 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/handbook/home.html.

Fournier-Desseux et al. "Assessment of 1-lead and 2-lead electrode patterns in electrical impedance endotomography", Physiol. Meas. (2005) 26:337-349.

Fujimori et al., "Significant prevention of in-stent restenosis by evens blue in patients with acute myocardial infarction," Abstract #2925, AHA, 2002, 1 pg.

Fujita, "Sarpogrelate, an antagonist of 5-HT2a receptor treatment reduces restenosis after coronary stenting," Abstract #2927, AHA, 2002, 1 pg.

Gabriel et al., Compilation of the Dielectric Properties of Body Tissues at RF and Microwave Frequencies (with table of contents), Jun. 1996, 17 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/dielectric/Report/Report.html.

Gabriel et al., Compilation of the Dielectric Properties of Body Tissues at RF and Microwave Frequencies, Appendix A, Jun. 1996, 21 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/dielectric/Appendix.A/AppendixA.html.

Gabriel et al., Compilation of the Dielectric Properties of Body Tissues at RF and Microwave Frequencies, Appendix C, Jun. 1996, 6 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/dielectric/Appendix.C/AppendixC.html.

Gregory et al., "Liquid core light guide for laser angioplasty," Journal of Quantum Electronics, 26(12):2289-96, Dec. 1990.

Intrluminal, "Product description," retrieved online on Sep. 3, 2003, <http://www.intraluminal.com/products/index.html>, 1 pg.

Kaplan et al., "Healing after arterial dilatation with radiofrequency thermal and nonthermal balloon angioplasty systems," J Invest Surg. Jan.-Feb. 1993;6(1):33-52.

Kolata, "New studies question value of opening arteries," New York Times, retrieved online retrieved on Jan. 25, 2005, <http://nytimes.com/2004/03/21/health/21HEAR.html?ei=5070&en=641bc03214e&ex=11067>, 5 pgs.

Konings et al., "Development of an intravascular impedance catheter for detection of fatty lesions in arteries," IEEE Transactions on medical imaging, vol. 16, No. 4, Aug. 1997.

Kurtz et al., "Lamellar refractive surgery with scanned intrastromal picosecond and femtosecond laser pulses in animal eyes," J. Refract. Surg. 14:541-8, Sep./Oct. 1998.

Lightlab Imaging Technology, "Advantages of OCT," retrieved online on Sep. 3, 2003, <http:www.lightlabimaging.com/advantage.html>, 2 pgs.

Lightlab Imaging Technology, "Image gallery," retrieved online on Sep. 3, 2003, <http:lightlabimaging.com/gallery/cvpstill.html>, 4 pgs.

Lightlab Imaging Technology, "Lightlab imaging starts US cardiology clinical investigations," Lightlab Company Press Release, retrieved online on Sep. 3, 2003, <http://www.lightlabimaging.com/press/cardtrails.html>, 2 pgs.

Lightlab Imaging Technology, "Lightlab sees bright prospects for cardiac applications of OCT technology," The Graysheet Medical Devices Diagnostics & Instrumentation, vol. 27, No. 35, retrieved online on Sep. 3, 2003, <http://www.lightlabimaging.com/press/graysheet.html>, 1 pg.

Lightlab Imaging Technology, "What is OCT?," retrieved online on Sep. 3, 2003,<http:lightlabimaging.com/oct.html>, 2 pgs.

Lightlab Imaging Technology, "Why use OCT?," retrieved online on Sep. 3, 2003, <http:lightlabimaging.com/whyoct.html>, 2 pgs.

Lima et al., "Efficacy and safety of oral sirolimus to treat and prevent in-stent restenosis: a pilot study results," Abstract #2929, AHA, 2002, 1 pg.

Lima et al., "Systemic immunosuppression inhibits in-stent coronary intimal proliferation in renal transplant patients," Abstract #2928, AHA, 2002, 1 pg.

MIT TechTalk, "Laser catheter to aid coronary surgery," Jan. 9, 1991, retrieved online on Feb. 7, 2005, <http://web.mit.edu/newsoffice/tt/1991/jan09/24037.html>, 4 pgs.

Morice et al., "A randomized comparison of a sirolimus-eluting stent with a starndard stent for coronary revascularization," N. Engl. J. Med., 346(23):1773-9.

Muller-Leisse et al., "Effectiveness and safety of ultrasonic atherosclerotic plaque ablation: in vitro investigation," CardioVas. Intervent. Radiol., 1993, 16:303-7.

Nair A. et al., "Regularized autoregressive analysis of intravascular ultrasound backscatter. Improvement in spatial accuracy of tissue maps," IEEE Transactions on Ultrasonics, Ferroelectrics, and Frequency Control, vol. 51, No. 4, Apr. 2004.

Popma et al., "Chapter 38—Percutaneous coronary and valvular intervention," Heart Disease: A Textbook of Cardiovascular Medicine, 6th ed., 2001, W.B. Saunders Company, pp. 1364-1405.

Scheller, "Intracoronary paclitaxel added to contrast media inhibits in-stent restenosis of porcine coronary arteries," Abstract #2227, AHA, 2002, 1 pg.

Shaffer, "Scientific basis of laser energy," Clin. Sports Med., 2002, 21(4):585-98.

Shmatukha, "MRI temperature mapping during thermal balloon angioplasty," Phys. Med. Biol. 51, 2006, N163-N171.

Slager et al., "Vaporization of atherosclerotic plaques by spark erosion," J. Am. Coll. Cardiol., 5(6):1382-6, Jun. 1985.

Stiles et al., "Simulated characterization of atherosclerotic lesions in the coronary arteries by measurement of bioimpedance," IEEE Transactions on Biomedical Engineering, vol. 50, No. 4, Jul. 2003.

Süselbeck et al. "Intravascular electric impedance spectroscopy of atherosclerotic lesions using a new impedance system", Basic Res Cardiol (2005) 100:446-452.

Suselbeck et al., "In vivo intravascular electrical impedance spectroscopy using a new catheter with integrated microelectrodes," Basic Res. Cardiol. 100:28-34, 2005.

Van Den Berg, "Light echoes image the human body," OLE, Oct. 2001, pp. 35-37.

Romer et al., "Histopathology of Human Coronary Atherosclerosis by Quantifying its Chemical Composition with Raman Spectroscopy," Circulation. (1998) 97: 878-885.

Volcano Therapeutics, "Product—Functional Measurement", [online] [retrieved on Mar. 9, 2003]. Retrieved from the Internet: <http://www.volcanotherapeutics.com/pages/products/functional_measurement-us.html> 2 pages total.

Supplementary Partial European Search Report of Application No. 04816863.7, mailed May 5, 2009, 7 pages total.

European Search Report and Search Opinion of EP Patent Application No. 07844421.3, mailed Jan. 4, 2010, 15 pages total.

Brown S.L. et al., "Radiofrequencey capacitivie heaters: the effect of coupling medium resistivity on power absorption along a mouse leg," Phys. Med. Biol., 1993, 38:1-12, abstract.

Carrington, "Future of CVI: it's all about the plaque," Diagnostic Imaging Special Edition Forum, retrieved online on Sep. 3, 2003, <http://dimag.com/specialedition/cardiacimg.html>, 5 pgs.

Dahm et al., "Relation of degree of laser debulking of in-stent restenosis as a predictor of restenosis rate," Am. J. Cardiol., 90:68-70, 2002

De Korte C.L. et al., "Characterization of placque components with intravascular ultrasounds elastography in human femoral and coronary arteries in vitro," Circulation 2000, 102:617-23

Durney, C., et al., Radiofrequency Radiation Dosimetry Handbook (with table of contents), Oct. 1986, 4th ed., 7 pages, Armstrong Laboratory (AFMC) Occupational and Environmental Health Directorate Radiofrequency Radiation Division, USAF School of Aero-

(56) References Cited

OTHER PUBLICATIONS space Medicine, Aerospace Medical Division (AFSC), Brooks Air Force Base, http://www.brooks.af.mil/AFRL/HED/hedr/reports/handbook/home.html.
Fujimori et al., "Significant prevention of in-stent restenosis by evans blue in patients with acute myocardial infarction," Abstract #2925, AHA, 2002, 1 pg.
Fujita, "Sarpogrelate, an antagonist of $5\text{-}HT_{2a}$ receptor treatment reduces restenosis after coronary stenting," Abstract #2927, AHA, 2002, 1 pg.
Gabriel, C., et al., Compilation of the Dielectric Properties of Body Tissues at RF and Microwave Frequencies (with table of contents), Jun. 1996, 17 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/dielectric/Report/Report.html.
Gabriel, C., et al., Compilation of the Dielectric Properties of Body Tissues at RF and Microwave Frequencies, Appendix A, Jun. 1996, 21 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/dielectric/Appendix.A/AppendixA.html.
Gabriel, C., et al., Compilation of the Dielectric Properties of Body Tissues at RF and Microwave Frequencies, Appendix C, Jun. 1996, 6 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/dielectric/Appendix.C/AppendixC.html.
Gregory et al., "Liquid core light guide for laser angioplasty," Journal of Quantum Electronics, 26(12):2289-96, Dec. 1990
Kolata, "New studies question value of opening arteries," New York Times, retrieved online retrieved on Jan. 25, 2005, <http://nytimes.com/2004/03/21/health/21HEAR.html?ei=5070&en=641bc03214e&ex=11067 >, 5 pgs.
Konings M.K. et al., "Development of an intravascular impedance catheter for detection of fatty lesions in arteries," IEEE Transactions on medical imaging, vol. 16, No. 4, Aug. 1997
Kurtz et al., "Lamellar refractive surgery with scanned intrastromal picosecond and femtosecond laser pulses in animal eyes," J. Refract. Surg. 14:541-8, Sep./Oct. 1998
Lightlab Imaging Technology, "Lightlab sees bright prospects for cardiac applications of OCT technology," The Graysheet Medical Devices Diagnostics & Instrumentation, vol. 27, No. 35, retrieved online on Sep. 3, 2003, <http://www.lightlabimagino.com/press/graysheet.html>, 1 pg.
Lightlab Imaging Technology, "Why use OCT"?," retrieved online on Sep. 3, 2003, <http:lightlabimaging.com/whyoct.html>, 2 pgs.
Shmatukha A.V., "MRI temperature mapping during thermal balloon angioplasty," Phys. Med. Biol. 51, 2006, N163-N171.
Stiles D.K. et al., "Simulated characterization of atherosclerotic lesions in the coronary arteries by measurement of bioimpedance," IEEE Transactions on Biomedical Engineering, vol. 50, No. 4, Jul. 2003.
Suselbeck T. et al., "In vivo intravascular electrical impedance spectroscopy using a new catheter with integrated microelectrodes," Basic Res. Cardiol. 100:28-34, 2005.
Examiner's Report of Canadian Patent Application No. 2,539,026, mailed Feb. 6, 2012, 4 pages total.
Office Action issued in Chinese Patent Application No. 200480030163.9, mailed Jan. 16, 2009, 8 pages total.
Office Action issued in Chinese Patent Application No. 200480030163.9, mailed Mar. 28, 2008, 7 pages total.
Office Action issued in Chinese Patent Application No. 200480030163.9, mailed Aug. 31, 2007, 8 pages total.
Office Action issued in Chinese Patent Application No. 200480030163.9, mailed Jul. 31, 2009, 5 pages total.
Office Action issued in European Application No. 04816863.7, mailed Jun. 4, 2010, 5 pages total.
Office Action issued in European Application No. 04816863.7, mailed Dec. 5, 2011, 4 pages total.
Office Action issued in European Application No. 04816863.7, mailed Jan. 22, 2010, 6 pages total.
Formal Inquiry issued in Japanese Patent Application No. 2006-526351, mailed Jan. 17, 2012, 5 pages total.
Notice of the Reason for Refusal issued in Japanese Patent Application No. 2006-526351, mailed Apr. 27, 2010, 6 pages total.
Final Decision of Rejection issued in Japanese Patent Application No. 2006-526351, mailed Jan. 18, 2011, 4 pages total.
European Search Report and Search Opinion of EP Patent Application No. 12151957.3, mailed Apr. 16, 2012, 8 pages total.
Office Action issued in Chinese Patent Application No. 200680016424.0, mailed Apr. 13, 2010, 10 pages total.
European Search Report and Search Opinion of EP Patent Application No. 06748830.4, mailed Nov. 16, 2009, 12 pages total.
Partial European Search Report of EP Patent Application No. 11191822.3, mailed Mar. 19, 2012, 7 pages total.
Office Action issued in Chinese Patent Application No. 201110031923.X, mailed Nov. 17, 2011, 16 pages total.
Office Action issued in Chinese Patent Application No. 201110031923.X, mailed May 22, 2012, 10 pages total.
Examiner's First Report of Australian Patent Application No. 2007310988, mailed May 23, 2012, 4 pages total.
European Search Report and Search Opinion of EP Patent Application No. 12155447.1, mailed May 10, 2012, 6 pages total.
International Search Report and Written Opinion of PCT Application No. PCT/US2009/064027, mailed Jan. 19, 2010, 9 pages total.
European Search Report and Search Opinion of EP Patent Application No. 07844417.1, mailed Nov. 5, 2009.
European Search Report and Search Opinion of EP Patent Application No. 12154120.5, mailed May 8, 2012, 8 pages total.
European Search Report and Search Opinion of EP Patent Application No. 07844424.7, mailed Nov. 11, 2009, 11 pages total.
Partial European Search Report of EP Patent Application No. 12154069.4, mailed May 10, 2012, 5 pages total.
International Search Report and Written Opinion of PCT Application No. PCT/US2009/064465, mailed Jan. 13, 2010, 13 pages total.
International Search Report of PCT Application No. PCT/US09/57728, mailed Nov. 30, 2009, 10 pages total. (2410PC).
International Search Report and Written Opinion of PCT/US2010/034789, mailed Jul. 9, 2010, 13 pages total.
International Search Report and Written Opinion of PCT/US2011/00661, mailed Nov. 18, 2011, 14 pages total.
Brown et al., "Observations on the shrink temperature of collagen and its variations with age and disease," Ann Rheum Dis, Jun. 1, 1958, 17(2):196-208.
Notice of the Reason for Refusal issued in Japanese Patent Application No. 2009-533544, mailed Jun. 19, 2012, 3 pages total.
Summons to Attend Oral Proceedings of EP Patent Application No. 07844424.7, mailed Jul. 5, 2012, 7 pages total.
European Search Report and Search Opinion of EP Patent Application No. 11191822.3, mailed Jun. 13, 2012, 13 pages total.
Office Action issued in European Application No. 07844421.3, mailed Aug. 23, 2012, 5 pages total.
Notice of the Reason for Refusal issued in Japanese Patent Application No. 2009-533546, mailed Jun. 19, 2012, 6 pages total.
Extended European Search Report and Search Opinion of EP Patent Application No. 12154069.4, mailed Sep. 17, 2012, 13 pages total.
Notice of the Reason for Refusal issued in Japanese Patent Application No. 2006-526351, mailed Sep. 18, 2012, 20 pages total.
Office Action issued in Chinese Patent Application No. 201110031923.X, mailed on Sep. 6, 2012, 11 pages total.
Office Action issued in Australian Patent Application No. 2010248955, mailed Sep. 13, 2012, 4 pages total.

* cited by examiner

INPEDANCE OF DISEASED AND NON-DISEASED TISSUE

| Survival | Data | # of Animals | # of Sites | Energy setting (Joules) | Power setting (Watts) | Time setting (seconds) |
|---|---|---|---|---|---|---|
| 6-9 days | All Sites | 9.5 | 34 | 1-135 | 1-15 | 1-10 |
| | Included | 5 | 20 | 1-32 | 1-10 | 1-4 |
| 32-36 days | All Sites | 3 | 13 | 2-32 | 1-10 | 1-8 |
| | Included | 1 | 6 | 15-32 | 4-5 | 3-8 |
| 82-90 days | All Sites | 3.5 | 16 | 2-112 | 1-20 | 1-9 |
| | Included | 3 | 14 | 2-10 | 1-5 | 2-4 |

FIG. 38A

| Total N | Power setting (Watts) | Time setting (seconds) | Energy setting (Joules) |
|---|---|---|---|
| 2 | 1 | 1 | 1.0 |
| 2 | 1 | 2 | 2.0 |
| 3 | 2 | 1 | 2.0 |
| 6 | 2 | 2 | 4.0 |
| 4 | 2 | 3 | 6.0 |
| 2 | 2 | 4 | 8.0 |
| 4 | 3 | 2 | 6.0 |
| 2 | 4 | 2 | 8.0 |
| 1 | 4 | 4 | 16.0 |
| 1 | 4 | 6 | 24.0 |
| 1 | 4 | 8 | 32.0 |
| 4 | 5 | 2 | 10.0 |
| 4 | 5 | 3 | 15.0 |
| 1 | 6 | 4 | 24.0 |
| 1 | 8 | 2 | 16.0 |
| 1 | 8 | 4 | 32.0 |
| 1 | 10 | 2 | 20.0 |

FIG. 38B

TUNED RF ENERGY AND ELECTRICAL TISSUE CHARACTERIZATION FOR SELECTIVE TREATMENT OF TARGET TISSUES

CROSS-REFERENCES TO RELATED APPLICATIONS

This application claims the benefit under 35 USC 119(e) of U.S. Provisional Application No. 60/852,787, filed on Oct. 18, 2006, and entitled "Tuned RF Energy And Electrical Tissue Characterization For Selective Treatment Of Target Tissues"; and U.S. Provisional Application No. 60/921,973, filed on Apr. 4, 2007, and entitled "Tuned RF Energy And Electrical Tissue Characterization For Selective Treatment Of Target Tissues".

This application is related to U.S. patent application Ser. No. 11/392,231, filed on Mar. 28, 2006; which claims the benefit under 35 USC 119(e) of U.S. Provisional Application No. 60/666,766, filed on Mar. 28, 2005, and entitled "Tuned RF Energy for Selective Treatment of Atheroma and Other Target Tissues and/or Structures"; and is related to U.S. patent application Ser. No. 10/938,138, filed on Sep. 10, 2004, and entitled "Selectable Eccentric Remodeling and/or Ablation of Atherosclerotic Material"; U.S. Provisional Application No. 60/976,733, filed on Oct. 1, 2007, and entitled "System for Inducing Desirable Temperature Effects on Body Tissue"; and U.S. Provisional Application No. 60/976,752, filed on Oct. 1, 2007, entitled "Inducing Desirable Temperature Effects On Body Tissue", the full disclosures of which are incorporated herein by reference.

BACKGROUND OF THE INVENTION

Field of the Invention

The present invention is generally related to medical devices, systems, and methods. In exemplary embodiments, the invention provides catheter-based diagnosis and/or treatment for luminal diseases, particularly for atherosclerotic plaque, vulnerable or "hot" plaque, and the like. The structures of the invention allow guided eccentric atherosclerotic material analysis, remodeling and/or removal, often using both electrical diagnostic signals and electrosurgical energy.

Physicians use catheters to gain access to and repair interior tissues of the body, particularly within the lumens of the body such as blood vessels. For example, balloon angioplasty and other catheters often are used to open arteries that have been narrowed due to atherosclerotic disease.

Balloon angioplasty is often effective at opening an occluded blood vessel, but the trauma associated with balloon dilation can impose significant injury, so that the benefits of balloon dilation may be limited in time. Stents are commonly used to extend the beneficial opening of the blood vessel.

Stenting, in conjunction with balloon dilation, is often the preferred treatment for atherosclerosis. In stenting, a collapsed metal framework is mounted on a balloon catheter which is introduced into the body. The stent is manipulated into the site of occlusion and expanded in place by the dilation of the underlying balloon. Stenting has gained widespread acceptance, and produces generally acceptable results in many cases. Along with treatment of blood vessels (particularly the coronary arteries), stents can also be used in treating many other tubular obstructions within the body, such as for treatment of reproductive, gastrointestinal, and pulmonary obstructions.

Restenosis or a subsequent narrowing of the body lumen after stenting has occurred in a significant number of cases. More recently, drug coated stents (such as Johnson and Johnson's Cypher™ stent, the associated drug comprising Sirolimus™) have demonstrated a markedly reduced restenosis rate, and others are developing and commercializing alternative drug eluting stents. In addition, work has also been initiated with systemic drug delivery (intravenous or oral) which may also improve the procedural angioplasty success rates.

While drug eluting stents appear to offer significant promise for treatment of atherosclerosis in many patients, there remain many cases where stents either cannot be used or present significant disadvantages. Generally, stenting leaves an implant in the body. Such implants can present risks, including mechanical fatigue, corrosion, and the like, particularly when removal of the implant is difficult and involves invasive surgery. Stenting may have additional disadvantages for treating diffuse artery disease, for treating bifurcations, for treating areas of the body susceptible to crush, and for treating arteries subject to torsion, elongation, and shortening.

A variety of modified restenosis treatments or restenosis-inhibiting occlusion treatment modalities have also been proposed, including intravascular radiation, cryogenic treatments, ultrasound energy, and the like, often in combination with balloon angioplasty and/or stenting. While these and different approaches show varying degrees of promise for decreasing the subsequent degradation in blood flow following angioplasty and stenting, the trauma initially imposed on the tissues by angioplasty remains problematic.

A number of alternatives to stenting and balloon angioplasty so as to open stenosed arteries have also been proposed. For example, a wide variety of atherectomy devices and techniques have been disclosed and attempted. Despite the disadvantages and limitations of angioplasty and stenting, atherectomy has not gained the widespread use and success rates of dilation-based approaches. More recently, still further disadvantages of dilation have come to light. These include the existence of vulnerable plaque, which can rupture and release materials that may cause myocardial infarction or heart attack.

In light of the above, it would be advantageous to provide new devices, systems, and methods for diagnosing, characterizing, remodeling, and/or removal of atherosclerotic material and occlusions of the lumens of the body, and particularly of the blood vessels. It would further be desirable to avoid significant cost or complexity while providing structures which could both characterize and remodel or remove plaques and other occlusive materials without having to resort to the trauma of dilation, and to allow the opening of blood vessels and other body lumens which are not suitable for stenting. It would also be helpful if diagnosing and treating systems could provide some feedback on the progress of treatment.

BRIEF SUMMARY OF THE INVENTION

The present invention generally provides improved devices, systems, and methods for treating diseased and other target tissues, optionally for treatment of diseases of body lumens. Embodiments of the invention may allow analysis and/or treatment of the materials along these body lumens, optionally allowing plaque and other lesions to be characterized using a variable frequency electrical power or signal source. By radially expanding an electrode array-supporting basket within (for example) a blood vessel, and by monitoring electrical characteristics (and particularly frequency, impedance phase angle, and impedance magnitude) of circuits formed using selected electrodes of the array, plaque, fibrous vulnerable or "hot" plaques, healthy tissues, treated tissues, and/or the like along the blood vessel may be locally analyzed. Optionally, the same electrodes may be used to selectively (and often eccentrically) treat the tissues per the results of the analysis. Tissue signatures may be used to characterize and/or selectively treat tissues with a range of energy modalities, including RF energy, microwave energy, ultrasound energy, light energy, and/or the like.

Embodiments of the invention may employ electrical energy to selectively heat target tissues and/or other structures. For example, circuit frequency and phase angle may be selected to compensate for a phase angle of the target tissue, with the collateral tissues often having a significantly different characteristic phase angle at the selected frequency. More generally, the electrical energy waveforms, application cycles, potentials, delivery systems, and the like may be tailored to help direct therapeutic energy into atheroma and other disease tissues of the vasculature while inhibiting injury to collateral tissue structures. As the electrical characteristics of at least some diseased tissues (and particularly their impedances relative to those of surrounding tissues) may tend to urge known electrosurgical treatment energy into healthy adjacent tissues, such tailoring may improve the efficacy of luminal therapies and/or decrease collateral tissue damage. Exemplary treatment systems and methods for physical targeting (for example, axial and/or radial targeting of occlusive tissues from within a blood vessel) and/or frequency targeting may make use of disease localization information (for example, from intravascular imaging, impedance measurement, or the like) and may optionally employ cooling to protect at least some tissues along a luminal wall.

In a first aspect, the invention provides a method for treating a target tissue in a patient body. The method comprises energizing a circuit with a tissue characterizing energy. Included in the circuit are both the target tissue and a collateral tissue. The target tissue is characterized by measuring an impedance and a phase angle of the circuit while the circuit is energized with the characterization energy. An appropriate form of treatment energy is determined from the measured phase angle of the circuit. The circuit is energized with the treatment energy to treat the target tissue.

Characterization of the target tissue will often include measuring at least one phase angle and impedance magnitude at an associated frequency of the circuit. A number of different frequencies may be used, each frequency having an associated impedance magnitude and phase angle. The set of frequencies, magnitudes, and phase angles can be used to determine if the target tissue is included within the circuit.

The tissues included in the circuit will often be defined at least in part by positioning electrodes of a probe. Exemplary probes described herein may have a number of electrodes, and the energy may be driven in a bipolar manner between selected electrodes of the probe. The probe may also be moved to align the electrodes with the target tissue. Nonetheless, collateral tissues will often be included within the circuit. Hence, driving standard bipolar energy between the electrodes may injure the collateral tissues included within the circuit. In fact, as standard RF energy may tend to (in some cases) preferentially heat the collateral tissues to a greater extent than the target tissues, substantial injury or even necrosis of a significant portion of collateral tissue may result from such standard RF treatments.

So as to enhance the efficacy of RF treatment while inhibiting injury to the collateral tissues included in the circuit, the treatment energy applied to the circuit may have a treatment phase angle which compensates for the phase angle of the target tissue. The phase angle of the treatment energy may be determined based on the measured phase angle of the circuit, and/or on a characteristic phase angle of the target tissue. As both the target tissue and the collateral tissue have impedance magnitudes and phase angles which vary with the frequency of the circuit, and as the energy absorbed by these two different tissues may vary with their phase angles, the treatment energy may be selected so that it has have a frequency at which the target tissue phase angle differs significantly from the collateral tissue phase angle. In other words, the treatment frequency may be selected to, for example, maximize the difference between the phase angle of the target tissue and the phase angle of the treatment tissue. While maximizing the phase angle difference may be beneficial, alternative frequency selecting criteria may also be employed, such as selecting a frequency at which the characteristic phase angles of the target and collateral tissues differ by an amount above a threshold so as to impart sufficient differential heating.

In some embodiments, the target tissue energy may heat the target tissue by a significant multiple of the heating of the collateral tissue. For example, the target tissue may be heated by over 1.5 times the heating of the collateral tissue, in some cases by three times the heating of the collateral tissue. In some embodiments, the target tissue treatment energy may heat the target tissue to a treatment temperature that is at least 2° C. greater than a treatment temperature of the collateral tissue. This may, for example, allow the collateral tissue to remain viable while the target tissue is injured sufficiently for passivation, ablation, or to otherwise render it benign. In some cases, particularly when standard RF energy would tend to heat the collateral tissue to a greater extent than the target tissue, the selected phase angle and frequency may instead cause the target tissue to be raised to a greater temperature than that of the collateral tissue during treatment, or may even simply allow the collateral tissue to be heated to a lesser extent than it would have to be to achieve the same target tissue temperature using standard RF energy.

In another aspect, the invention provides a system for treating a target tissue in a patient body. The system comprises a probe having an electrode for aligning with the target tissue of the patient body. An RF energy source is couplable to the probe. The RF source has a first mode and a second mode. The RF source in the first mode is configured to apply a tissue characterizing energy. The probe, the RF source, the target tissue, and a collateral tissue are included in a circuit when the probe is coupled to the RF source and the electrode is aligned with the target tissue. A processor is coupled to the RF source, and is configured to characterize the tissue by measuring a phase angle of the circuit while the circuit is energized with the characterization energy. The processor is also configured to determine an appropriate treatment energy from the measured phase angle of the circuit for use in the second mode of the RF source. This heats the target tissue and may impede injury to the collateral tissue.

The RF energy source may include separate circuits for generating the characterization energy and the treatment energy, with the source switching between the associated circuits when changing between the first and second modes. In other embodiments, the source may make use of a single hardware system for generating both the characterization energy and the treatment energy.

In a related aspect, the invention provides a catheter system for remodeling and/or reduction of material of or adjacent to a body lumen of a patient. The system comprises an elongate flexible catheter body having a proximal end and a distal end with an axis therebetween. At least one energy delivery surface is disposed near the distal end. A power source is electrically coupled to the energy delivery surface(s). The power source energizes the energy delivery surface(s) with an electrical energy form that helps the energy heat the material and inhibits collateral tissue damage.

In another aspect, the invention provides a method for analyzing a vessel wall of a blood vessel. The method comprises engaging the vessel wall with an electrode of a probe, and energizing the electrode with a variable frequency power source. A frequency of the power source is varied, and a target plaque of the vessel wall is characterized by monitoring a frequency-dependent characteristic of an electrical circuit. The electrical circuit comprises the power source, the electrode, and the engaged vessel wall.

Optionally, the probe expands radially within the blood vessel so as to engage a plurality of electrodes against the vessel wall. The electrodes of the expanded probe generally define a circumferentially distributed electrode array, and the electrodes of the array can be supported by associated struts of the probe. The struts may expand resiliently and independently within the blood vessel so as to couple the array to the vessel wall within non-circular lumens. An eccentric subset of the array (optionally a single electrode or an adjacent pair of electrodes) adjacent the target plaque may be energized to characterize tissues locally, and/or to eccentrically remodel the characterized target plaque using a remodeling electrical potential. Feedback on the remodeling may be obtained by monitoring the characteristic of the electrical circuit while applying an appropriate variable-frequency signal, either during remodeling or by halting remodeling at least temporarily.

In exemplary embodiments, the characterized target plaque may comprise a vulnerable plaque, and the remodeling may be halted in response to the electrical characteristics of the circuit. For example, the remodeling may be halted in response to a change in a tissue signature signal (such as an impedance phase angle and magnitude at a selected frequency or range of frequencies), particularly when the change is associated with heating of lipids of the vulnerable plaque to 85° C. or more. More generally, the target plaque can be characterized using tissue signature and/or tissue signature profiles, with the signature profiles comprising curves or sets of data representing a plurality of tissue signature measurements at different frequencies throughout a frequency range. The target plaque may be characterized by comparison of a measured tissue signature profile to at least one other tissue signature profile, and may allow identification of the measured signature profile as being associated with at least one of healthy tissue, calcified plaque, or vulnerable plaque, with exemplary embodiments able to identify at least two of these. Beneficial embodiments may allow differentiation between plaques and other tissues that have not been treated, have been partially treated, and been appropriately treated, optionally by checking changes of a subset of the tissue signature measurements of the signature profiles (such as at an appropriate frequency or the like).

Many embodiments will be suitable for characterizing a plurality of localized materials distributed axially and/or eccentrically about the blood vessel, and optionally for selectively treating the different characterized materials with different remodeling treatments using the electrodes. Tissue signature profiles may be normalized and/or benchmarked to a known tissue of the patient (such as a healthy tissue identified using intravascular ultrasound or other known techniques), and target plaques may be characterized using relative slopes of tissue signature profiles or offsets between tissue signature profiles (and preferably both). The frequency range of the profiles will often extend below 50 KHz, typically extending from below about 50 KHz to over 1 MHz, and in some embodiments extending from about 4 Hz to about 2 MHz.

In another aspect, the invention provides a system for analyzing a vessel wall of a blood vessel. The system comprises a vascular probe having a proximal end, a distal end, and an electrode disposed near the distal end for engaging the vessel wall. A variable frequency power source can be coupled to the electrode such that, when the electrode engages the vessel wall, an electrical circuit (including the power source, the electrode, and the engaged vessel wall) can be established. A processor is coupled with the variable frequency power source, the processor configured to characterize a target plaque of the vessel wall by monitoring a frequency-dependent characteristic of the electrical circuit.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 38A and 38B show a summary of treatment data of a series of experiments described herein, and total number of treatments within dose ranges, respectively.

DETAILED DESCRIPTION OF THE INVENTION

Figure 1A:
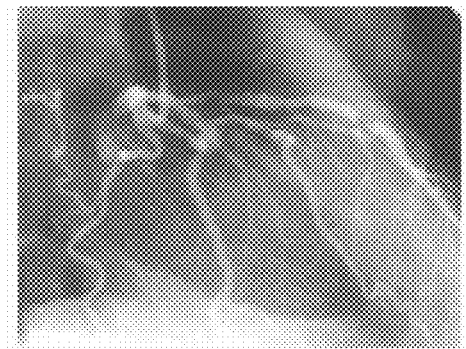
FIG. 1A illustrates diffuse atherosclerotic disease in which a substantial length of multiple blood vessels has limited effective diameters.

The present invention provides devices, systems, and methods to analyze and/or treat a luminal tissue. The invention will be particularly useful for characterizing and remodeling materials along a partially occluded artery in order to open the artery lumen and increase blood flow. Remodeling may involve the application of electrosurgical energy, typically in the form of RF and/or microwave electrical potentials to energy delivery surfaces such as electrodes, antennas, and the like. This energy will optionally be controlled so as to limit a temperature of target and/or collateral tissues, for example, limiting the heating of a fibrous cap of a vulnerable plaque or the intimal layer of an artery structure to a maximum temperature in a range from about 50 to about 60° Celsius. In many embodiments, the energy will be controlled to limit the maximum temperature of an outer layer or adventitia of the blood vessel to no more than about 63° Celsius. Limiting heating of a lipid-rich pool of a vulnerable plaque sufficiently to induce melting of the lipid pool while inhibiting heating of other tissues (such as an intimal layer or fibrous cap) to less than a temperature in a range from about 50 to about 60° Celsius may inhibit an immune response that might otherwise lead to restenosis, or the like. Many embodiments may apply sufficient heat energy to heat the lipids to about 85° Celsius or more while inhibiting collateral damage through selective application of heating energy. Relatively mild heating energies may be sufficient to denature and shrink atherosclerotic material during treatment, immediately after treatment, and/or more than one hour, more than one day, more than one week, or even more than one month after the treatment through a healing response of the tissue to the treatment so as to provide a bigger vessel lumen and improved blood flow.

In some embodiments, remodeling of the atherosclerotic plaque may comprise the use of higher energies to ablate and remove occlusive material from within body lumens, and particularly to remove atherosclerotic material from a blood vessel in order to improve blood flow. Ablation debris may be generated by such ablation, and the ablation debris may be thrombolitic or non-thrombolitic. Where thrombolitic debris is generated by ablation, that debris may be restrained, captured, and/or evacuated from the treatment site. Non-thrombolitic debris produced by ablation may not have to be restrained and/or evacuated from the vessel. The analysis and/or treatment region of the body lumen may be at least partially (or effectively fully) isolated for ablative or other remodeling treatments so as to allow the treatment environment to be modified (for example, by cooling the lumen and/or altering the electrical characteristics of fluid within the lumen using cooled fluid irrigation, non-isotonic fluid irrigation, and/or the like), to limit the release of any remodeling debris, and the like. The techniques of the invention will often provide electrosurgical capabilities, sensing or imaging suitable for measuring atheroma and/or vascular walls, and/or an emboli inhibitor. As atherosclerosis may be eccentric relative to an axis of the blood vessel over 50% of the time, possibly in as much as (or even more than) 75% of cases, the devices and methods of the present invention will often be particularly well suited for directing treatment eccentrically, often in response to circumferential atherosclerotic material detecting or imaging. While the methods and devices described herein allow such eccentric treatments, the devices can also be used for treatment of radially symmetric atherosclerosis by selectively directing energy in a radially symmetric pattern about an axis of the catheter or the like.

Hence, remodeling of atherosclerotic materials may comprise ablation, removal, shrinkage, melting, and the like of atherosclerotic and other plaques. Optionally, atherosclerotic material within the layers of an artery may be denatured so as to improve blood flow, so that debris will not necessarily be generated. Similarly, atherosclerotic materials within the arterial layers may be melted and/or treatment may involve a shrinking of atherosclerotic materials within the artery layers, again without necessarily generating treatment debris. The invention may also provide particular advantages for treatment of vulnerable plaques or blood vessels in which vulnerable plaque is a concern. Such vulnerable plaques may comprise eccentric lesions, and the present invention may be particularly well suited for identifying an orientation (as well as axial location) of the vulnerable plaque structure. The invention will also find applications for targeting the cap structure for mild heating (to induce thickening of the cap and make the plaque less vulnerable to rupture) and/or heating of the lipid-rich pool of the vulnerable plaque (so as to remodel, denature, melt, shrink, and/or redistribute the lipid-rich pool).

While the present invention may be used in combination with stenting and/or balloon dilation, the present invention is particularly well suited for increasing the open diameter of blood vessels in which stenting and balloon angioplasty are not a viable option. Potential applications include treatment of diffuse disease, in which atherosclerosis is spread along a significant length of an artery rather than being localized in one area. The invention may also provide advantages in treatment of vulnerable plaque or blood vessels in which vulnerable plaque is a concern, both by potentially identifying and avoiding treatment of the vulnerable plaque with selected eccentric and/or axial treatments separated from the vulnerable plaque, and by intentionally ablating and aspirating the cap and lipid-rich pool of the vulnerable plaque within a controlled environmental zone or region within the blood vessel lumen. The invention may also find advantageous use for treatment of tortuous, sharply-curved vessels, as no stent need be advanced into or expanded within the sharp bends of many blood vessel. Still further advantageous applications include treatment along bifurcations (where side branch blockage may be an issue) and in the peripheral extremities such as the legs, feet, and arms (where crushing and/or stent fracture failure may be problematic).

Embodiments of the invention may measure impedance of a circuit, and particularly of a circuit that includes an electrode coupled with a luminal wall or other tissue. Such impedance measurements of alternating current (AC) circuits will often include a measurement of both a real portion or magnitude of the impedance, and an imaginary portion or phase angle of the impedance. The impedance magnitude and phase angle generated at an appropriate frequency by a tissue coupled to the electrode may provide a tissue signature. To enhance the accuracy of tissue signature measurements, a plurality of individual measurements (often three or more) may be taken and averaged. By measuring tissue signatures at a plurality of different frequencies (for example, at about 100 different frequencies) within a frequency range, a signature profile for the tissue may be generated, with the signature profiles optionally comprising a curve or curve-fit of phase angles and magnitudes throughout a frequency range. In some embodiments, signal tissue signature measurements may be compared, and/or a smaller number (2-10 or 5-50) of such measurements may be included in a tissue signature profile. Tissue signature measurements may depend on the measurement conditions (including the configuration of the electrodes/tissue coupling), particularly, when the measurements are performed by transmitting bipolar tissue sensing current between two electrodes that are supported by a flexible and/or radially expandable support structure. Nonetheless, the relative tissue signatures and/or signature profiles (particularly the relative offsets between signature profiles, relative slopes of signature profiles, and the like) of different tissues of different patients will often be sufficiently consistent to allow the tissue signatures and signature profiles to be used to distinguish between healthy tissue, calcified plaque, fibrous plaque, lipid-rich plaques, untreated tissue, partially treated tissue, fully treated tissue, and the like.

Optionally, baseline measurements of tissues (which may be characterized via intravascular ultrasound, optical coherence tomography, or the like) may be taken to help differentiate adjacent tissues, as the tissue signatures and/or signature profiles may differ from person to person. Additionally, the tissue signatures and/or signature profile curves may be normalized to facilitate identification of the relevant slopes, offsets, and the like between different tissues. Once sufficient correlations have been established between tissue signatures (including impedance magnitude, phase angle, and frequency) and signature profiles of different tissues for a number of different patients and measurement conditions, tissue characterization of at least some patients may be provided without having to resort to other baseline tissue characterization methodologies.

Figure 1B:
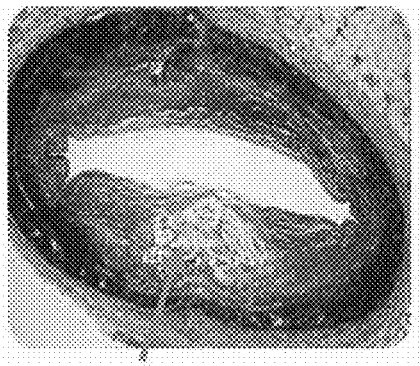
FIG. 1B illustrates vulnerable plaque within a blood vessel.
Figure 1C:
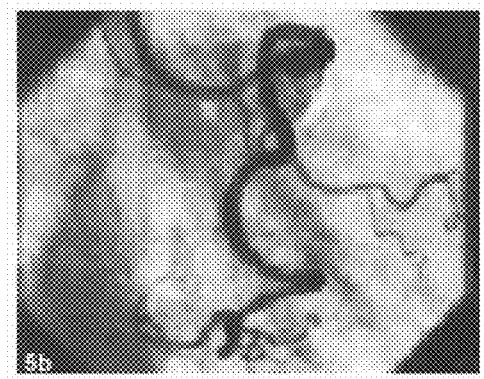
FIG. 1C illustrates the sharp bends or tortuosity of some blood vessels.
Figure 1D:
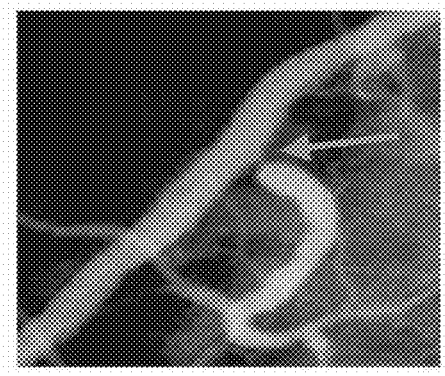
FIG. 1D illustrates atherosclerotic disease at a bifurcation.
Figure 1E:
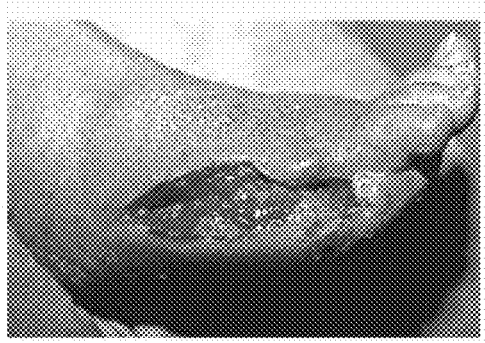
FIG. 1E illustrates a lesion associated with atherosclerotic disease of the extremities.

Diffuse disease and vulnerable plaque are illustrated in FIGS. 1A and 1B, respectively. FIG. 1C illustrates vascular tortuosity. FIG. 1D illustrates atherosclerotic material at a bifurcation, while FIG. 1E illustrates a lesion which can result from atherosclerotic disease of the extremities.

Figure 1F:
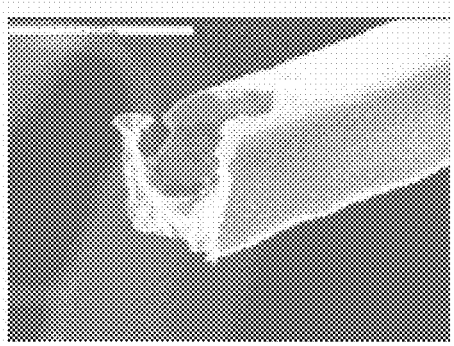
FIG. 1F is an illustration of a stent fracture or corrosion.

FIG. 1F illustrates a stent structural member fracture which may result from corrosion and/or fatigue. Stents may, for example, be designed for a ten-year implant life. As the population of stent recipients lives longer, it becomes increasingly likely that at least some of these stents will remain implanted for times longer than their designed life. As with any metal in a corrosive body environment, material degradation may occur. As the metal weakens from corrosion, the stent may fracture. As metal stents corrode, they may also generate foreign body reaction and byproducts which may irritate adjoining body tissue. Such scar tissue may, for example, result in eventual reclosure or restenosis of the artery.

Figure 1G:
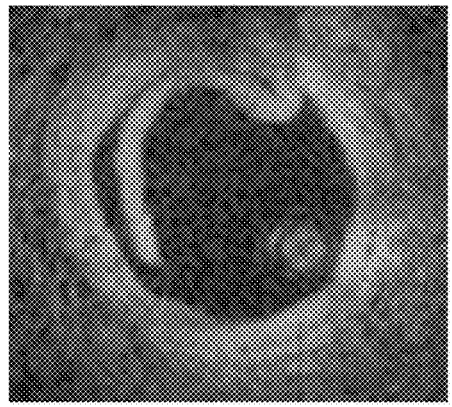
FIG. 1G illustrates a dissection within a blood vessel.
Figure 1H:
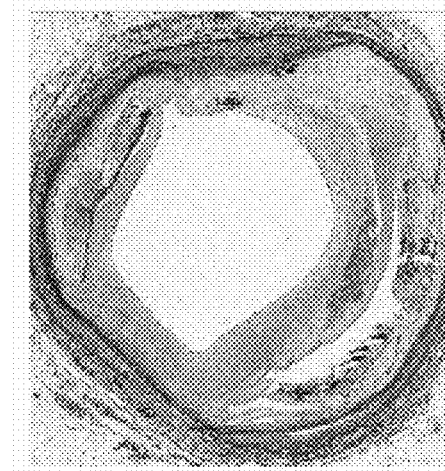
FIG. 1H illustrates a circumferential measurement of an artery wall around a healthy artery.
Figure 1I:
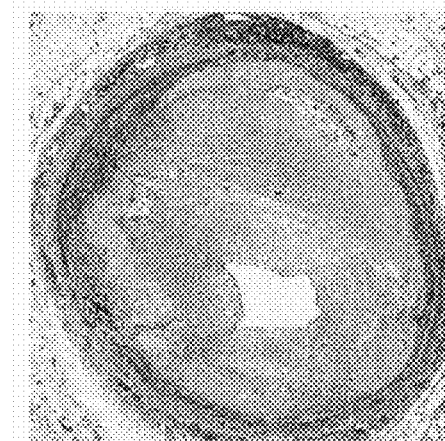
FIG. 1I illustrates circumferential distribution of atheroma about a restenosed artery.

Arterial dissection and restenosis may be understood with reference to FIGS. 1G through 1I. The artery comprises three layers, an endothelial layer, a medial layer, and an adventitial layer. During angioplasty, the inside layer may delaminate or detach partially from the wall so as to form a dissection as illustrated in FIG. 1G. Such dissections divert and may obstruct blood flow. As can be understood by comparing FIGS. 1H and 1I, angioplasty is a relatively aggressive procedure which may injure the tissue of the blood vessel. In response to this injury, in response to the presence of a stent, and/or in the continuing progression of the original atherosclerotic disease, the opened artery may restenose or subsequently decrease in diameter as illustrated in FIG. 1I. While drug eluting stents have been shown to reduce restenosis, the efficacy of these new structures several years after implantation has not be fully studied, and such drug eluting stents are not applicable in many blood vessels.

In general, the present invention provides a catheter which is relatively quick and easy to use by the physician. The catheter system of the present invention may allow arteries to be opened to at least 85% of their nominal or native artery diameter. In some embodiments, arteries may be opened to about 85%, and/or acute openings may be less than 85%. Rapid occlusive material removal may be effected using sufficient power to heat tissues locally to over about 100° C. so as to vaporize tissues, or more gentle remodeling may be employed.

The desired opening diameters may be achieved immediately after treatment by the catheter system in some embodiments. Alternatively, a milder ablation may be implemented, for example, providing to no more than a 50% native diameter when treatment is complete, but may still provide as much as 80 or even 85% or more native vessel open diameters after a subsequent healing process is complete, due to resorption of injured luminal tissues in a manner analogous to left ventricular ablation for arrhythmia and transurethral prostate treatments. Such embodiments may heat at least some occlusive tissue to a temperature in a range from about 55° C. to about 80° C. In some embodiments, occlusive tissues may be heated to a maximum temperature in a range between about 93 and 95° C. In other embodiments described herein, heating may be controlled so as to provide tissue temperatures in a range between about 50 and 60° C., with some embodiments benefiting from maximum tissue temperatures of about 63° C. Still further treatments may benefit from treatment temperatures of about 90° C. Advantageously, the catheter systems and methods of the invention may be used without balloon angioplasty, thereby avoiding dissections and potentially limiting restenosis. Optionally, treatments of tissues described herein may be repeated during a single surgical session, or after a month or more (even after a year or more) if appropriate to provide or maintain a desired opening of the lumen.

Figure 2:
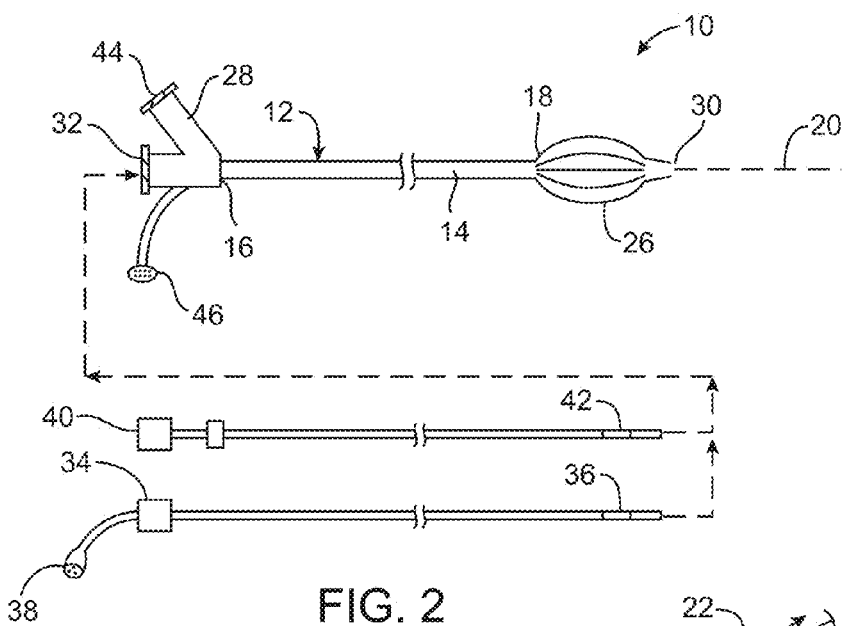
FIG. 2 schematically illustrates an atherosclerotic material catheter system according to the present invention.
Figure 3:
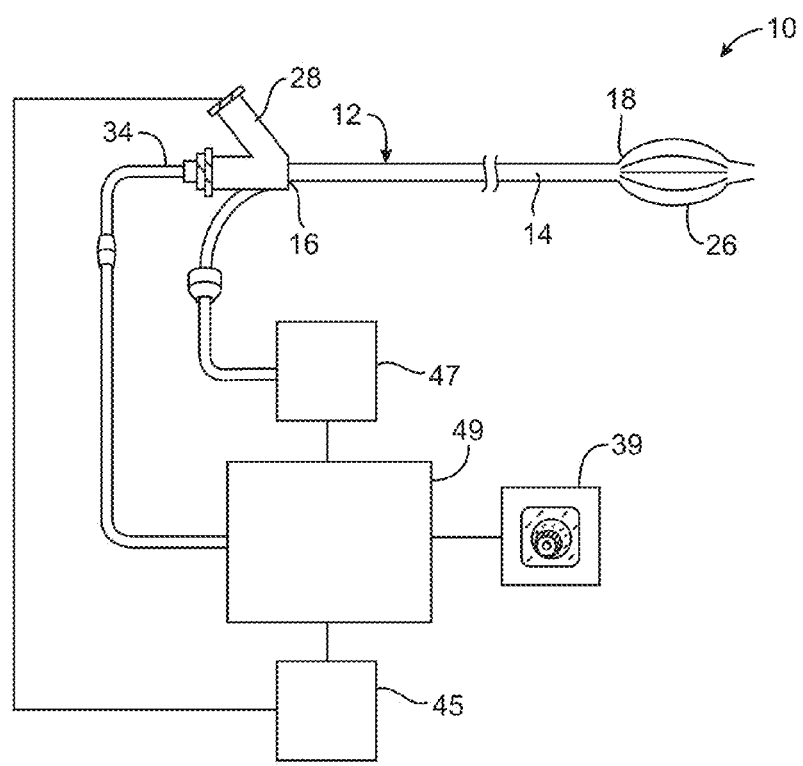
FIG. 3 schematically illustrates a catheter system for remodeling atherosclerotic material, the system including the catheter of FIG. 2.

An exemplary catheter system 10 is schematically illustrated in FIGS. 2 and 3. A remodeling and/or ablation catheter 12 includes a catheter body 14 having a proximal end 16 and a distal end 18. Catheter body 14 is flexible and defines a catheter axis 20, and includes an aspiration lumen 22 and an irrigation lumen 24 (see FIG. 3). Still further lumens may be provided for a guidewire, imaging system, or the like as described below. Lumen 22 may be used for sensing and/or imaging of atheroma as well as aspiration.

Catheter 12 includes a radially expandable structure 26 adjacent distal end 18 and a housing 28 adjacent proximal end 16. A distal tip 30 may include an integral tip valve to seal aspiration lumen 22 and allow passage of guidewires, imaging and/or restenosis inhibiting catheters, and the like.

Proximal housing 28 includes a first connector 32 in fluid communication with aspiration lumen 22. Aspiration lumen 22 may have an aspiration port within expandable structure 26 so as to allow aspiration or aspiration of debris and gasses from within the expandable structure. Aspiration lumen 22 may also be used as an access lumen for guidewires, intravascular imaging catheters, and/or distally advancing intravascular radiation treatment catheters or restenosis inhibiting drugs. Hence, connector 32 may selectively accommodate an imaging catheter 34 having an atherosclerotic material detector 36 advancable within catheter body 14 adjacent to and/or beyond distal end 18, the detector often comprising an intravascular ultrasound transducer, an optical coherent tomography sensor, an MRI antenna, or the like. An imaging connector 38 of imaging catheter 34 transmits imaging signals allowing circumferential measurement of atherosclerotic thicknesses about axis 20 to a display 39.

Connector 32 also accommodates a restenosis inhibiting treatment catheter 40, the treatment catheter here comprising an intravascular radiation catheter. Such a radiation catheter may include a radiation source 42 which can again be advanced distally within catheter body 14 to or beyond expandable structure 26.

Figure 4:
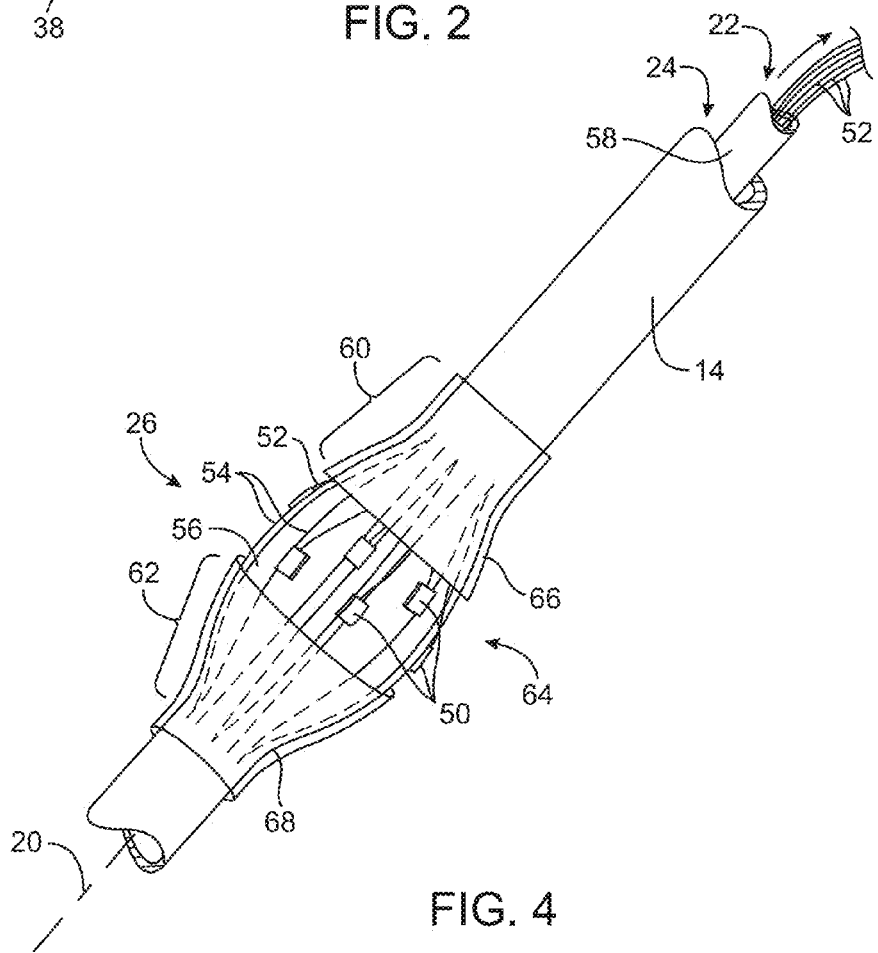
FIG. 4 illustrates an expandable basket and an associated electrode array of the catheter system of FIG. 2.

A second connector 44 of proximal housing 28 is in fluid communication with irrigation lumen 24 (see FIG. 4). Second connector 44 may be coupled to an irrigation fluid source for introducing conductive or non-conductive liquids, gases, or the like, ideally for introducing gas or heparinized saline. Both first and second connectors 32, 44 may optionally comprise a standard connector such as a Luer-Loc™ connector. In FIG. 3 connector 44 is schematically shown coupled to an aspiration vacuum source/infusion fluid source 45.

Referring now to FIGS. 2, 3, and 4, proximal housing 28 also accommodates an electrical connector 46. Connector 46 includes a plurality of electrical connections, each electrically coupled to an electrode 50 via a dedicated conductor 52. This allows a subset of electrodes 50 to be easily energized, the electrodes often being energized with bipolar or monopolar RF energy. Hence, electrical connector 46 will often be coupled to an RF generator via a controller 47, with the controller allowing energy to be selectively directed to an eccentric portion of an engaged luminal wall. When monopolar RF energy is employed, patient ground may (for example) be provided by an external electrode or an electrode on catheter body 14. A processor 49 may manipulate signals from imaging catheter 34 to generate an image on display 39, may coordinate aspiration, irrigation, and/or treatment, and may automatically register the treatment with the image.

Processor 49 will typically comprise computer hardware and/or software, often including one or more programmable processor unit running machine readable program instructions or code for implementing some or all of one or more of the methods described herein. The code will often be embodied in a tangible media such as a memory (optionally a read only memory, a random access memory, a non-volatile memory, or the like) and/or a recording media (such as a floppy disk, a hard drive, a CD, a DVD, a memory stick, or the like). The code and/or associated data and signals may also be transmitted to or from the processor via a network connection (such as a wireless network, an Ethernet, an internet, an intranet, or the like), and some or all of the code may also be transmitted between components of catheter system 10 and within processor 49 via one or more bus, and appropriate standard or proprietary communications cards, connectors, cables, and the like will often be included in the processor. Processor 49 will often be configured to perform the calculations and signal transmission steps described herein at least in part by programming the processor with the software code, which may be written as a single program, a series of separate subroutines or related programs, or the like. The processor may comprise standard or proprietary digital and/or analog signal processing hardware, software, and/or firmware, and will typically have sufficient processing power to perform the calculations described herein during treatment of the patient, the processor optionally comprising a personal computer, a notebook computer, a tablet computer, a proprietary processing unit, or a combination thereof. Standard or proprietary input devices (such as a mouse, keyboard, touchscreen, joystick, etc.) and output devices (such as a printer, speakers, display, etc.) associated with modern computer systems may also be included, and processors having a plurality of processing units (or even separate computers) may be employed in a wide range of centralized or distributed data processing architectures.

Expandable structure 26 is illustrated in more detail in FIG. 4. Expandable structure 26 may expand resiliently when released from within a restraining sheath, or may expand by pulling tip 30 toward distal end 18 (see FIG. 2), optionally using a pullwire, an inner catheter body 58, or the like. Expandable structure 26 here comprises a perforate structure or basket having a series of structural struts or elements 54 with opening or perforations 56 therebetween. Perforations 56 may be formed, for example, by cutting elongate slits in a flexible tube material, or the basket may be formed by braiding elongate wires or ribbons or the like.

Expandable structure 26 generally includes a proximal portion 60, a distal portion 62, and an intermediate portion 64 therebetween. Each electrode 50 is mounted on an associated basket element 54 along intermediate portion 64, with an associated conductor 52 extending proximally from the electrode. Electrodes 50 are distributed circumferentially about axis 20 in an array, adjacent electrodes preferably being axially offset, ideally being staggered or alternating between proximal and distal axial locations. This allows bipolar energy to be directed between adjacent circumferential (axially offset) electrodes, between adjacent distal electrodes, between adjacent proximal electrodes, and the like.

In the exemplary embodiment, proximal and distal barriers 66, 68 expand radially with proximal and distal portions 60, 62 of expandable structure 26. Barriers 66, 68 inhibit any ablation debris and gases generated adjacent electrodes 50 from traveling within the body lumen beyond catheter 12. Barriers 66, 68 also allow an at least partially isolated ablation environment to be established within the body lumen, for example, by replacing blood within a blood vessel with a more advantageous fluid environment for limiting charring of the electrodes and the like. Alternative barriers may be provided instead of (or in combination with) barriers 66, 68, including one or more balloons axially offset from expandable member 26, elastic lips, or the like. In other embodiments remodeling may be effected without generating significant thermolytic ablation debris and/or a desired treatment environment may be provided with localized irrigation and/or aspiration flows so that some systems may forego the use of barriers.

Figure 5:
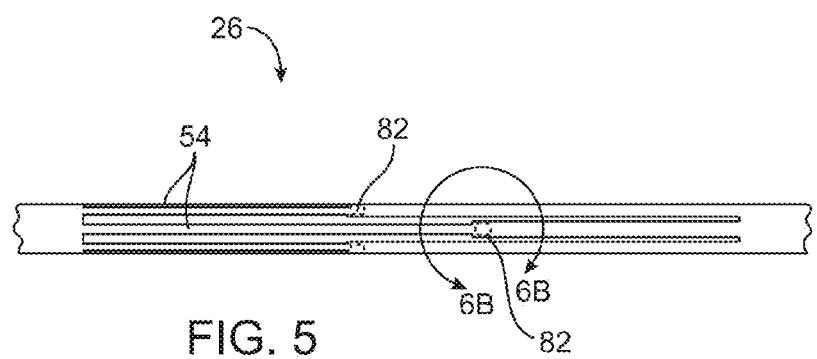
FIGS. 5 and 6 illustrate an exemplary basket structure having alternating axially offset electrodes in a circumferential array.
Figure 6:
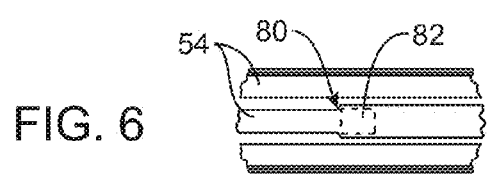

Exemplary expandable structure 26 is formed by cutting slots in a superelastic alloy tube such as a nickel titanium alloy or Nitinol™ tube. As can be understood with reference to FIG. 6, expandable structures 54 may have circumferential widths 80 which are enhanced adjacent an electrode and/or electrode mounting location 82. As can be seen in FIG. 5, the localized enhancement of the width 80 adjacent electrode mounting pads 82 may be axially offset, as described above. The slots forming expandable members 54, and hence the expandable members themselves may, for example, be 0.8 inches in length, with the expandable members having a circumferential width of about 0.25 inches. A variety of alternative expandable structures might also be used, with suitable expandable structures often being expandable from a low profile configuration for intravascular insertion and positioning to an expanded configuration in which radially outwardly oriented electrodes supported by the expandable structure can engage a surrounding vessel wall. Suitable alternative expandable structures may, for example, comprise compliant or non-compliant balloons similar to or modified from those used in any of a variety of balloon catheter structures. Exemplary balloon expandable structures may comprise a compliant balloon having helical folds to facilitate reconfiguring the balloon from a radially expanded, inflated configuration to a low profile configuration, particularly for removal after use.

Figure 7A:
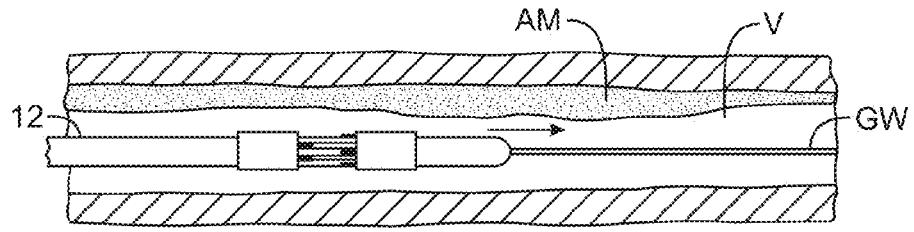
FIGS. 7A-E illustrate an exemplary atherosclerotic material remodeling and/or removal method using the catheter system of FIG. 2.

The use of catheter system 10 for remodeling and/or removal of eccentric atheroma from within a blood vessel can be understood with reference to FIGS. 7A through 7E. As seen in FIG. 7A, accessing of a treatment site will often involve advancing a guidewire GW within a blood vessel V at, and more often distally beyond a target region of atherosclerotic material AM. A wide variety of guidewires may be used. For accessing a vessel having a total occlusion, guidewire GW may comprise any commercially available guidewire suitable for crossing such a total occlusion, including the Safe-Cross™ RF system guidewire having forward-looking optical coherence reflectrometry and RF ablation. Where atherosclerotic material AM does not result in total occlusion of the lumen, such capabilities need not be provided in guidewire GW, although other advantageous features may be provided. For example, guidewire GW may include a distal balloon to hold the guidewire in place and further inhibit movement of ablation debris and the like. Guidewire GW may be positioned under fluoroscopic (or other) imaging.

Figure 7B:
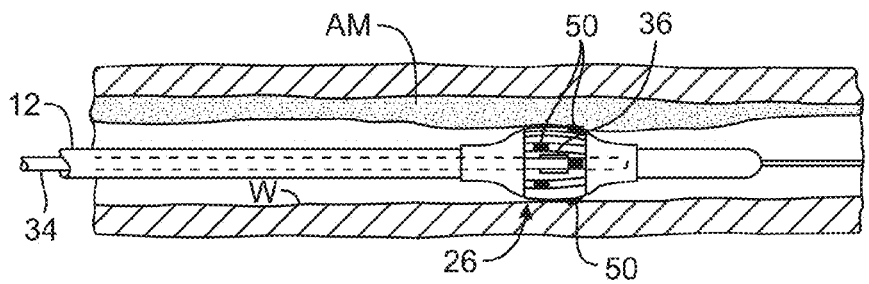

Catheter 12 is advanced distally over guidewire GW and positioned adjacent to atherosclerotic material AM, often toward a distal portion of the occlusion as can be understood with reference to FIGS. 7A and 7B. Expandable structure 26 expands radially within the lumen of the blood vessel so that electrodes 50 radially engage atherosclerotic material AM. Expandable structure 26 may be expanded by, for example, pulling a pullwire extending through catheter body 14 to the coupled (directly or indirectly) to distal portion 62 of expandable body 26 (see FIG. 4). Alternatively, an inner catheter body 58 may be moved proximally relative to outer catheter body 14, with the inner catheter again being coupled to the distal portion of the expandable body. Still further alternatives are possible, including withdrawing a sheath from around the expandable body and allowing the expandable body to flex radially outwardly. In at least some embodiments, whether actuated from the proximal end of catheter 12 or simply by releasing the expandable body, the structural members defining the expandable body may comprise elastic or superelastic materials treated to expand radially outwardly, such as by heat-setting a superelastic Nitinol™ metal, polyimide, or the like. In some embodiments, guidewire GW may be removed after the ablation catheter is positioned and/or the basket is expanded. As atherosclerotic material AM is distributed eccentrically about catheter 12, some of electrodes 50 directly engage a luminal wall W, as can be understood with reference to FIGS. 7B and 7C.

Figure 7C:
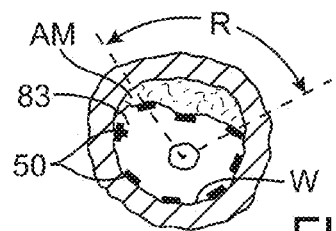

Imaging catheter 34 is positioned within a lumen of catheter 12 so that detector 42 extends to adjacent atherosclerotic material AM. The imaging catheter operates within and/or through catheter 12 so as to measure a thickness of atherosclerotic material concentrically about catheter 12 as illustrated in FIG. 7C with measurements often being taken at a plurality of axial locations so as to measure axial variation of the atherosclerotic material AM within the blood vessel, such measurements often progressing proximally. In many cases, atherosclerotic material AM will be distributed eccentrically within the vessel wall as shown in FIG. 7C. It should be noted that no portion of the vessel wall need be completely uncovered by atherosclerotic material for the measurement distribution to indicate that the obstruction is eccentric, as a relatively thin layer of atheroma along one portion or side of the blood vessel may be much different in thickness than a very thick layer of atherosclerotic material on an opposite side of the blood vessel V. In some methods, remodeling and/or ablation of all atheroma along one side may result in electrode/vessel wall engagement only after treatment begins.

In some cases, imaging catheter 34 may allow identification and/or characterization of atherosclerotic materials, plaques, tissues, lesions, and the like from within a blood vessel. For example, imaging catheter 34 may determine an axial and/or circumferential localization of a target plaque for treatment. Where treatments are intended for atherosclerotic plaques so as to enhance blood flow through the lumen, the treatment may be tailored to provide short term and/or long term increases in lumen diameter and blood flow. Where catheter 34 identifies a circumferentially and/or axially localized vulnerable plaque, that vulnerable plaque may be targeted for a suitable treatment to inhibit deleterious release of thrombolitic materials, often by thickening a fibrous cap of the vulnerable plaque, making the plaque less vulnerable to rupture, decreasing a size or danger of release from a lipid-rich pool of the vulnerable plaque, or the like. Hence, catheter 34 may be used to provide information similar to that available through histology so as to indicate a composition of an atheroma (by identifying and location, for example, a fibrous cap, smooth muscle cells, a lipid pool, calcifications, and the like.) Intravascular ultrasound catheters may now be capable of such atheroma characterizations, and these characterizations may also be provided by optical coherence tomography intravascular catheters, intravascular MRI antennas, and other catheter-based imaging systems, or by non-invasive imaging modalities such as MRI systems, and the like.

Suitable imaging catheters for use in the present catheter system are commercially available from a wide variety of manufacturers. Suitable technology and/or catheters may, for example, be commercially available from SciMed Life Systems and Jomed-Volcano Therapeutics (providers of intravascular ultrasound catheters), Light Lab™ Imaging (developing and commercializing optical coherence tomography catheters for intravascular imaging), Medtronic Cardio-Rhythm, and the like. Still further alternative technologies may be used, including ultra fast magnetic resonance imaging (MRI), electrical impedance atheroma depth measurements, optical coherence reflectometry, and the like.

The systems, devices, and methods described herein may optionally make use of imaging techniques and/or atherosclerotic material detector devices which are at least in part (optionally being entirely) disposed outside of the body lumen, optionally being disposed outside of the patient body. Non-invasive imaging modalities which may be employed include X-ray or fluoroscopy systems, MRI systems, external ultrasound transducers, and the like. Optionally, external and/or intravascular atherosclerotic material detectors may also be used to provide temperature information. For example, a system having an MRI antenna may detect tissue temperatures such that a graphical indication of treatment penetration may be presented on the system display. Tissue temperature information may also be available from ultrasound and/or optical coherence tomography systems, and the temperature information may be used as feedback for directing ongoing treatments, for selecting tissues for treatment (for example, by identifying a hot or vulnerable plaque), and the like.

As with positioning of guidewire GW and advancement of catheter 12, positioning of sensor 36 of imaging catheter 34 may be facilitated by fluoroscopic or other imaging modalities. Location of sensor 36 relative to expandable structure 26 may be facilitated by radiopaque markers of catheter 34 adjacent sensor 36, and by the radiopaque structure (or corresponding radiopaque markers placed on or near) expandable structure 26, and/or by the use of radiopaque electrodes.

By expanding expandable structure 26 within blood vessel V, optional proximal and distal barriers 66, 68 (see FIG. 4) may form an at least partially, and preferably a substantially isolated environment within the blood vessel. That environment may be adapted to improve subsequent remodeling and/or ablation by aspirating blood from a port of aspiration lumen 22 disposed between proximal and distal barriers 66, 68, and by irrigating the isolated environment with a desired fluid, as described above. When provided, aspiration and/or irrigation may be performed, optionally simultaneously, so as to generate a flow within the controlled environment for removal of any vaporization gases, ablation debris, and the like.

Figure 7D:
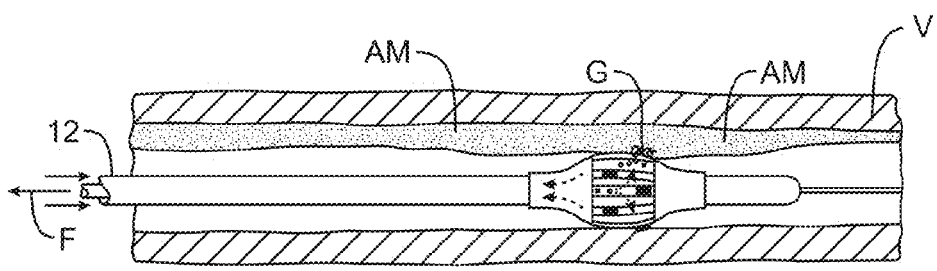

Referring now to FIGS. 7C and 7D, circumferential imaging often indicates that remodeling and/or ablation should be targeted to an eccentric portion or region R of the vessel wall W. To aid in registering the electrodes with the circumferential atheroma distribution, one strut of expandable structure 26 has an identifiable image, allowing the strut to serve as a rotational alignment key. Registering the electrodes may be achieved using intravascular imaging such as intravascular ultrasound (IVUS), optical coherence tomography ("OCT"), intravascular MRI, and/or the like, optionally using external imaging such as fluoroscopy, magnetic resonance imaging ("MRI"), or the like. Electronic registration may also be used. In response to this information, RF energy is directed to electrodes within region R. These actively energized electrodes define a subset of the overall array of electrodes, and selection of this subset of electrodes may be implemented using a controller as described hereinbelow.

The mechanisms of ablating atherosclerotic material within a blood vessel have been well described, including by Slager et al. in an article entitled, *"Vaporization of Atherosclerotic Plaque by Spark Erosion"* in *J. of Amer. Cardiol.* (June, 1985), on pp. 1382-6; and by Stephen M. Fry in *"Thermal and Disruptive Angioplasty: a Physician's Guide;"* Strategic Business Development, Inc., (1990) the full disclosures of which are incorporated herein by reference. Suitable vaporization methods and devices for adaptation and/or use in the present system may also be described in U.S. Pat. Nos. 5,098,431; 5,749,914; 5,454,809; 4,682,596; and 6,582,423, among other references. The full disclosure of each of these references is incorporated herein by reference.

Figure 7E:
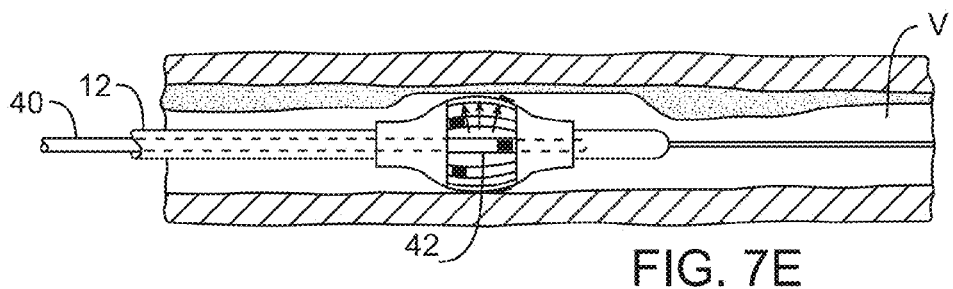

Referring now to FIG. 7E, as described above, it may not be necessary to completely remove all atheroma or atherosclerotic material from within the blood vessel. Providing an open lumen having an effective diameter of at least 80 or 85% of a nominal native lumen diameter may be sufficient. Remodeling treatments may provide acute effective open diameters in a range from about 30% to about 50%. In some embodiments, injury caused to the atherosclerotic material with the energized electrodes or other energy directing surfaces may result in subsequent resorption of the injured tissue lesions so as to provide further opening of the vessel after termination of treatment as part of the healing process.

To promote long term efficacy and inhibit restenosis of a treated region of blood vessel V, a restenosis inhibiting catheter 40 may be advanced through a lumen of catheter 12, so that a radiation source 42 irradiates the treated region of the blood vessel. Suitable intravascular radiation catheters are commercially available from Novoste™, Guidant, Johnson & Johnson, and the like. Restenosis inhibiting drugs similar to those now being employed on drug eluting stents may also be advanced through a lumen of catheter 12, optionally while the proximal and distal barriers again help to maintain a controlled environmental zone within the blood vessel, so that systemic drug delivery might be limited or avoided. In addition to known restenosis inhibiting drugs used on drug eluting stents, drugs which cause vasodilation might be employed. Known restenosis inhibiting drugs such as Rapamycin™ may also be used.

In some embodiments, expandable structure 26 may remain expanded against the vessel wall W and/or atherosclerotic material AM while catheter 12 moves within the blood vessel, the catheter often being drawn proximally during or between ablation treatments. Analogous movement of a radially expanded perforate basket is employed, for example, when measuring temperatures of blood vessels so as to detect vulnerable plaque in systems now being developed and/or commercialized by Volcano Therapeutics. Alternatively, the basket may be repeatedly contracted, axial movement of the catheter 12 employed to reposition the basket, with subsequent expansion of the basket at each of a plurality of treatment locations along atherosclerotic material AM. Repeated intravascular imaging or other atherosclerotic material thickness measurements circumferentially about catheter 12 may be employed, with the remodeling and/or ablation often being halted temporarily so as to allow an image to be acquired intermittently during an ablation procedure. A final image may be taken to verify remodeling and/or ablation has been successful.

Figure 8:
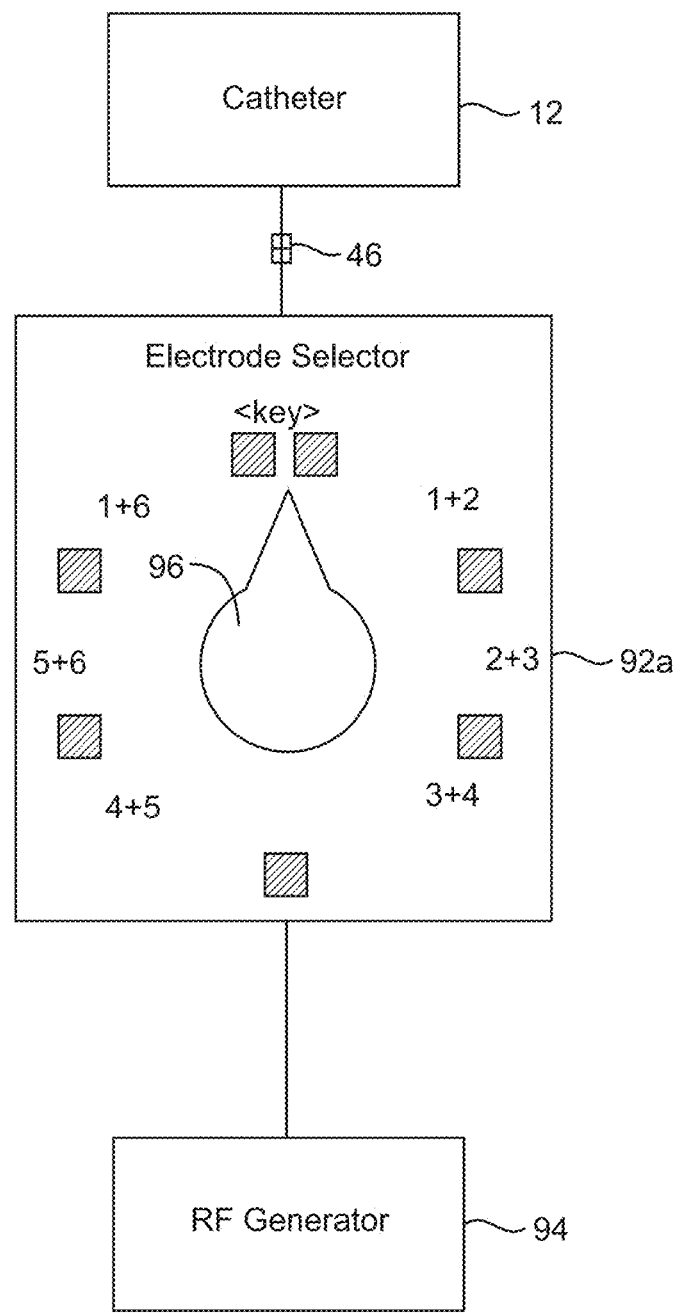
FIGS. 8-10 schematically illustrate controllers for selectively energizing electrodes in the system of FIG. 2.
Figure 9:
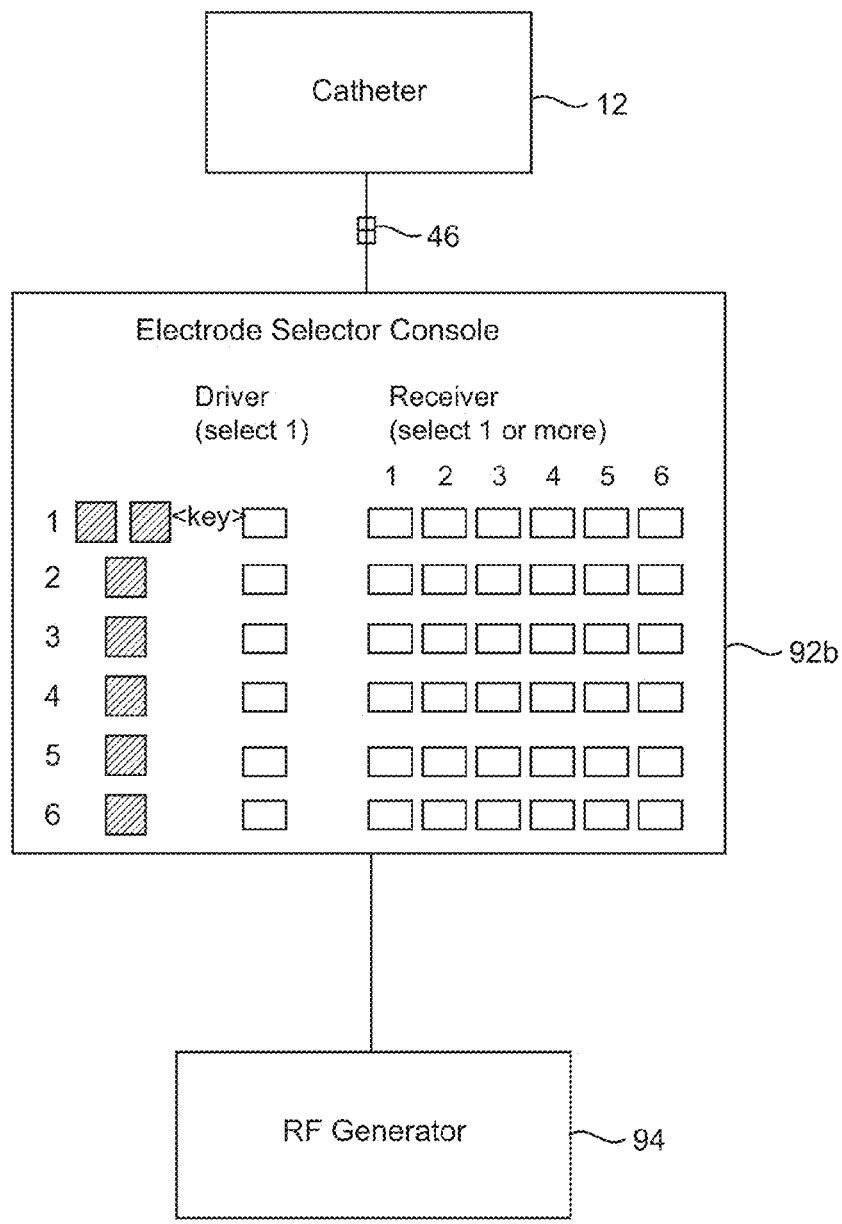
Figure 10:
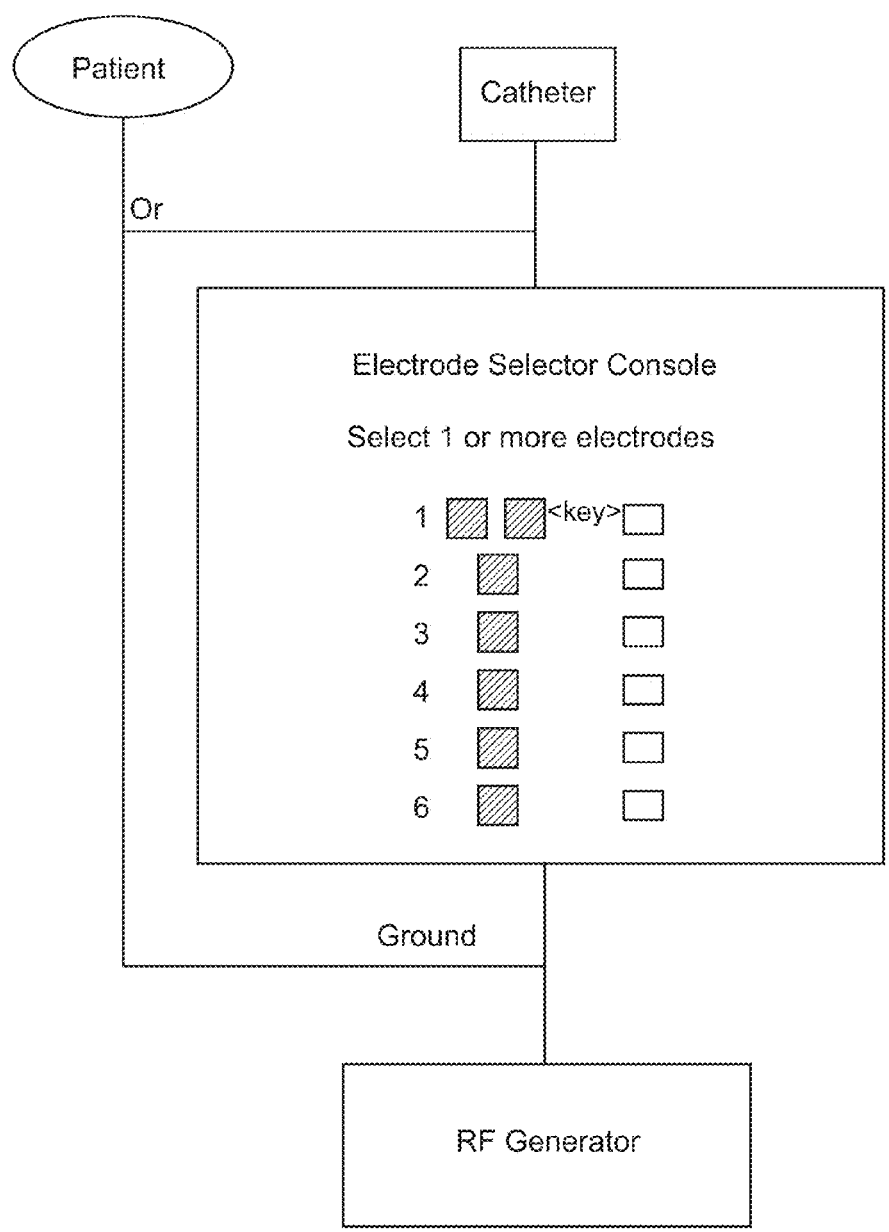

Referring now to FIGS. 8 and 9, alternative controllers 92a, 92b selectively energize electrodes of catheter 12 with RF power supplied from an RF generator 94. A wide range of RF energy types may be employed, including burst of 500 Khz, different types of waveforms, and the like. In controller 92a, a simple dial 96 is turned to point to a desired electrode pair to be energized. A "key" electrode may be registered with the intravascular imaging system, either electronically or by providing an electrode, electrode support member, or attached marker which presents a distinct image on the intravascular imaging display. This simplifies selection of one or more eccentric electrode pair along atheroma. Advantageously, catheter 12 need not be rotated into a proper orientation to accurately remodel and/or ablate the desired eccentric atherosclerotic material. Controller 92b includes similar capabilities, but allows the operator to select multiple electrodes for driving bipolar RF energy therebetween, providing greater flexibility in allowing multiple electrodes to be simultaneously energized. Monopole control arrangements similar to those of FIGS. 8 and 9 may also be employed, as can be understood with reference to FIG. 10. Patient grounding may be effected by a patient grounding plate, a ring electrode 2 to 5 cm proximal to basket 26, or the like. Once again, no catheter rotation is required to orient an active side of the catheter adjacent to the targeted atheroma since various eccentric ablation orientations can be selected through the electrode selection controller.

Figure 11:
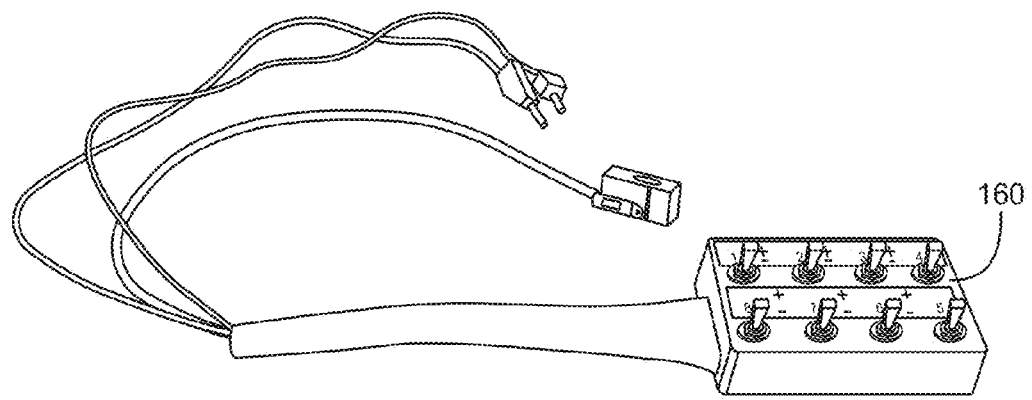
FIG. 11 illustrates an alternative controller for selectively energizing electrodes in the system of FIG. 2.

An alternative controller 160 is illustrated in FIG. 11. This controller allows an operator to choose, for each electrode, whether to keep that electrode inactive, electrically couple that electrode to a first pole (sometimes referred to as pole A) of an energy source (such as an RF generator or the like), or to electrically couple that electrode to a second pole or pole B of the energy source. This controller allows a wide range of energized electrode configurations, including pseudo-monopolar modes where all electrodes except one are connected to one pole of the energy source (pole A) and one electrode is connected to the other pole (pole B). Each electrode (in this embodiment, up to eight electrodes) is electrically coupled to a 3-way switch numbered from 1 to 8. A switch disposed in the middle position indicates the electrode is not coupled to either pole, while a switch pushed toward the plus sign indicates the associated electrode is coupled to a red RF connector with the controller. Similarly, a switch pushed toward the minus sign indicates the associated electrode is electrically coupled to a black RF connector of the control box.

Figure 12A:
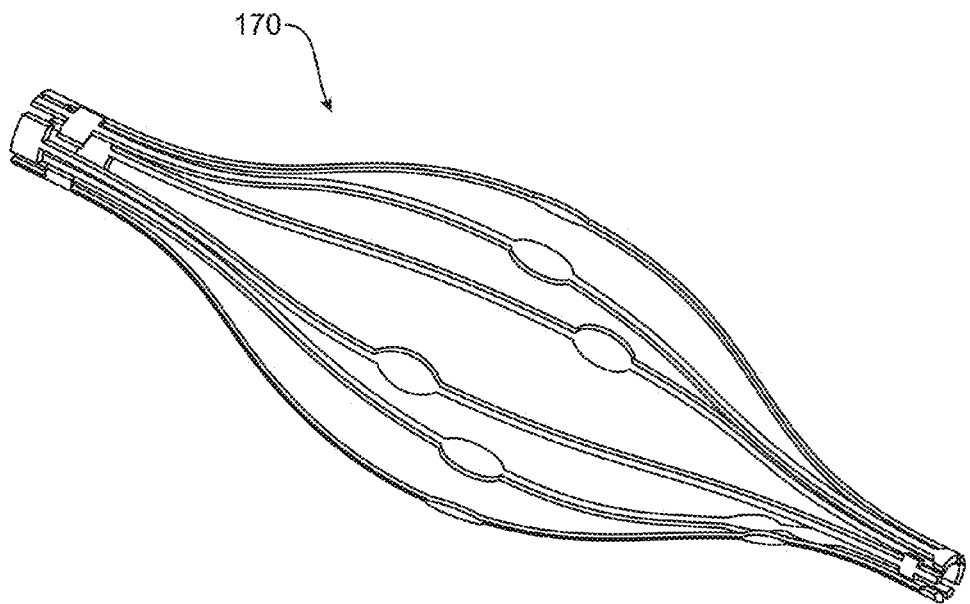
FIGS. 12A-12H illustrate an alternative basket structure formed with independent struts having a localized enhanced width for use as an electrode surface, along with components thereof.
Figure 12B:
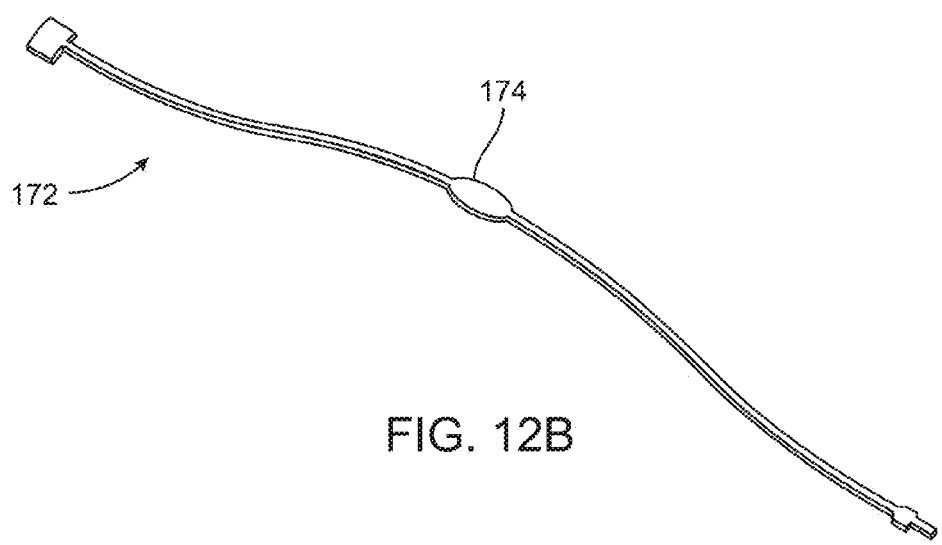
Figure 12C:
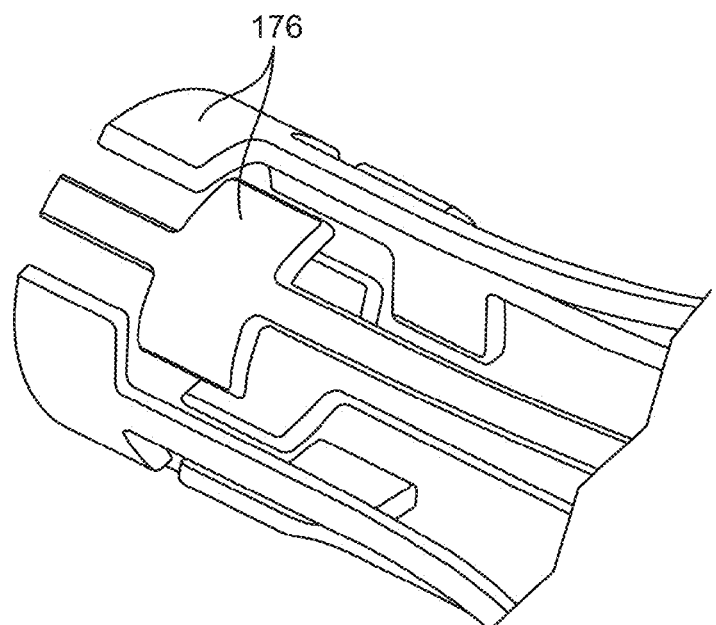
Figure 12D:
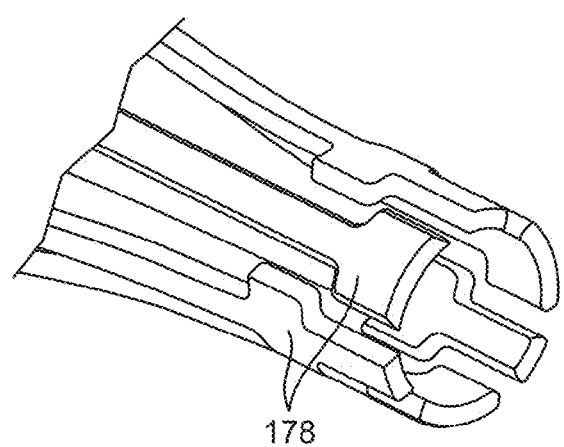
Figure 12E:
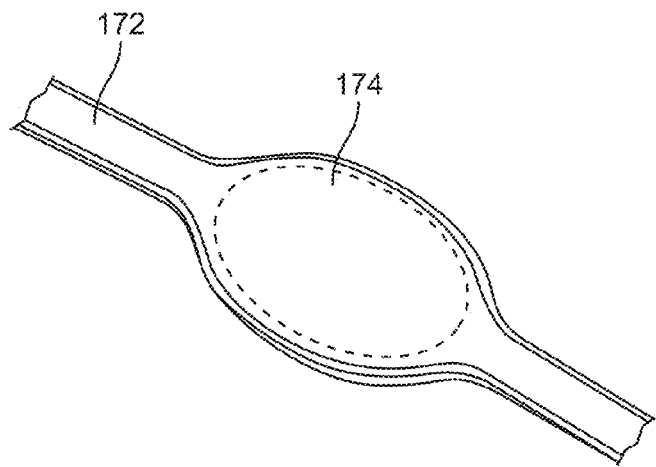

An exemplary self-expandable basket is illustrated in FIGS. 12A-12H. As can be understood from these drawings, electrodes may be fabricated as part of the struts 172 from which the basket is formed, for example, using a radially outwardly oriented surface of a localized widening 174 of each strut disposed in axially central portion of the strut, as can be seen in FIGS. 12B and 12E. Each arm may be formed from one piece of material, optionally comprising a Nitinol™ nickel-titanium shaped memory alloy, with the struts optionally being laser cut from a Nitinol™ tube. The electrode/basket may be, for example, coated with a high temperature polymer such as a polyimide. Electrodes 174 may be formed by inhibiting coating or removing coating from the desired portion of the associated strut 172 (as illustrated in FIG. 12E) so that the electrode surface is exposed for contact with atherosclerotic material. At least the active electrode surfaces may be coated with a highly conductive metal such as gold, silver, an alloy of copper, or the like, and the coating will preferably maintain and withstand flexibility of the basket structure, with coating materials optionally being rolled or the like. By limiting the conductive electrode to a properly configured (often radially outwardly oriented), electrical coupling between the electrode and blood or other conductive fluids within the lumen may be limited. The struts may be separated from each other and structurally supported with an insulated material such as ultraviolet ("UV") cure or heat shrink sleeve, a polyethylene, Nylon™, or the like to form basket 170.

Each strut 172 may be used to conduct energy between electrode surface 174 and an electrical conductor extending proximally from the strut toward a controller. Proximal pads for connecting such conductors are illustrated in FIG. 12C, while distal structural pads 178 are illustrated in FIG. 12D.

Figure 12F:
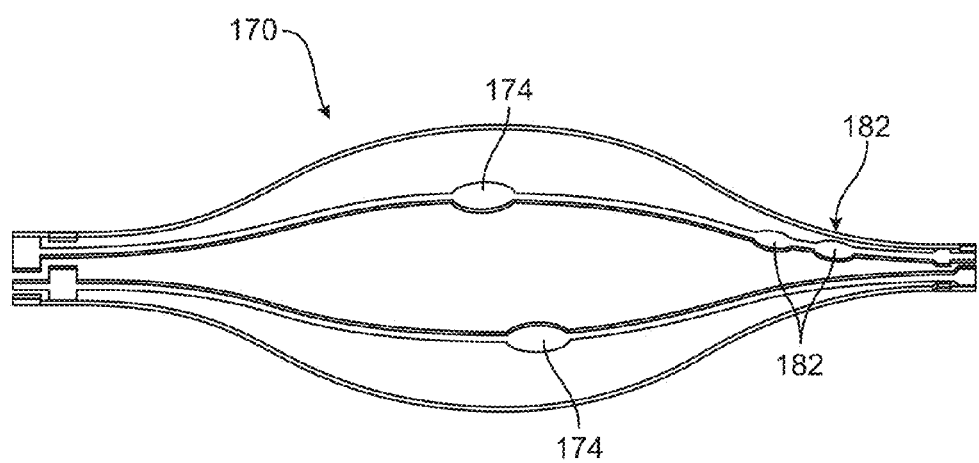

Adjacent electrodes 174 may be axially offset or staggered as can be seen in FIG. 12F. Insulating coating along each strut 172 may be inhibited or removed from an inner surface of proximal pads 176 so as to facilitate connecting of an associated conductive wire, such as by spot welding or the like. Alternative polymer or non-polymer insulating materials may also be used, including parylene coatings, while alternative methods for attaching struts 172 to a catheter body may be employed, including adhesive bonding using insulating UV cure, embedding the pad structures in polyethylene, and the like.

Figure 12G:
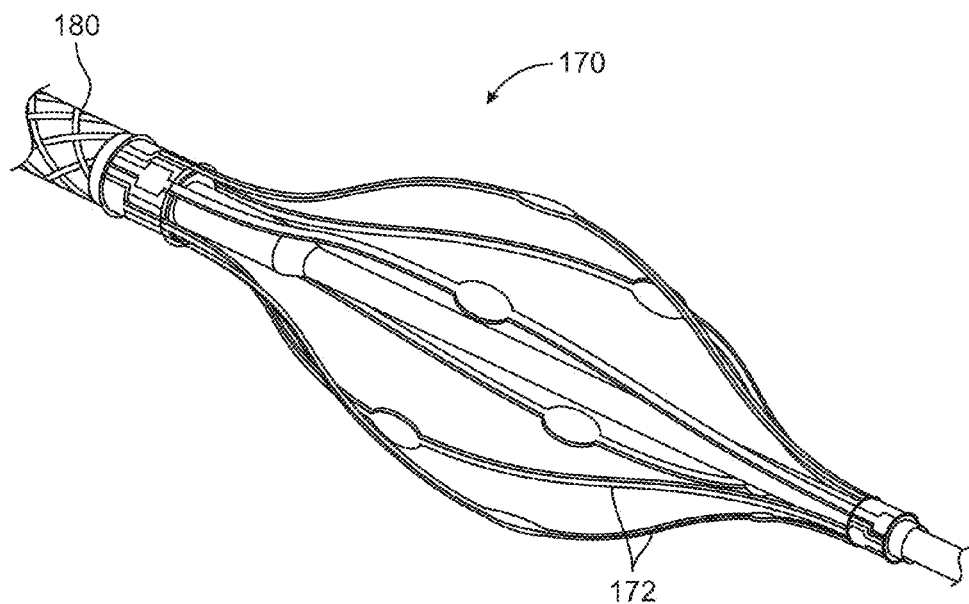

Exemplary structures for fixing struts 172 of basket 170 to a catheter body 180 are illustrated in FIG. 12G.

Figure 12H:
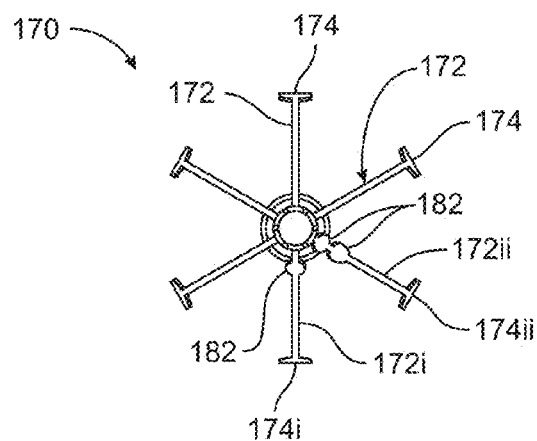

Referring now to FIGS. 12F and 12H, an alternative indicia providing a distinguishable image for rotationally registering selected electrodes 174 of basket 170 to images or other atherosclerotic material measurements can be understood. In this embodiment, an electrode 174*i* referenced as electrode 1 may have a radiopaque marker 182 disposed on the associated strut 172*i*. A strut 172*ii* supporting an associated second electrode 174*ii* may have two radiopaque markers 182 provide a circumferentially asymmetric count indicator allowing all electrodes to be referenced without ambiguity. The shape of electrodes 50 may vary, for example, electrodes 174 may be wider than other portions of struts 172 as illustrated in FIGS. 12A-G.

Remodeling will often be performed using irrigation and/or aspiration flows. In many embodiments, an irrigation port directs fluid, such as a saline solution, from an irrigation lumen to an interior of the basket. An aspiration port may provide fluid communication between an aspiration lumen and an interior of the basket. One or both of these fluid flows may be driven continuously, or may alternatively pulsate before, during, and/or after treatment. In some embodiments, aspiration and/or irrigation flow may occur acutely or concurrently so as to circulate between the irrigation port and the aspiration port. Optionally, the flow may carry ablation debris to the aspiration port, where the debris may be evacuated through the aspiration lumen. There may be coordination between the irrigation system and the aspiration system such that the irrigation fluid may remain confined in an area closely adjacent the basket so as to inhibit embolization of ablation debris when the basket is expanded within the blood vessel. Such coordination, for example, may inhibit distal movement of ablation debris, and/or may obviate any need for a distal and/or proximal barrier or membrane. In some embodiments, the circulation of fluid between an irrigation port and an aspiration port may create an effectively bloodless environment adjacent the electrodes to facilitate remodeling and/or ablation, imaging of atherosclerotic tissue, and the like.

Figure 13:
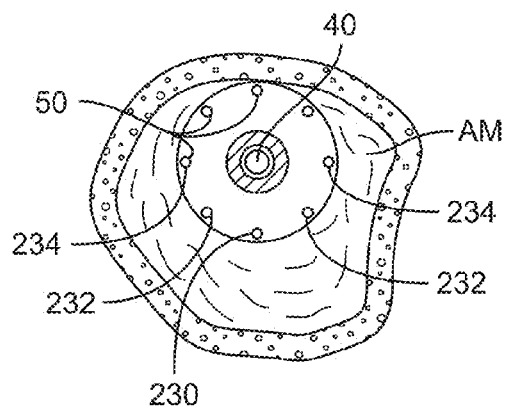
FIG. 13 is a schematic cross sectional view showing the application of different power levels through different electrodes so as to eccentrically remodel atherosclerotic materials.

Referring now to FIG. 13, controllers of the catheter systems described herein may allow distribution of differing power levels to differing pairs of electrodes. For example, in response to a circumferential distribution of atherosclerotic material AM such as that illustrated in FIG. 13, a controller may direct 50 watts of energy to a first electrode 230, 30 watts of energy to a pair of second electrodes 232 and only 10 watts of energy to a pair of third electrodes 234. Other electrodes may have no energy directed thereto, as described above. In some embodiments, a differing power directed to the differing electrodes may be provided by controlling the duty cycle, for example, with 50 watts being provided by energizing one or more electrode for 50% of the time, 30 watts being provided by energizing an electrode 30% of the time, and the like.

Many imaging modalities (including intravascular ultrasound, optical coherence tomography, intravascular MRI, and the like) may be at least in part blocked or degraded by positioning the image detecting structure within a metallic structure such as a basket formed of Nitinol™. Hence, there may be advantages in producing alternative expandable structures such as baskets comprising plastics or a polymer. In light of the heat generated by the electrodes of the systems described herein, it may be advantageous for such polymer basket structures to comprise a high temperature polymer such as a polyimide. Alternative basket structures may comprise HDPE, PET, Nylon™, PEBAX™, and the like. The basket may be formed by cutting struts from a tube of the polymer material.

Figure 14A:
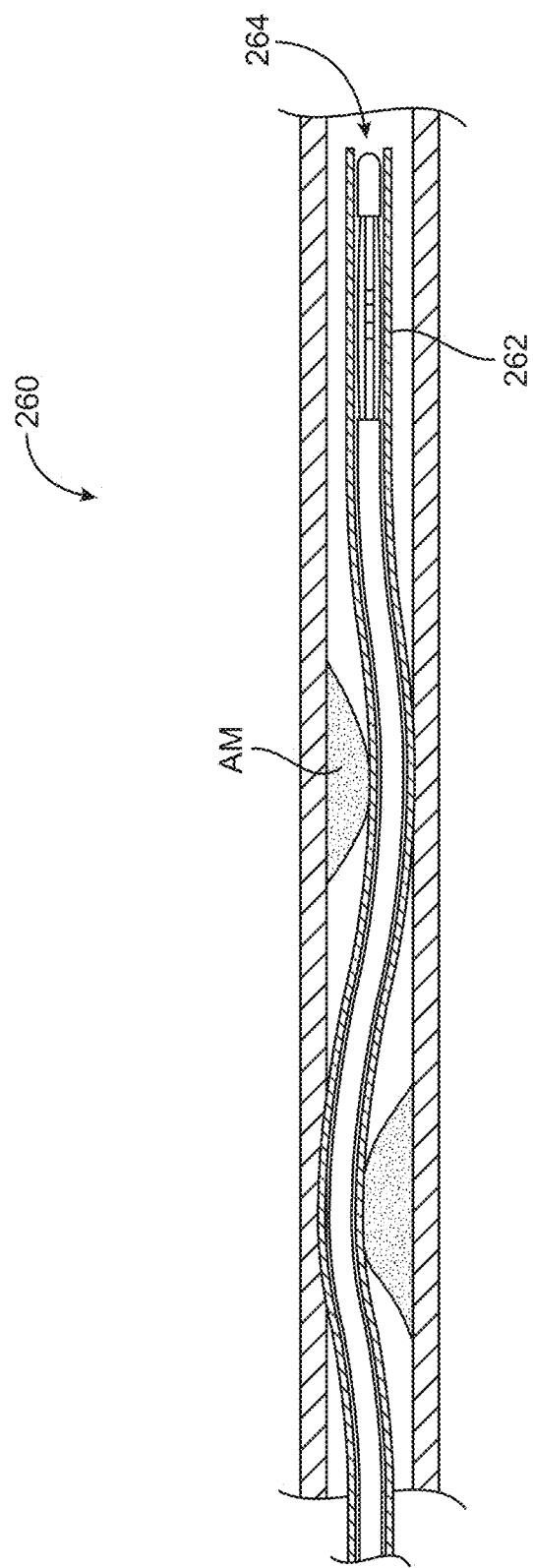
FIGS. 14A-14E are cross sectional side views through a body lumen showing additional aspects of treatment methods and devices described herein.
Figure 14B:
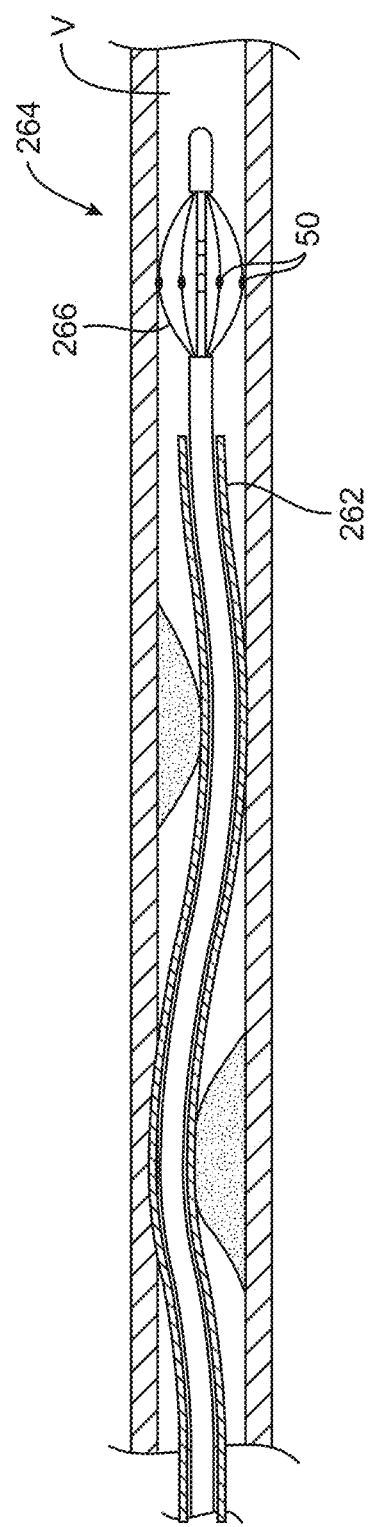

Exemplary treatment methods are illustrated in FIGS. 14A-14H. In FIG. 14A, the catheter system 260 includes a basket covering sheath 262 over an atherosclerotic material detecting and treating catheter 264 as described above. In this embodiment, outer basket sheath 262 radially restrains the basket 266, which is biased to expand radially when released from the outer sheath, as illustrated in FIG. 14B. In some embodiments, the basket may be expanded after the outer sleeve is retracted, such as by pulling pullwires, rotating one portion of the catheter relative to the other, or the like. Regardless, as the basket expands within the vessel V, electrodes 50 of the basket engage the surrounding vessel wall. An imaging transducer near basket 266 of an imaging catheter disposed in a lumen of the treatment catheter evaluates the vessel V, and the detection/treatment catheter system 264 is pulled proximally along the artery or vessel V.

Figure 14C:
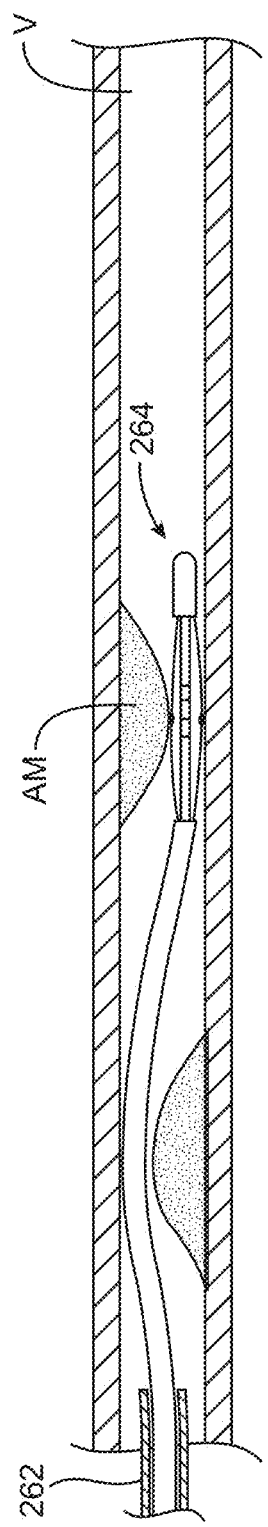
Figure 14D:
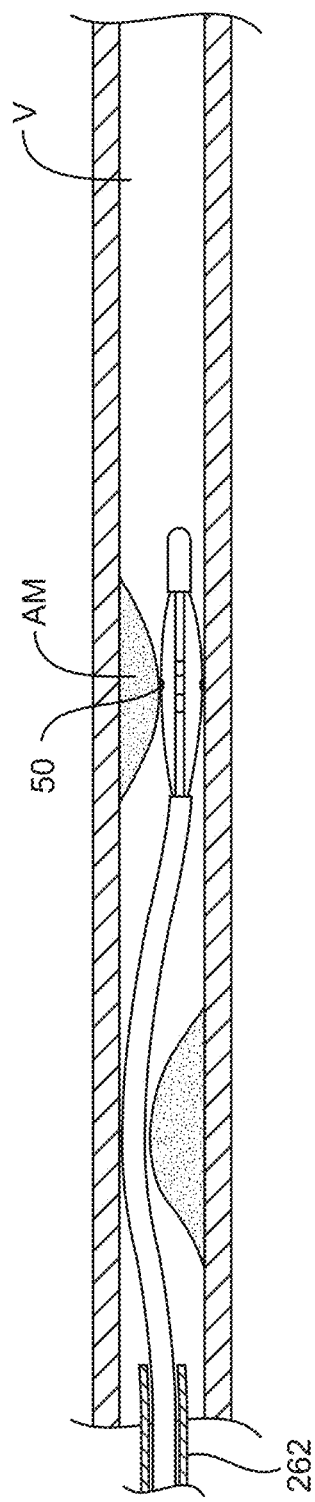
Figure 14E:
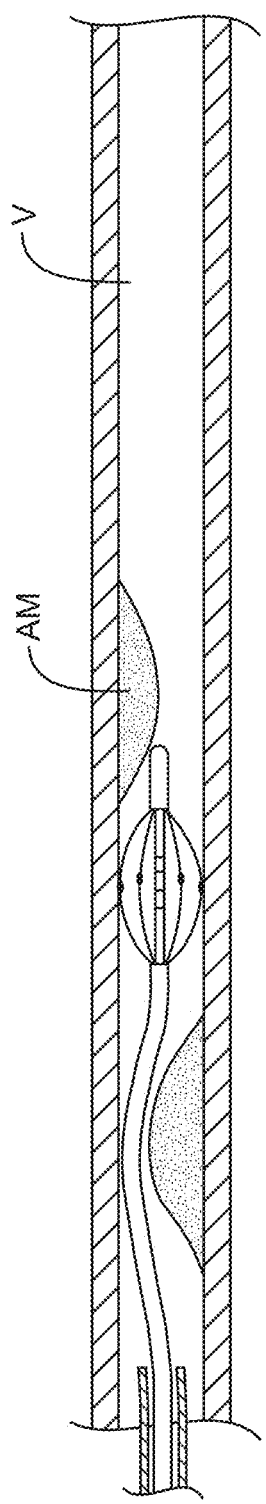
Figure 14F:
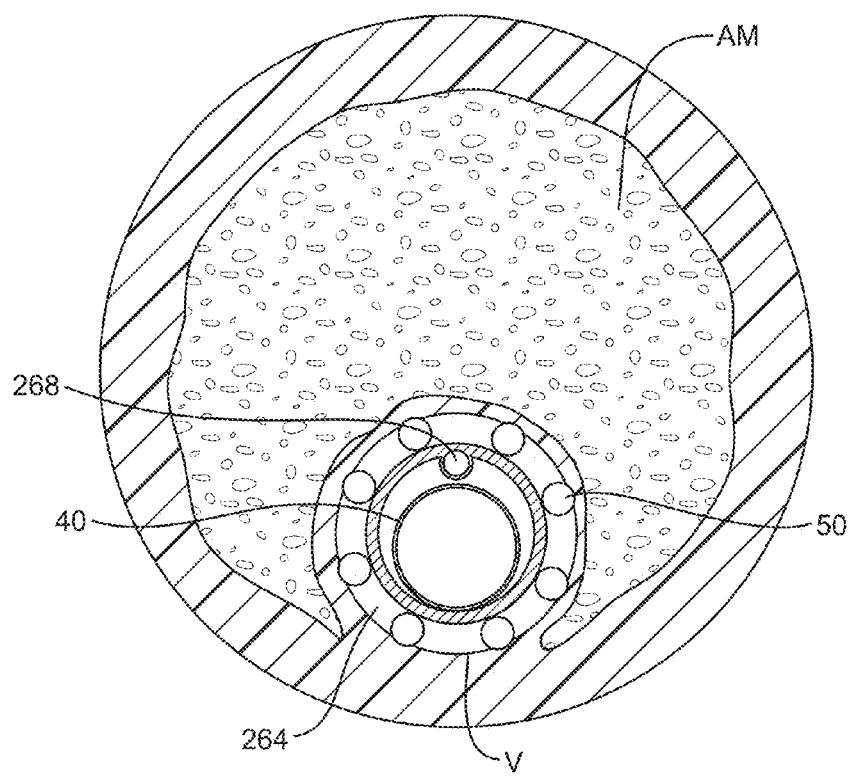
FIGS. 14F-14H are cross sectional views taken across a body lumen and treatment device to show additional aspects of the eccentric treatment methods and devices.
Figure 14G:
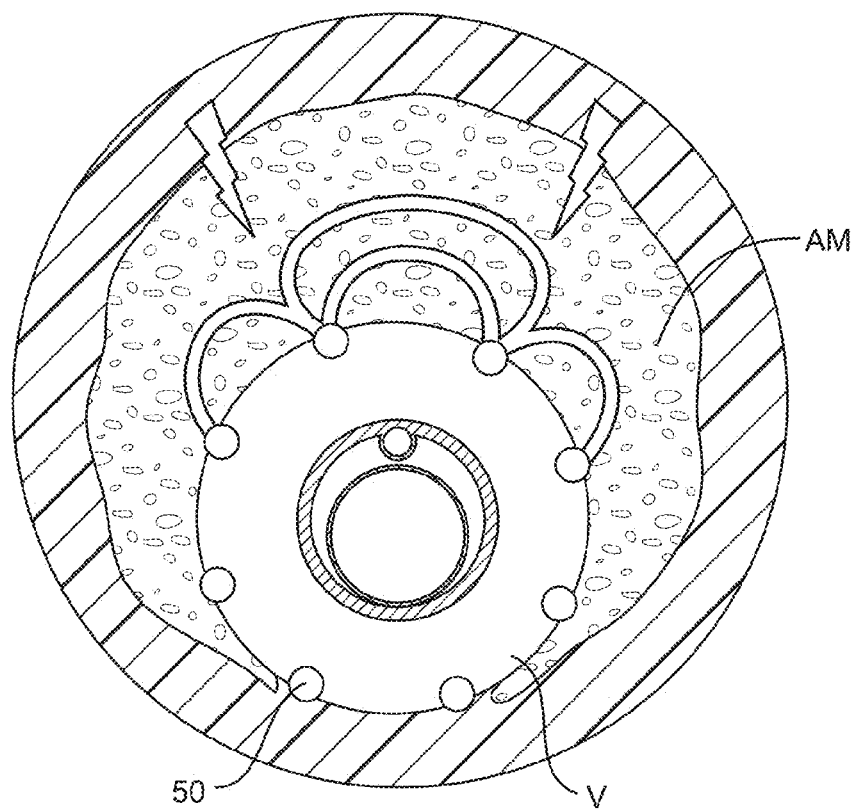
Figure 14H:
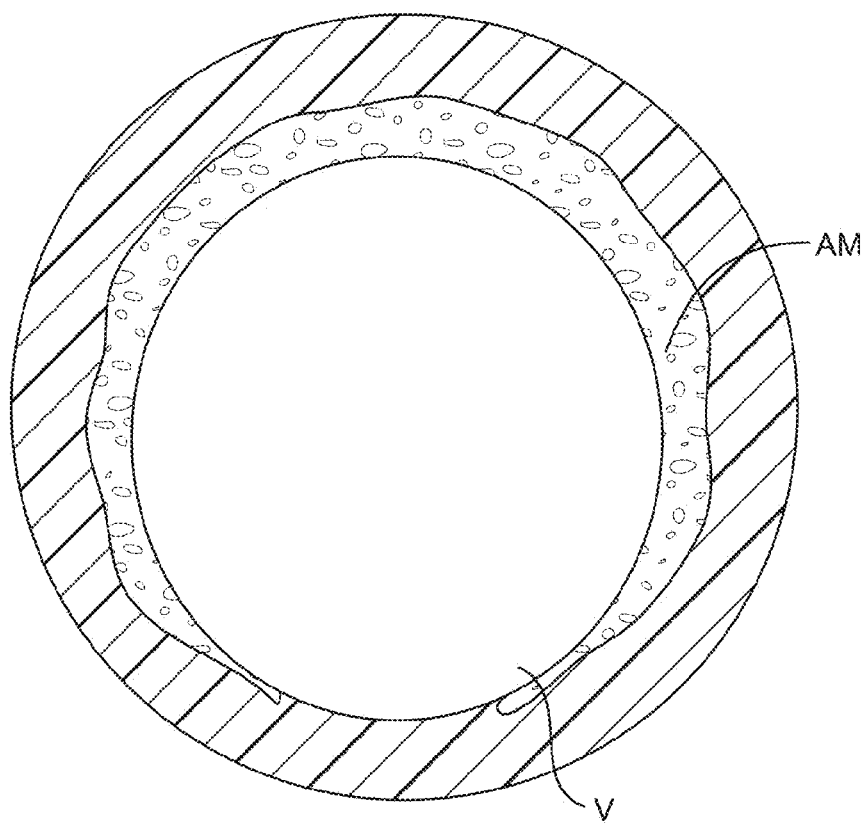

When the imaging catheter detects atherosclerotic material AM as illustrated in FIG. 14C, an appropriate subset (possibly including only a single electrode 50) is activated to remodel the atherosclerotic material AM, as illustrated in FIG. 14D, and the open vessel lumen size increases moderately during treatment. The catheter is pulled proximally to the next atheroma, which is again detected and treated. A cross section of the limited open lumen prior to treatment is schematically illustrated in FIG. 14F, which also illustrates a saline flush or irrigation lumen 268 of the catheter 264. Treatment energy and the moderate increase in the open lumen diameter of the vessel V are schematically illustrated in the cross section of FIG. 14G. After a healing response gradually increases the open lumen diameter, the longer term open lumen results schematically illustrated in FIG. 14H may then be provided.

Figure 15A:
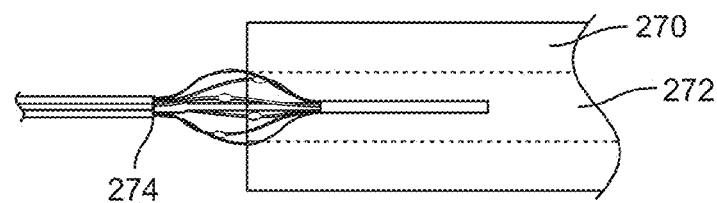
FIGS. 15A and 15B illustrate an eccentric treatment device and method in a gelatin artery model.
Figure 15B:
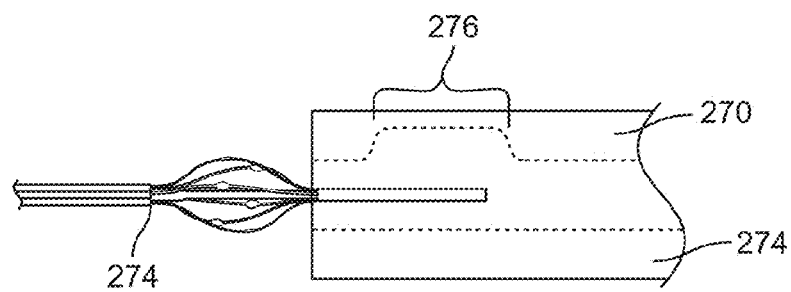

Referring now to FIGS. 15A and B, eccentric material removal in a gelatin artery model 270 are presented. Prior to the test, the artery model includes a consistent lumen 272 as seen in FIG. 15A. A test eccentric treatment catheter 274 having an expandable basket supporting a circumferential array of electrodes is introduced into lumen 272, with the expandable basket supporting the electrodes in engagement with the luminal wall. Selected electrodes of test catheter 274 were energized so as to eccentrically treat the gelatin artery model 274, thereby effecting eccentric remodeling of the gelatin model, in this case by removing an eccentric volume 276 from along one side of lumen 272. The orientation and amount of the material removed was controlled by selectively energizing electrodes of test catheter 274.

Figure 16:
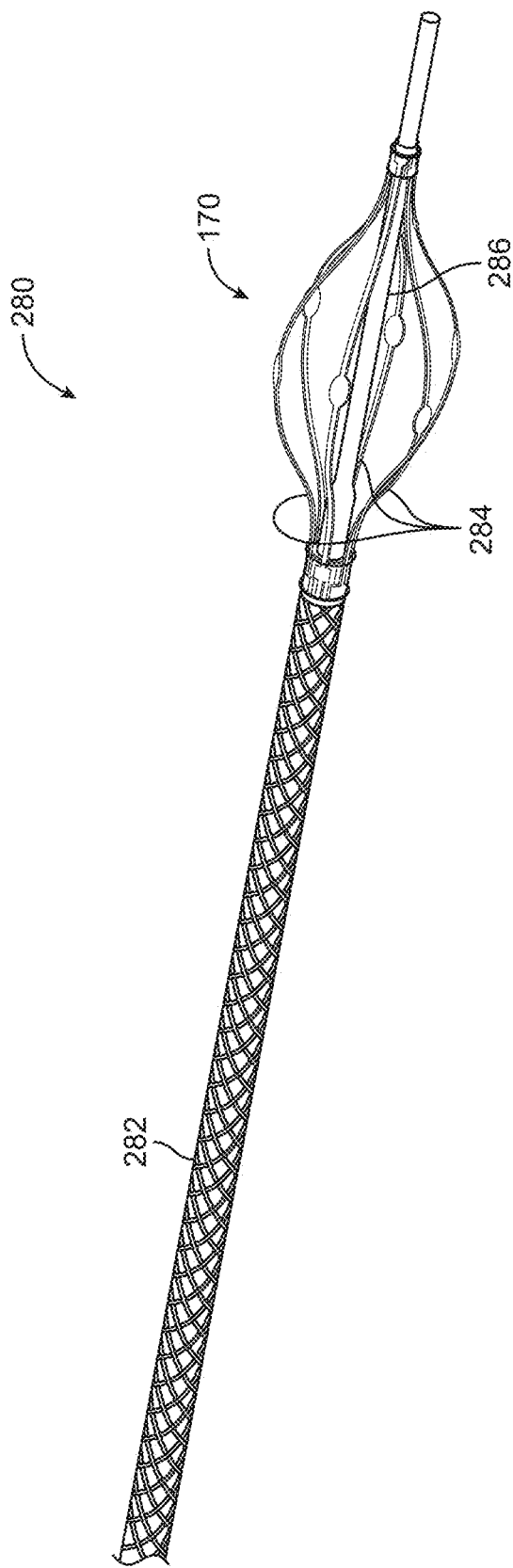
FIG. 16 is a perspective view of an exemplary catheter assembly.

Referring now to FIG. 16, an exemplary catheter system 280 is illustrated. In this embodiment, catheter body 282 includes only a single lumen, which is large enough to accommodate an imaging catheter therein and also to be used as an irrigation lumen to bring irrigation fluid to irrigation ports 284. The lumen may decrease in diameter distally of irrigation ports 284, with the decreased diameter portion 286 fittingly receiving the imaging catheter within the lumen thereof so as to direct the irrigation fluid radially outward through the plurality of irrigation ports. This embodiment may be particularly useful when remodeling atherosclerotic materials using the methods illustrated in FIGS. 14A-14H, in which mild heating improves vessel size, optionally without requiring aspiration.

Catheter body 282 may include a braided shaft in which conductive wires (for example copper wires or beryllium-copper wires) are coated with a high temperature and/or high strength insulation material such as a layer of polyimide or the like. The braided wires may be sandwiched between layers of materials forming the shaft of catheter body 282. The shaft may, for example, comprise a plurality of layers of polyethylene, an inner Teflon™ PTFE layer, an outer nylon layer, and the like.

The wires of shaft 282 may be braided so as to inhibit capacitive losses between wires when electrical currents run through them. Capacitive losses may be decreased when a wire that carries a current from an energy source to an electrode of the catheter system and a wire that carries a current from an electrode back to the energy source are not parallel, but at an angle, ideally being perpendicular. This may be achieved by braiding the wires with appropriate pitch or a number of peaks per inch. The basket structure 170 of catheter system 280 may be included, with the basket structure being described in more detail with reference to FIGS. 12A-12H. Guide 286 may extend through basket 170 and may comprise a material transparent to the imaging catheter, optionally comprising HDPE, PET, or the like.

Still further alternatives are available. For example, another way to employ RF energy to remodel atherosclerotic material may be to energize a plurality of the adjacent electrodes with differing RF signals so as to employ the adjacent electrodes as a phase-array. A phase array can direct or steer an electromagnetic signal in a desired direction using constructive and destructive interferences between signals of adjacent elements of the array. By controlling phases of the adjacent signals, a phase array of electrodes may provide a focused and/or steerable RF signal.

Along with controlling steering and directionality, adjusting phases of adjacent RF electrodes may allow focusing of some or most of the RF energy at a desired depth D inside the atherosclerotic material while inhibiting RF energy delivery between the electrode surfaces and depth D using constructive and destructive interference between the signals. For example, such a system may be employed to preserve the cap of a plaque so as to reduce restenosis. Inhibiting heating of the cap while focusing energy toward an internal portion of the plaque may lower an immune response to heat that could otherwise lead to restenosis. Hence, inhibiting heating of the cap may reduce restenosis.

In general, the present invention may make use of highly elastic, expandable structures, particularly of expandable structures formed from structural members separated by perforations so as to define a basket. Such structures can conform to an artery diameter before, during, and/or after atherosclerotic material removal. This expandability allows for direct contact of the electrodes against atheroma, although the systems of the present invention may also make use of conductive fluid environments to complete an RF energy path, or conversely, use non-conductive fluid to enhance energy directed through tissue. Multiple electrodes can be distributed circumferentially around an intermediate portion of the expandable structure, and a subset of these electrodes can be activated to allow for eccentric tissue remodeling and/or ablation.

Atheroma may be identified and targeted by intravascular imaging, and these capabilities may be integrated into the remodeling and/or ablation catheter. Preferably, the intravascular imaging capabilities will be deployed in a separate catheter which can be advanced within, and removed from the ablation catheter. In general, this intravascular imaging capability allows the progress of the therapy to be monitored so that wall perforation can be avoided, while ideally reducing occlusion to no more than 15% of the overall native vessel diameter (either upon completion of the treatment or after subsequent tissue healing). The ablation catheter may further allow the use of localized radiation or drug delivery for anti-restenosis treatments. The ablation catheter may include a relatively large lumen allowing selective use of an intravascular imaging system, a radiation delivery or other treatment catheter, an aspiration of debris and vaporization gases, with these uses often being employed sequentially. A guidewire may make use of this or a separate lumen, and the guidewire may be removed to allow access for the restenosis and/or imaging catheters.

The devices, systems, and methods described above are well suited for application of electrical energy that is tailored to target tissues and materials along a body lumen.

The exemplary catheter devices and methods for their use described herein are intended for application in the lumen of vessels of the human anatomy. The anatomical structure into which the catheter is placed may be, for example, the esophagus, the oral cavity, the nasopharyngeal cavity, the auditory tube and tympanic cavity, the sinus of the brain, the arterial system, the venous system, the heart, the larynx, the trachea, the bronchus, the stomach, the duodenum, the ileum, the colon, the rectum, the bladder, the ureter, the ejaculatory duct, the vas deferens, the urethra, the uterine cavity, the vaginal canal, and the cervical canal.

Figure 17A:
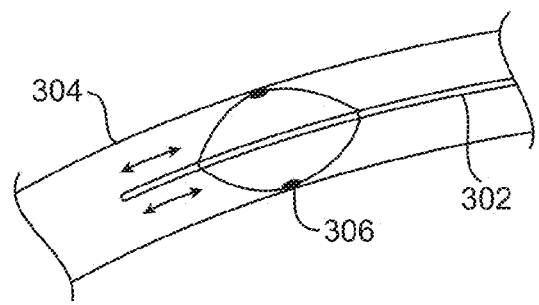
FIG. 17A illustrates physical targeting within vessel by longitudinal movement.
Figure 17B:
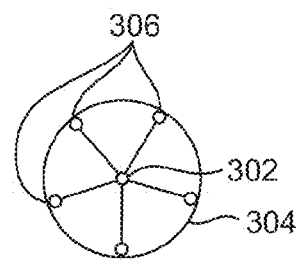
FIG. 17B illustrates physical targeting within vessel by radial electrode activation.
Figure 17C:
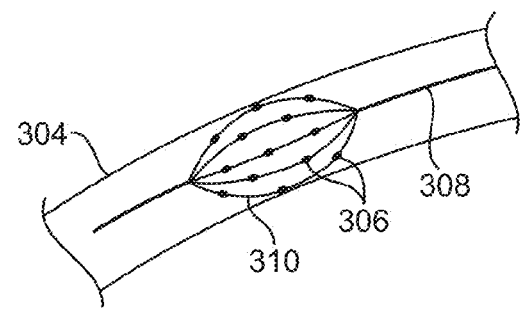
FIG. 17C illustrates physical targeting by activation of radial and longitudinal electrode combinations.

As can be understood with reference to FIGS. 17A-17C, physical targeting of eccentric disease can be accomplished by positioning of electrodes by moving longitudinally in vessel until positioned in the vicinity of targeted tissue. As schematically illustrated in FIG. 17A, axial movement of a distal end of probe in the form of a catheter 302 within a body lumen 304 allows different axial portions of the lumen wall to be targeted for analysis and treatment. An additional method to physically target eccentric disease in a radial manner is to apply bipolar energy selectively to specific electrodes 306 so as to direct energy through the targeted tissue, as can be understood with reference to FIG. 17B. In some embodiments, radial and longitudinal physical targeting may be effected by selective activation of electrodes distributed both radially and longitudinally on an expandable body 310 of a catheter 308, as illustrated in FIG. 17C.

Figure 18:
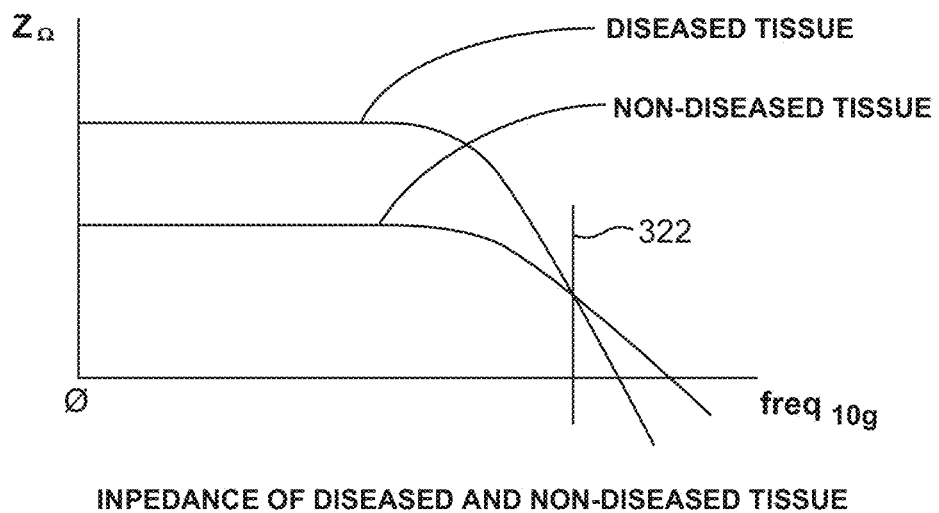
FIG. 18 illustrates electrical impedance versus frequency characteristic of diseased and non-diseased tissue.
Figure 19:
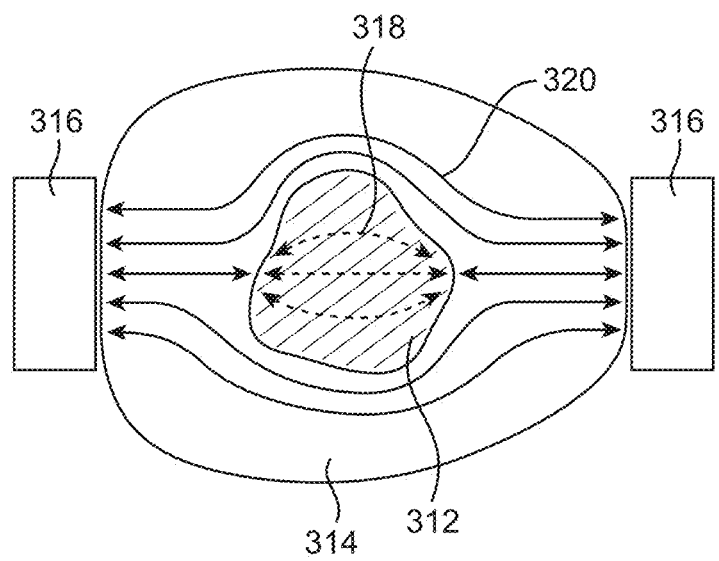
FIG. 19 illustrates shielding of high impedance tissue from electrical current by surrounding lower impedance tissue.

Frequency targeting of tissues is illustrated in FIGS. 18 and 19. As graphically illustrated in FIG. 18, different tissue types have different characteristic electrical impedances that cause the tissue to absorb energy of certain frequencies or frequency ranges more readily than others. By applying energy at the specific frequency or range of frequencies that the tissue is more conductive, energy penetrates the tissue more readily. In general, it has been shown that samples of diseased tissue exhibit higher impedance characteristics than samples of healthy tissue. As illustrated in FIG. 19, in the case where a diseased area of tissue 312 is surrounded by relatively healthy tissue 314, the healthy tissue is likely to shield the diseased tissue from electrical current flow due to the lower impedance of the healthy tissue. Hence, minimal (or less than the desired) current flow 318 may pass through diseased tissue 312, and heavier current flow 320 may be seen in low impedance healthy tissue 314 when bipolar current is transmitted between electrodes 316. Typically, the frequency ranges in which tissue impedance varies to a useful degree occur between 100 kilohertz and 10 Megahertz.

Frequency targeting seeks to deliver more energy to the diseased tissue by determining the frequency or range of frequencies at which the impedance of the diseased tissue is equal to or less than that of the healthy tissue, such as by operation at or above a threshold frequency 322 as illustrated in FIG. 18. Energy delivered at the specified frequency or range of frequencies will cause more heat to be dissipated in the diseased tissue than energy delivered outside of those specific frequencies.

Figure 20:
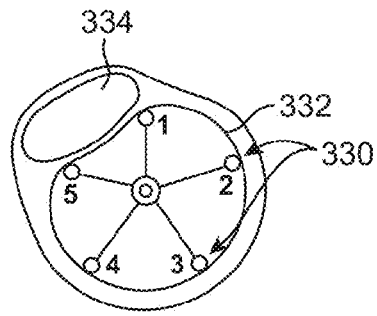
FIG. 20 illustrates electrical impedance measurement utilizing multiple radial spaced electrodes.

The use of impedance measurements to determine a location and/or state of tissue may be generally understood with reference to FIG. 20. First, impedance measurements utilizing an array of radially spaced electrodes 330 within lumen 332 can be used to analyze diseased tissue 334. Impedance measurements between the five electrodes of the array, and particularly impedance measurements between pairs of adjacent electrodes (and/or between pairs of separated electrodes), may differ when the current path passes through diseased tissue 334, and when it passes through healthy tissues of the luminal wall. Hence, impedance measurements between the electrodes on either side of diseased tissue 334 may indicate a lesion, while measurements between other pairs of adjacent electrodes indicate healthy tissue. The impedance characterizes the molecular state of a tissue. The state of a tissue can be affected/changed by temperature: for instance, some of the constituent mater included in lipids may start denaturing at temperatures between about 40 C and 85 C. At least some fatty acids (such as lauric acids, palmitic lipids, arachidic acids, and/or lignoceric acids) may change phase with treatment temperatures of 45 C or less, 65 C or less, 75 C or less, 85 C or less, or the like, and may then turn into a new liquid state that can move through or between cells and/or be safely resorped. Lesions from which these fatty acids have been melted and from which the fatty acids have been removed or resorped may be as much as 90% more compact in volume than the pre-treatment lesions including their original constituent lipids.

If one knows the temperatures of state change for a tissue, and the impedance of the different states of the tissue, then by measuring the tissue impedance, it is possible to detect a state change, and or to estimate what the temperature is, thereby allowing one to monitor the progress of the therapy. E.g.: if impedance of a lipid was 100 Ohms, and an impedance of a particular melted fatty acid was 90 Ohms (here using hypothetical values), and knowing that this particular constituent of lipids changes phase from within the fatty solid to a melted fatty acid at around 85 C, then detecting a change in impedance form 100 Ohms to 90 Ohms indicates that the lipid turned into liquid fatty acids and therefore that the temperature should be around 85 C. Analysis of diseased luminal tissues may use specific frequencies to verify a type and condition of tissue based on electrical impedance measurement. Normal use will include the discovery and characterization of diseased tissue using intraluminal ultrasound or other methods. Measurement of tissue electrical impedances over radially spaced electrodes will allow for verification of the existence of diseased tissue and knowledge of the location of the electrodes relative to specific tissue.

Figure 21:
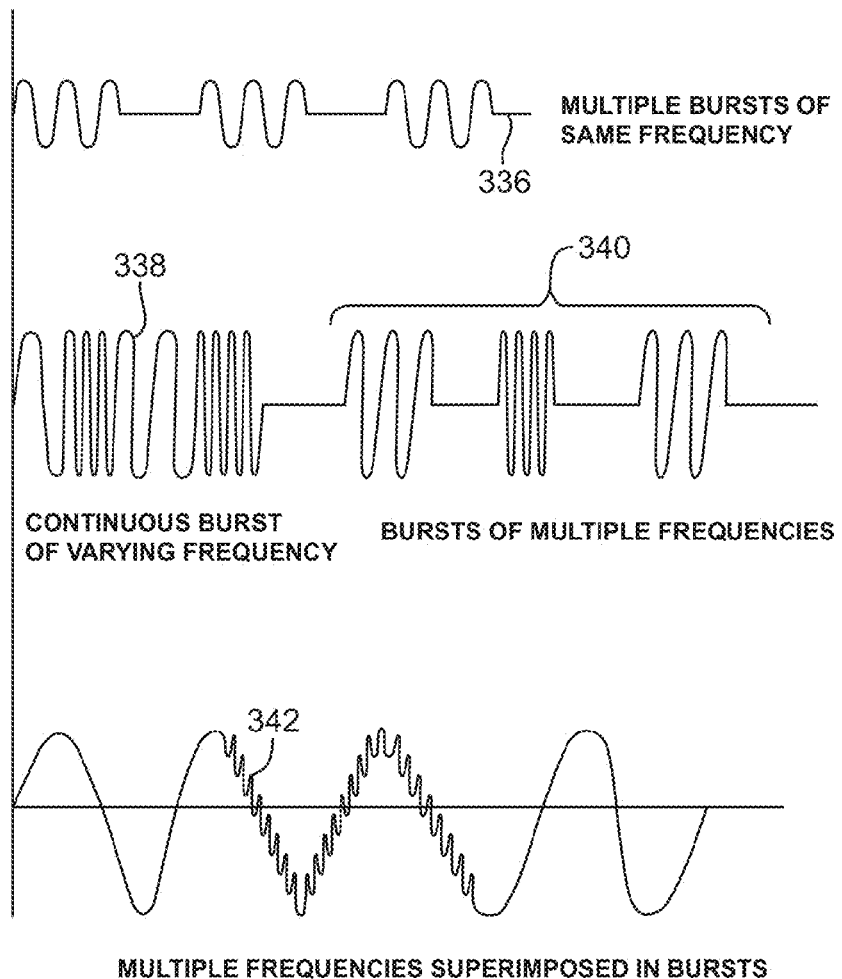
FIG. 21 illustrates variations of multiple frequency therapy.

Multiple Frequency Therapies and signals are schematically illustrated in FIG. 21. Therapy can consist of the application of electrical energy at a single frequency or at multiple frequencies. Depending on the composition of the target tissue and surrounding tissue, the optimum treatment may consist of a single frequency to target a single tissue type, multiple frequencies to target multiple tissue types, or multiple frequencies applied to a single tissue type. Multiple bursts of the same frequency 336, varying frequencies, such as a continuous burst of varying frequency 338, bursts of multiple frequencies 340, and multiple frequencies superimposed (optionally in bursts 342) may be employed.

Multiple frequencies can be applied in any sequence from any combination of electrodes in contact with the target tissue or surrounding tissue. Multiple frequencies can be applied as discrete frequencies or can be applied as a frequency sweep across a range in a linear, logarithmic, or other manner.

Figure 22:
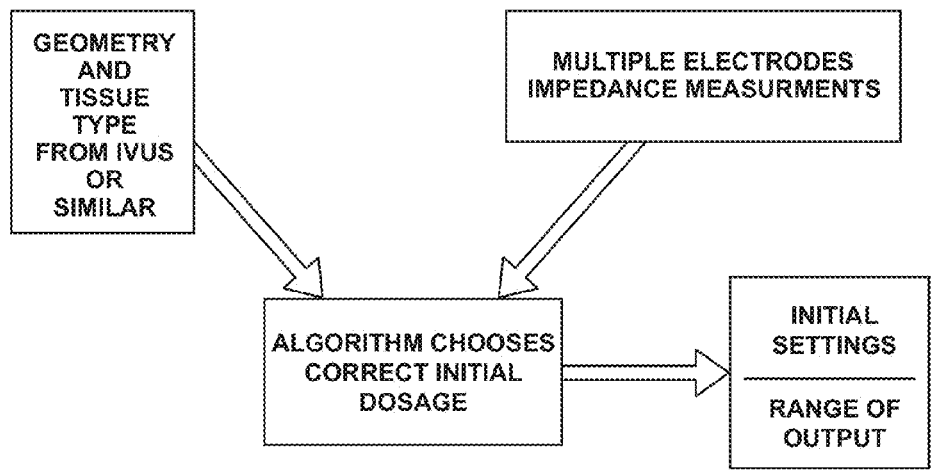
FIG. 22 illustrates use of physical tissue characteristics from external sources. combined with electrical impedance measurements to determine a desired or optimum energy setting.

An energy Control arrangement is schematically illustrated in FIG. 22. In general, impedance and physical tissue characteristics may be utilized to set the output or treatment parameters. Geometry and tissue type may be determined as described herein using IVUS or other similar detector techniques. Electrode impedance measurements from multiple electrodes may be taken. An algorithm of the system processor may choose a correct initial dosage, and initial settings and/or range output.

Regarding setting up the correct initial dosage, the shape and type of diseased tissue to be treated is generally diagnosed and characterized by ultrasonic, optical, or other types of intraluminal sensing devices. Using the multi-electrode approach, electrical impedance measurements can be used to understand the electrical characteristics of atherosclerotic tissue of varying geometries and types previously diagnosed. Using that data, the initial therapy dosage setting can be optimized.

Regarding controlling the dosage, the electrical impedance characteristics of tissues vary due to temperature variations and the molecular state of a tissue. Dynamic measurement of electrical impedance of the tissue during application of energy can be used to monitor the changes in the tissue and the progress of the therapy. A four electrode implementation of the electrode system would allow for measurement of the electrical impedance of the electrode to tissue interface and therefore, measurement of the change in temperature of the tissue at the contact surface and that of the contact tissue.

Regarding determination of proper dosage during therapy, the pattern of energy delivery can be a single pulse or multiple pulses of varying duration separated by resting periods of varying duration. The measurement of electrical impedance of the tissue and of the electrode to tissue interface during energy delivery and between energy pulses can be used to determine the optimum durations of energy delivery and resting periods. Pre-treatment bursts of RF energy can be applied to condition the target tissue. Conditioning may be utilized to activate Heat-Shock Proteins (HSPs) in healthy tissue prior to treatment to get better protection of healthy tissue. Post-treatment bursts of RF energy can be applied to control the cool down time of the tissue. Interim treatment bursts of RF energy can be applied to control the temperature of the target and surrounding tissue between multiple therapy bursts. Energy can be delivered in any combination of amplitude and frequency from any combination of electrodes.

Impedance measurement on multiple electrodes can also be employed. When a multi electrode design is used it is likely that some of the electrodes will be in contact with the lumen wall and others will be suspended in the blood or other existing fluid or thrombus, or existing stents, or foreign materials of the like. The measurement of impedance at various radial locations allows the determination of which electrodes are in contact with the lumen wall and which ones are in contact with fluid such a blood. This contact determination can be used in combination with an intraluminal viewing device such as ultrasound to determine the physical orientation of electrodes.

Utilizing the impedance measurements between multiple electrodes, the determination of the contact status of each electrode with tissue or blood can be utilized to determine if the electrode carrying mechanism (catheter) is in the proper location for therapy. Impedance measurements between multiple electrodes can be used to determine contact quality of electrodes to tissue. Poor contact quality can cause excessive or unwanted localized heating or can otherwise prevent optimum treatment. Determination of contact quality can be utilized to minimize this type of problem.

In some situations the choice of electrode may be determined by a combination of position and quality of contact. Impedance measurements between multiple electrodes can be utilized to better understand which electrodes are in better contact or a better position to treat a specific area or lesion.

In some situations the determination of energy level and frequency to be applied to the target can be based on quality of contact. Impedance measurements between multiple electrodes can be utilized to determine the optimum energy level and frequency.

In some situations energy may be applied to a single pair of electrodes, between multiple pairs of electrodes, or from a single electrode to multiple electrodes, or any combination thereof. Impedance measurements between multiple electrodes can be utilized to determine the optimum pattern.

Figure 23:
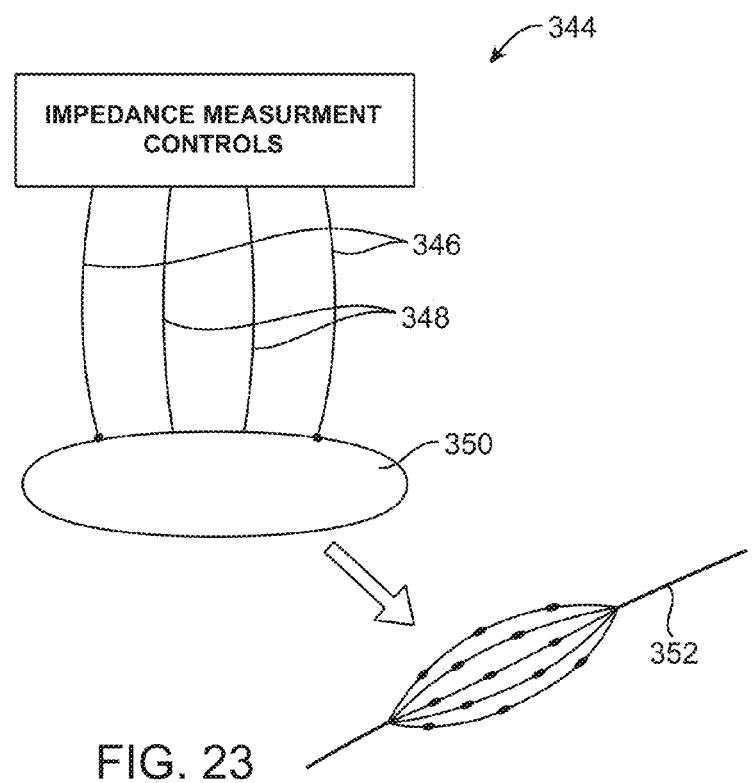
FIG. 23 illustrates four electrode measurement system distributed across multiple electrodes to measure contact and tissue impedance.

Different embodiments may employ impedance measurement using two vs four electrodes, as can be understood with reference to FIG. 23. Four electrode systems have been used for the measurement of electrical impedance in many applications. Four electrode systems are inherently more accurate than two electrode systems due to inaccuracies created in the two electrode systems by excessive contact impedance and electrical polarization reactions created in the contact area. In the four electrode system 344 energy is delivered to the target by two energy delivery electrodes 346 and an impedance measurement is taken between the other two high impedance electrodes 348 shown schematically in contact with the tissue 350 in the energy path. In this multiple electrode application any two electrodes can be utilized to deliver energy while any other two electrodes can be utilized for impedance measurement, thus forming a four electrode measurement system. A probe or catheter 352 may include a circumferential and/or longitudinally distributed array of electrodes may be used to contact the tissue, and any four electrodes of the catheter can be configured for energy delivery or impedance measurement. Thus, the electrode array can be utilized as a two or four electrode system.

In many applications it is helpful to know how much energy is being delivered to the target tissue and how much is being dissipated in the interface between the electrodes and tissue. By taking measurements as a two electrode system and then as a four electrode system the electrode to tissue interface can be characterized and that data can be utilized to determine how much energy is being dissipated in the electrode to tissue interface and how much is actually delivered to the target tissue.

Measurement of the electrical impedance in two or four electrode configurations can be performed statically utilizing small excitation signals or can be measured dynamically during the application of energy at the normal therapy levels. Using this technique, tissue electrical impedance can be measured dynamically during the application of energy to determine the state of the treated tissue and surrounding tissue.

Impedance measurement may optionally be performed in mono-polar configuration. It is possible to utilize multiple electrode systems in a mono-polar configuration where the return electrode is an electrically conductive pad applied to the external surface of the patient or the like. In this configuration impedance measurements can be performed between any one of the internally applied electrodes and the external return pad in the two electrode mode or any one of the internally applied electrodes can apply energy that flows to the external return pad while any other two internally applied electrodes is used to measure impedance.

Regarding temperature measurements, impedance measurements taken prior to therapy can be utilized to calculate a normalized value to be used in further calculations to determine the change in temperature from that initial value. Dynamic monitoring of the electrical impedance of target and surrounding tissue during therapy can be utilized to calculate the change in temperature of tissue. In some embodiments, dynamic monitoring or the electrical impedance of interface between electrodes and tissue can be utilized to prevent tissue charring or coagulation of blood at the interface.

Temperature change during therapy can be utilized to determine the effectiveness of energy delivery settings and to determine the condition of the tissue being treated.

Temperature measurement can be performed by intraluminal ultrasound or other mechanism and verified by data derived from impedance measurements.

Figure 24:
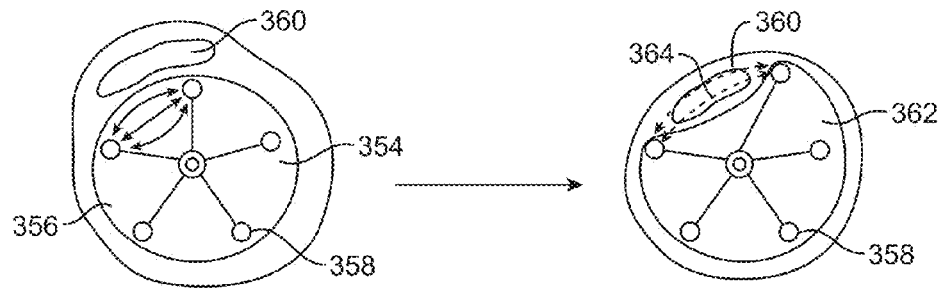
FIG. 24 illustrates flooding of vessel with non-ionic fluid to direct energy to vessel wall and surrounding tissue, reducing losses in native fluid.

Use of the systems described herein with ionic and non-ionic fluid can be understood with reference to FIG. 24. When electrical current flows in an ionic fluid such as blood filling a lumen 356, at least a portion of the current may pass through the blood when electrodes 358 are energized. Even when electrodes on either side of a target tissue 360, heating of the target tissue may be reduced by the current flow within the blood in area 354.

When used in a fluid filled lumen such as an artery, this device can be used in combination with a non-ionic fluid flooding the area 362 to displace or partially displace the native fluid to modify the conductivity of the environment around the electrodes. This action can be desirable in order to direct the energy, in form of electrical current 364, into lumen walls instead of through the native fluid, thereby delivering energy to the tissue of the surrounding walls with minimal dissipation into the fluid filling the lumen.

A second purpose of the non-ionic fluid or an ionic fluid may be to provide cooling to the electrodes and to the tissue on the surface and just below the surface of the lumen wall.

Electrical impedance measurements at the electrodes can be utilized to determine the conductivity of the surrounding fluid, thus measuring the concentration of non-ionic fluid in the native fluid. This data can be fed to the control system to allow for adjustment of ionic fluid concentration to optimize delivery of energy to the target tissue and minimize undesired effects to surrounding tissue.

Use of blood as contact interface is also an option. Blood is a conductive ionic fluid that may be used as an interface between electrodes and tissue to ensure a good electrode-tissue contact and low contact impedance.

Figure 25:
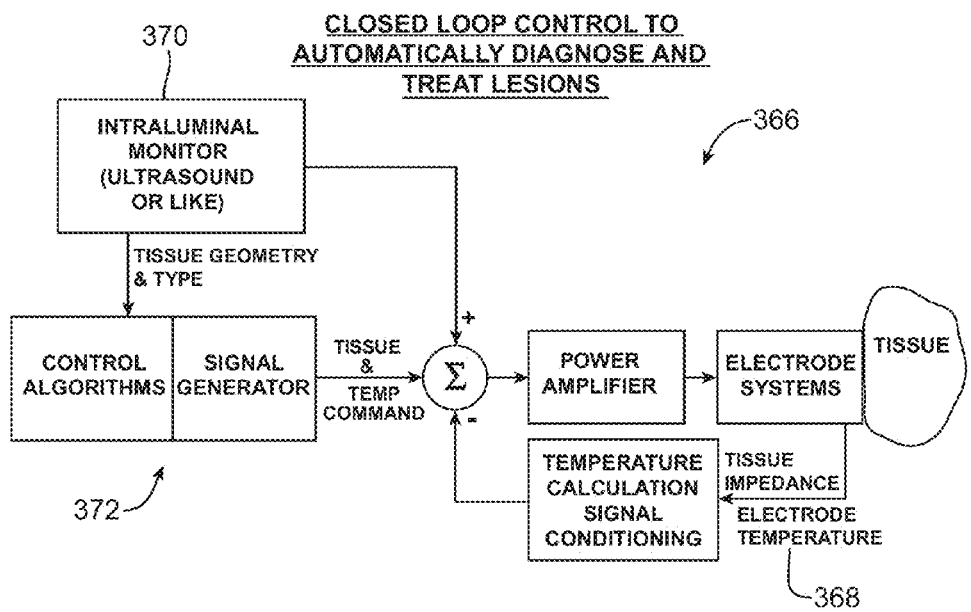
FIG. 25 illustrates one embodiment of a closed loop control system to automatically diagnose and treat lesions within a vessel utilizing tissue information from an external source such as IVUS.

Closed loop control can be understood with reference to FIG. 25. Impedance measurements over frequency ranges and across multiple electrodes can be utilized to verify electrode location relative to tissue landmarks, optionally by correlation to companion intraluminal measurement devices such a IVUS prior to and during therapy.

Impedance measurements using a closed loop treatment controller 366 making use of hardware and/or software of the system processor may facilitate treatment control. Such control over frequency ranges and across multiple electrodes can be utilized to monitor and to verify physical changes such as tissue shrinkage or denaturing of tissue in the application area. This data can be utilized to verify physical changes observed by other intraluminal observation techniques such as ultrasound.

Data from impedance measurements 368 combined with inputs from intraluminal measurement devices 370 such as ultrasound can be used to determine electrode selection from a predetermined set of rules of a controller or processor module 372. This type of control system could potentially be utilized in an automatic mode to diagnose and treat diseased intraluminal tissue.

Data about the condition of the tissue, optionally including temperature change, electrode to tissue interface impedance, tissue impedance, electrode to tissue or blood contact, and intraluminal geometry and tissue type from ultrasound or other sources, can be utilized by a controller as inputs to a closed loop control system 366.

Figure 26A:
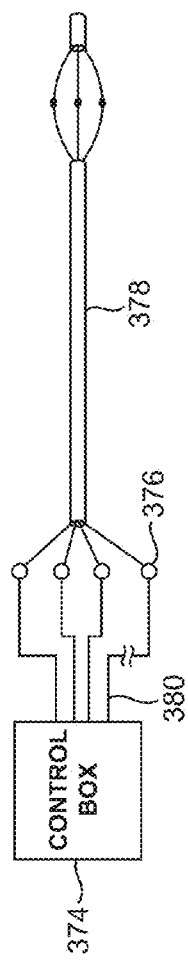
FIG. 26A illustrates the switching mechanism in an external control box.
Figure 26B:
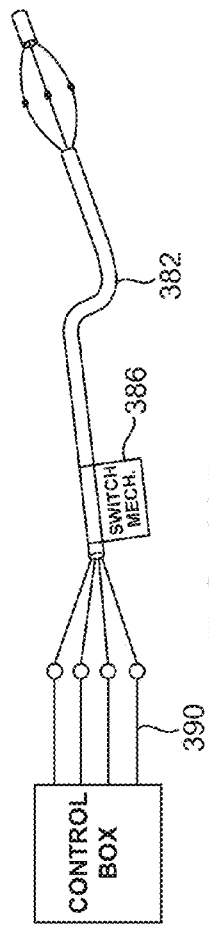
FIG. 26B illustrates the switching mechanism at the distal end of the catheter.
Figure 26C:
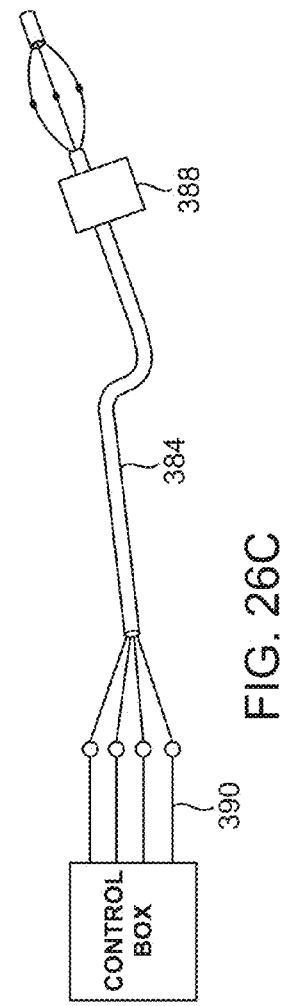
FIG. 26C illustrates the switching mechanism at the proximal end of the catheter.

Implementation of electrode switching may employ any of a wide variety of selective energizing electrode circuits, switch types, switch locations, and the like, some of which are schematically illustrated in FIGS. 26A-26C.

Electrode switches can be located in an external instrument or external control box 374, so that one external connector point 376 is provided for each electrode of catheter of catheter 378, with one wire per electrode 380 extending to, in and/or along the body of the catheter. Alternatively, electrode switch mechanisms 386, 388 may be embedded in a catheter 382, 384, respectively, either near the proximal end of the catheter for external switching or near the distal end of the catheter for internal switching. A limited number (e.g., 4) wires 390 may run proximally of the switching mechanism, while one wire per electrode may extend distally of the switching mechanism. Connection of discrete electrodes to RF generator or impedance measuring device can be accomplished by either electromechanical or solid state means.

Switching mechanisms disposed at distal end of catheter may have advantages. If located on the catheter, the switching mechanism can be located at the distal end to decrease the number of wires in the body of the catheter or at the proximal end. In embodiments of switching mechanism located at distal end of catheter the external control circuit optionally communicates with the switching mechanism via the same wires used for impedance measurements.

Switching mechanism at proximal end or other location on catheter may also be employed. The switching mechanism can be located at proximal end or any other location on the catheter if it provides advantage in performance or cost.

Figure 27:
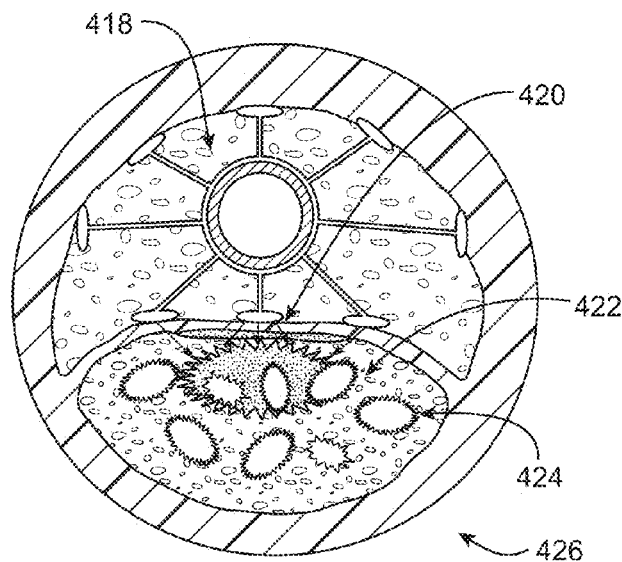
FIG. 27 illustrates selective treatment of plaque.
Figure 27A:
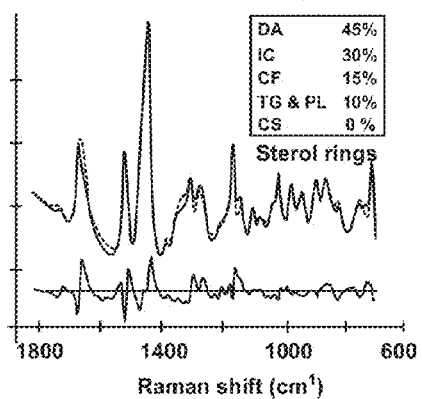
FIGS. 27A-27C illustrate spectral correlations of tissues, as may be used to analyze or characterize plaques.
Figure 27B:
Figure 27C:

Referring now to FIG. 27, the catheter devices 418, systems and methods described herein will often be used to treat plaques 422 having fibrous tissue 420. Fibrous tissue 420 may be heated to a target tissue to a temperature in a range from about 90 to about 95 C, which may provide shrinkage of up to about 50%. Lipids 424 may be heated to target temperatures in a range from about 80-85 C, providing up to about 90% shrinkage. Damage to adventitial layer 426 may be inhibited or the layer protected by limiting heating to below about 62 C. These and other temperatures and shrinkage estimates can be determined by appropriate empirical testing or the like, from unpublished and/or published work, or form other sources. Referring to FIGS. 27A-27C, spectral correlations to diseased tissue may allow tissue characterization using techniques such as those described in an article by Tjeerd J. Romer et al. entitled "Histopathology of Human Coronary Atherosclerosis by Quantifying Its Chemical Composition with Raman Spectroscopy," *Circulation* 97:878-885 (1998).

Figure 28A:
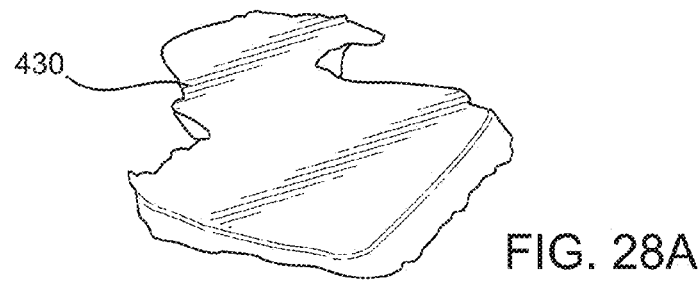
FIGS. 28A-28D illustrate bench top remodeling of tissue using an animal fat model treated with an exemplary embodiment of the catheter system.
Figure 28B:
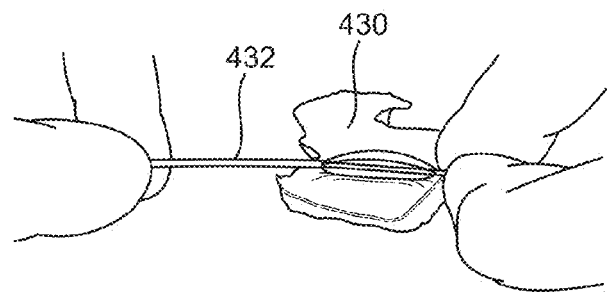
Figure 28C:
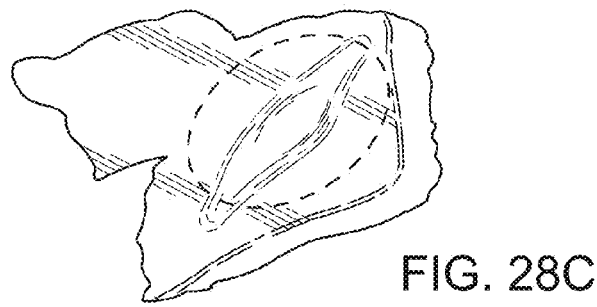
Figure 28D:
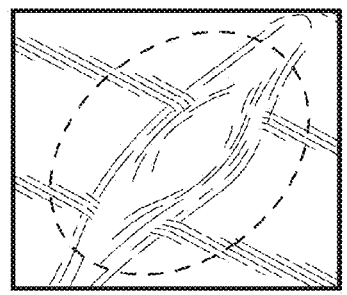
Figure 29A:
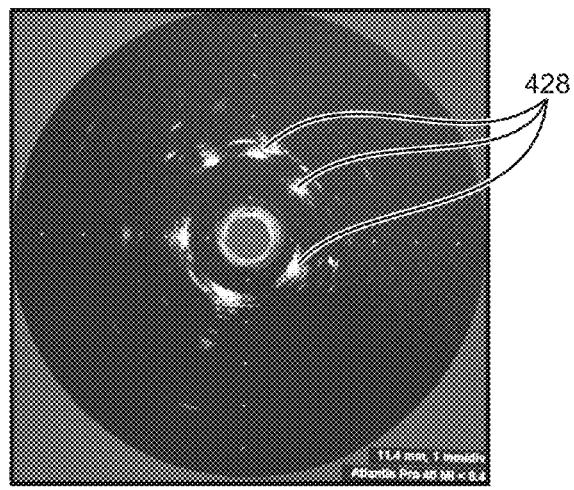
FIGS. 29A and 29B illustrate intravascular imaging and eccentric remodeling with an exemplary embodiment of the catheter system.
Figure 29B:
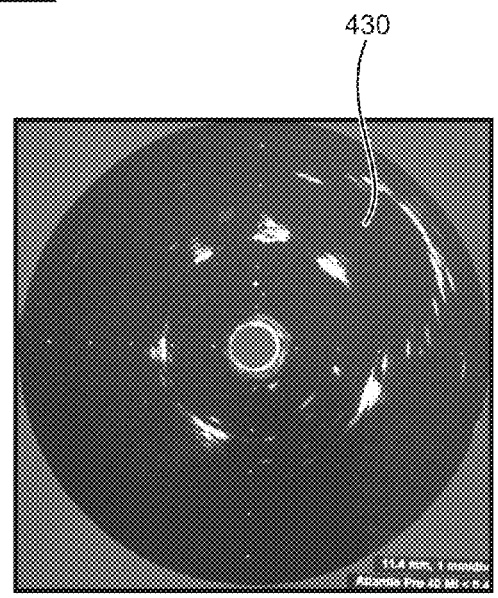

Referring now to FIGS. 28A-28D, feasibility of tissue shrinkage may be seen in a bench top experiment using a catheter system such as those described herein. An animal fat tissue model 430 (shown before the treatment in FIG. 28A) can be treated by manually holding the expandable structure and associated electrodes of the catheter 432 in contact with a surface of the tissue during treatment with tissue remodeling electrosurgical energy (see FIG. 28B). After treatment, as seen in FIG. 28C and the close up of FIG. 28D, visible shrinkage of the tissue can be verified. Feasibility of the use of intravascular imaging with the methods and systems described herein can be verified by images of the six individual electrode-supporting struts 428 of the expandable structure of the catheter in FIG. 29A, as well as by viewing an eccentric void 430 that is created using a benign guided reshaping energy delivery targeted so as to increase effective artery diameter for better blood flow, as seen in FIG. 29B.

Figure 30:
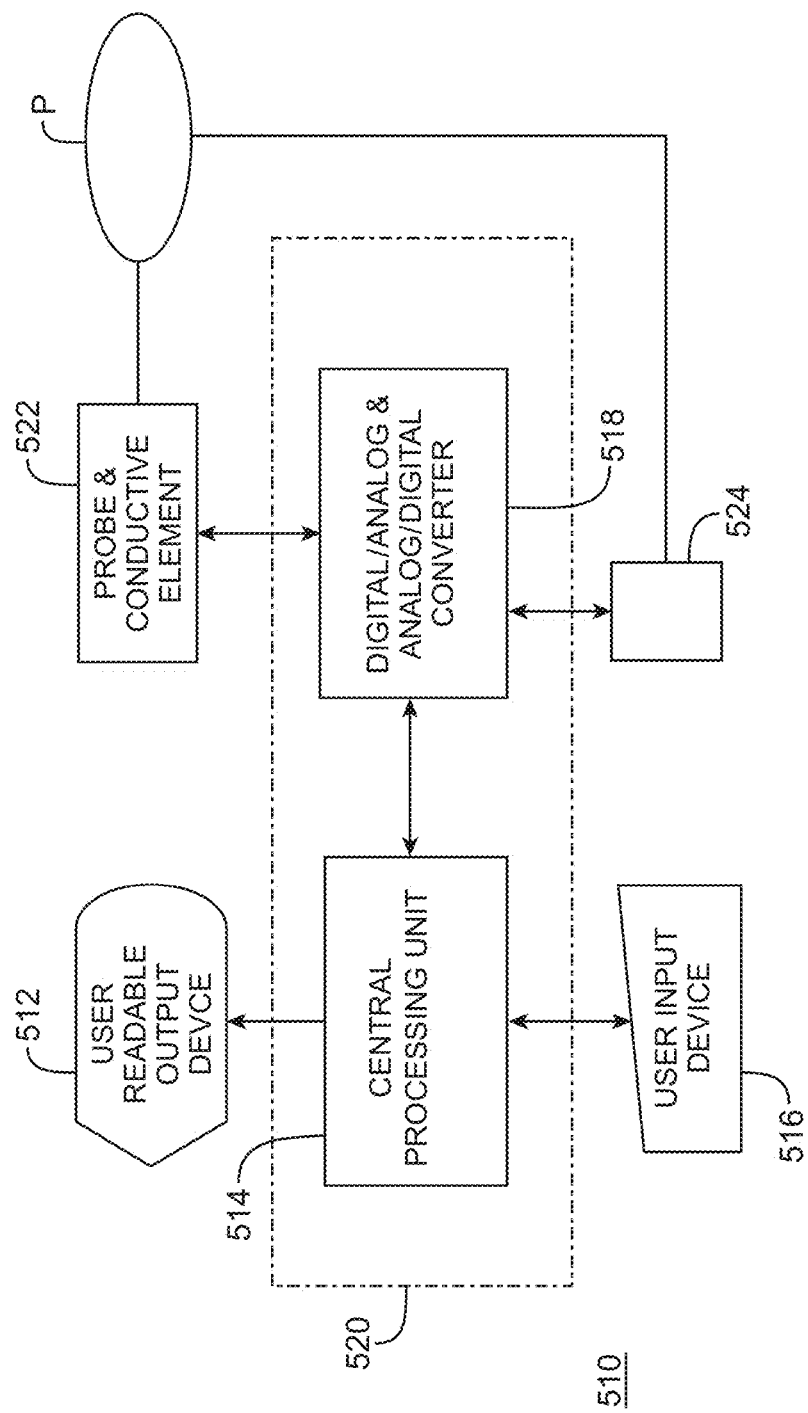
FIG. 30 is a simplified schematic illustrating components of the system of FIG. 2 that can be used for intraluminal tissue and other material analysis and characterization.

Referring now to FIG. 30, advantageous embodiments may employ aspects of electrical tissue discrimination techniques and devices described in U.S. Pat. No. 6,760,616 to Hoey et al., entitled "Tissue Discrimination and Applications in Medical Procedures," the full disclosure of which is incorporated herein by reference. As more fully described in that reference, tissue identification system 510 includes a user readable output device 512, a user input device 516, a processor 520, and a probe 522. The processor 520 includes a central processing unit ("CPU") 514, a Digital to Analog converter ("D/A"), and an Analog to Digital converter ("A/D") 518. Processor 520 may be included in processor 49 (see FIGS. 2 and 3), and probe 522 may comprise any of the catheter structures described herein, so that tissue identification system 510 may be embodied in system 10.

Figure 31A:
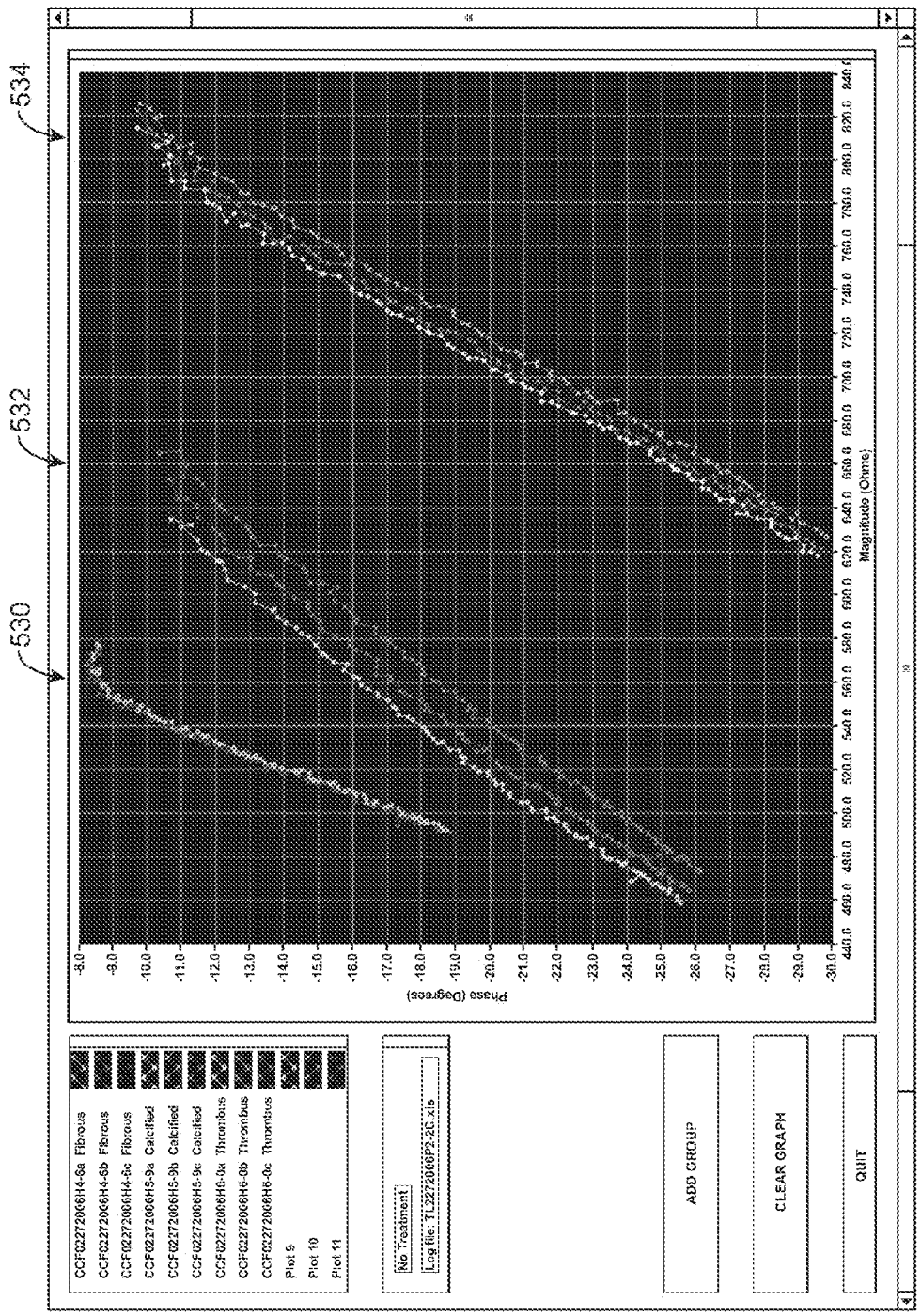
FIGS. 31A-31J graphically illustrate relationships between phase angles and impedance in a frequency range as can be use to electrically analyze and characterize materials engaging and disposed between electrodes of the system of FIG. 2.

Referring now to FIGS. 30 and 31A, tissue identification system 510 may apply a sliding or variable frequency electrical signal by energizing the electrode with a variable frequency power source 524. Power source 524, the electrode of probe 522, and the engaged tissue of patient P can thus generally be included in a circuit, and an electrical characteristic of the circuit can be measured at different frequencies. In exemplary embodiments, an impedance (both phase angle and magnitude) of the circuit are measured at a plurality of frequencies within a frequency range of about 4 KHz to about 2 MHz. For each frequency, a phase angle vs. magnitude datapoint may represent a tissue signature measurement, with a series of individual datapoints often being taken under similar conditions (for example, at a given frequency and without moving the electrodes) and averaged for enhanced accuracy. The tissue signature datapoints may be measure at a plurality of frequencies throughout a range of frequencies so as to generate phase angle vs. magnitude curves representing a tissue signature profile or correlation 530, 532, or 534, which may be used to characterize the tissue of the circuit. The phase angle can refer, for example, to the angle between the voltage and current, and the frequencies at which the datapoints of the profiles may vary across the profiles.

The signals used to derive the tissue signature profiles 530, 532, 543 will often be driven between electrodes of the catheters described herein. Conveniently, the tissue included in the circuit may be controlled by selecting different electrode pairs for testing, with or without repositioning of the electrodes. There may be significant patient-to-patient differences (or even region to region differences within a patient) for individual tissue signature measurements, and these differences may, at least in part, be caused by the different configurations of the electrodes during testing, different distances between electrodes, and the like. Nonetheless, the relationships (and particularly the relative slopes of the profile correlations, the offsets between correlations, and the like will be sufficiently consistent to allow tissue characterization, particularly where a baseline tissue signature profile for the patient or tissue region is obtained using IVUS, OCT, or the like. Where a region of (for example) healthy tissue can be identified using IVUS and used to generate a baseline tissue signature profile for the patient, other nearby tissue signature measurements or profiles can then be normalized to that baseline, compared to the baseline, and/or the like. From the offsets, the differences in slope, and the like, the tissue can be analyzed.

Referring now to FIGS. 31A-31J, the relationships between tissue signature profile curves or correlations can be used to analyze and characterize the tissues engaged by the electrodes of the probe. For example, a correlation 530 associated with fibrous plaque (seen on the left side of the graph of FIG. 31A) has both a slope and a magnitude that differs significantly from that of a calcified plaque 534 (seen in the right side of the plotted data) and from a correlation 532 associated with thrombus (generally between 530 and 534). The offsets between the correlations here encompasses a difference in phase for a given impedance, a difference in impedance for a given phase, or the like. As can be understood with reference to the graphical plots, the relationships between correlations may be determined by fitting curves to the data, by statistical analysis, by lookup tables, or the like. In exemplary embodiments, tissue signature measurements may be taken by (for example) a commercially available vector impedance meter such as a Hewlett-Packard Model No. 4193A, and the correlations may be captured using LabView™ Software and plotted or manipulated using Excel™ spreadsheet software from Microsoft, or the like. Once sufficient benchmarked data has been obtained and repeatability under different probe configurations has been established, electrical circuit measurements tissue characterization without benchmarking of each patient may avoid the expense of IVUS measurements.

Figure 31B:
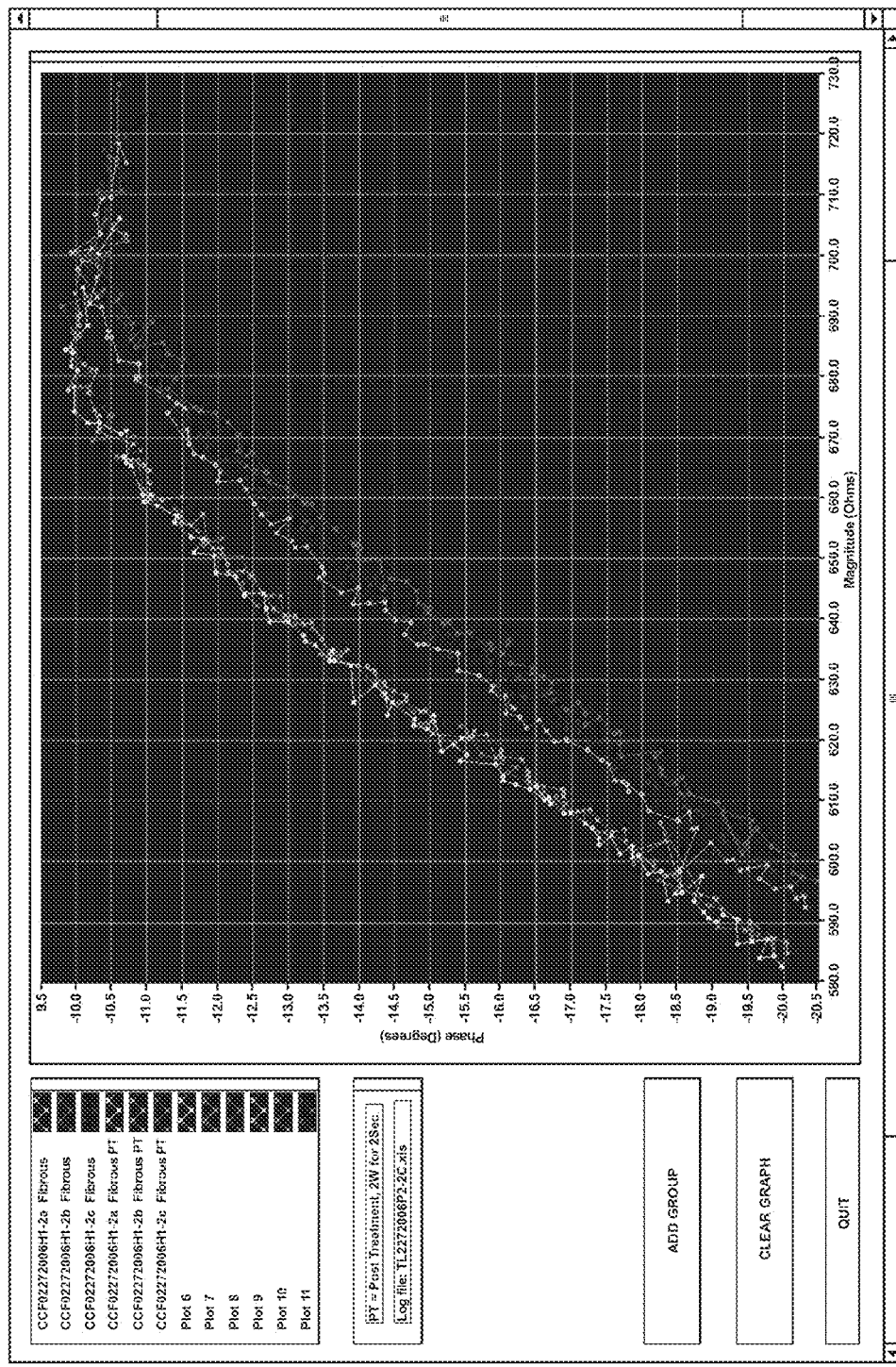
Figure 31C:
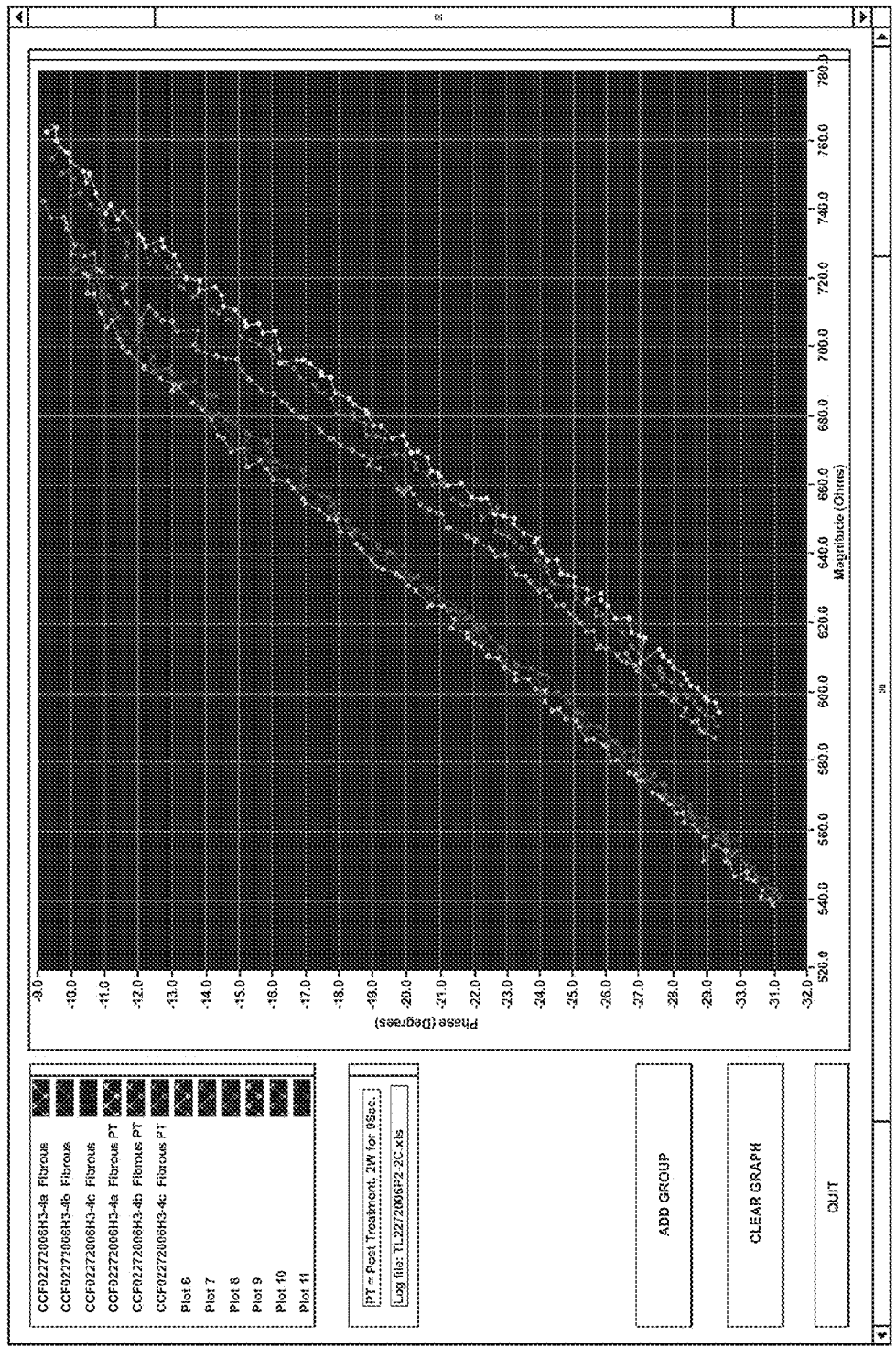
Figure 31D:
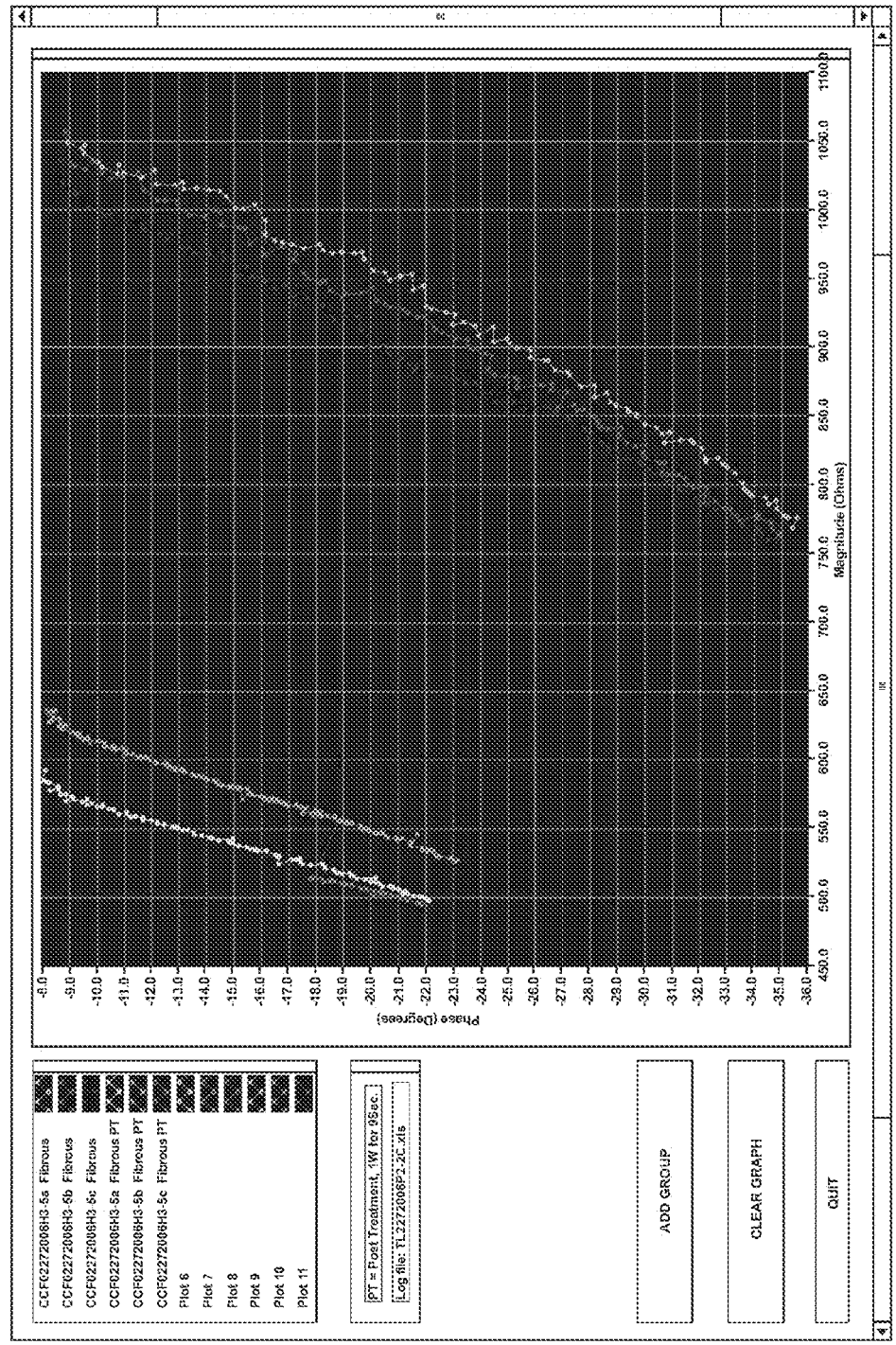

Referring now to FIG. 31B, along with characterizing different tissues, the relationships can also be used as feedback on treatments of luminal walls. A fibrous plaque correlation or profile before treatment (toward the right side of the plot) changes in magnitude during treatment to a post-treatment correlation or profile (toward the left side). The treatment here comprised 2 W of electrosurgical energy for 2 seconds, showing that moderate remodeling or partial treatments can be monitored, verified, and/or controlled using the electrical characteristics of the circuit of tissue identification system 510. Advantageously, once an appropriate frequency or range of frequencies has been determined, the entire tissue signature profile need not be generated for analysis of ongoing tissue treatments and/or characterization of tissues, as offsets can be readily identified. Such measurements may, for example, allow tissue temperatures to be determined, particularly where the temperature is a treatment temperature that alters an offset of the tissue signatures. The energy of the electrical signals used for tissue analysis will typically be less than the remodeling treatments. A similar plot is shown in FIGS. 31C and 31D, with the post-treatment correlation here being after treatment with 2 W for 9 seconds and 1 W for 9 seconds, respectively.

Figure 31E:
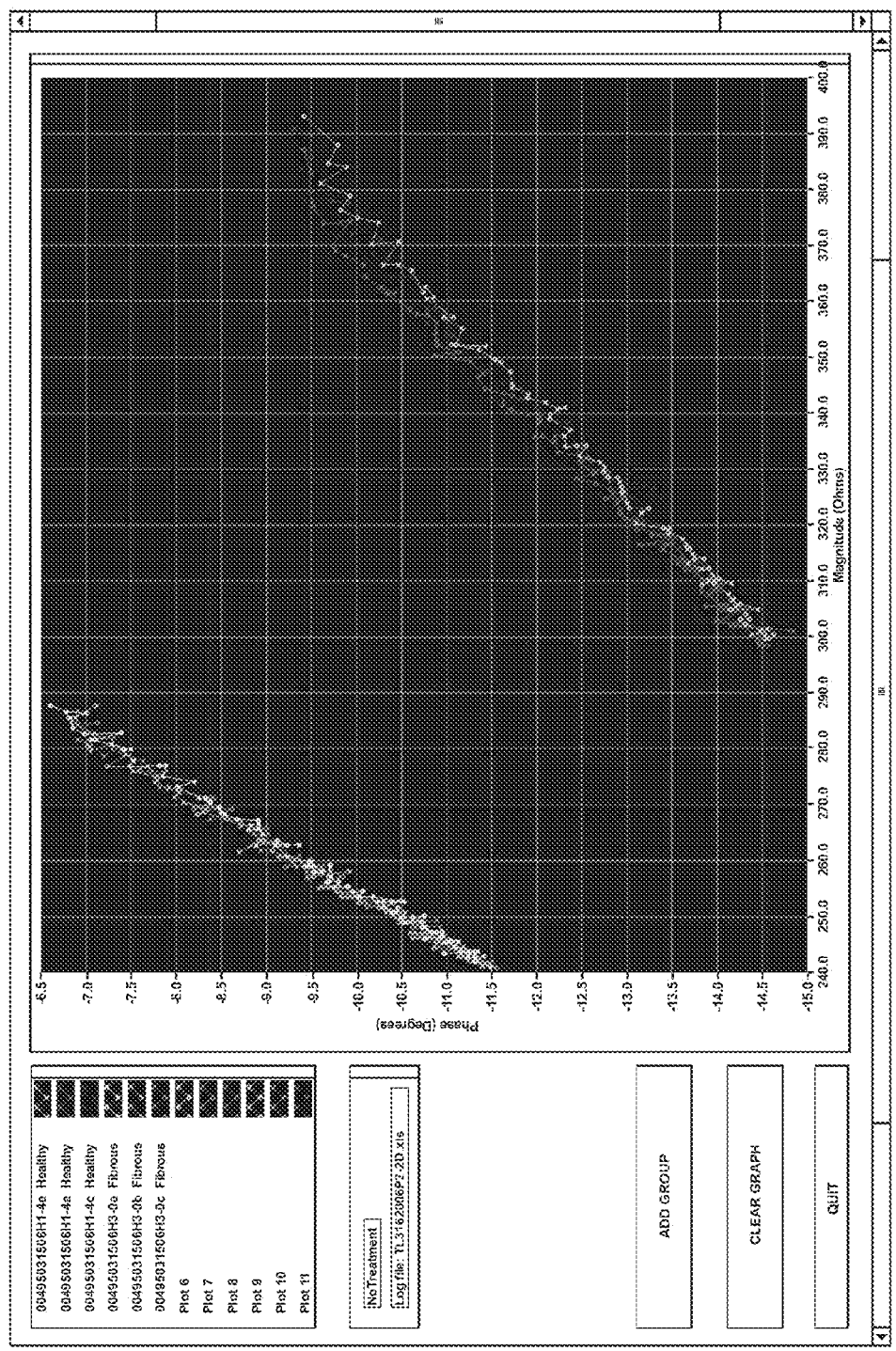
Figure 31F:
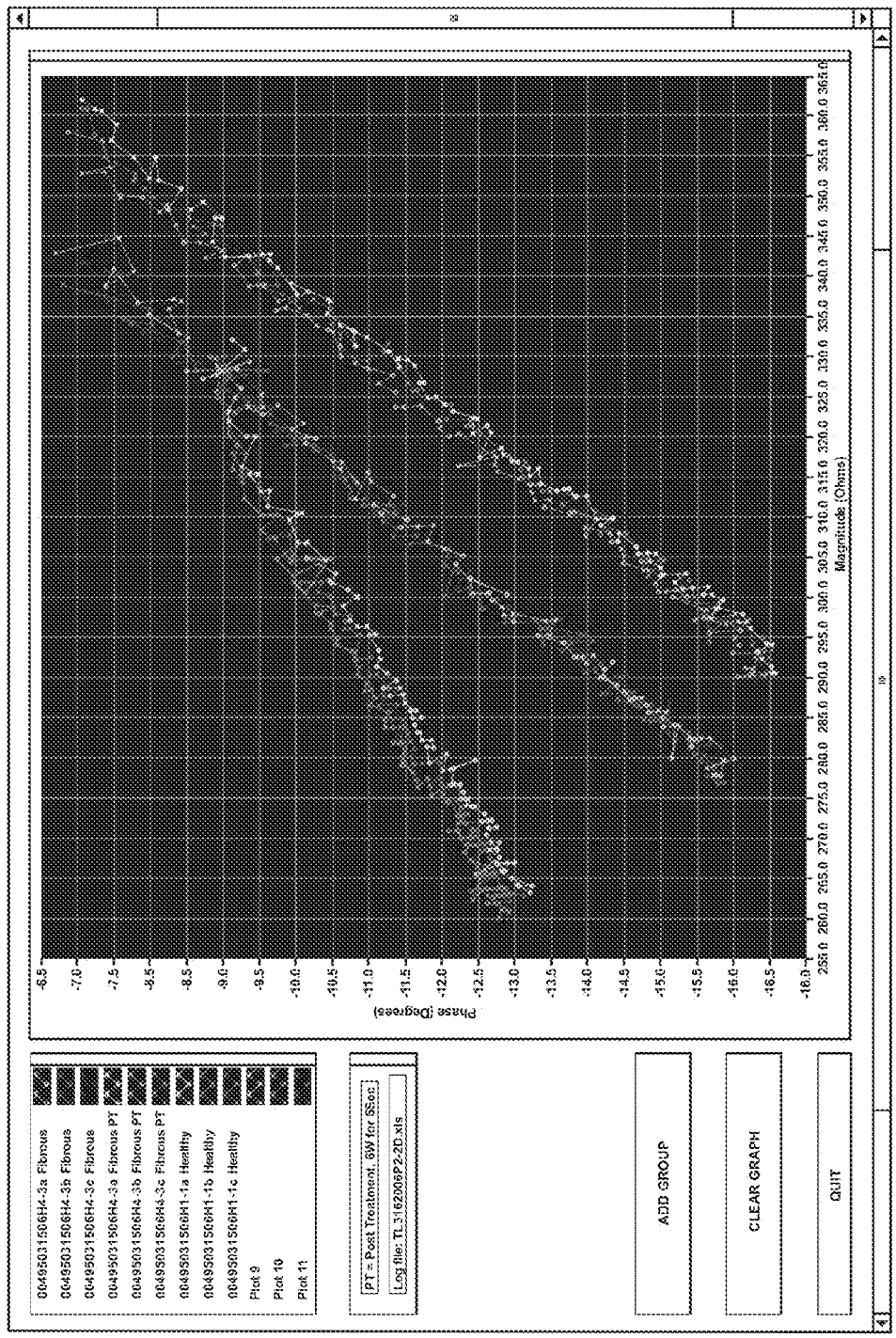
Figure 31G:
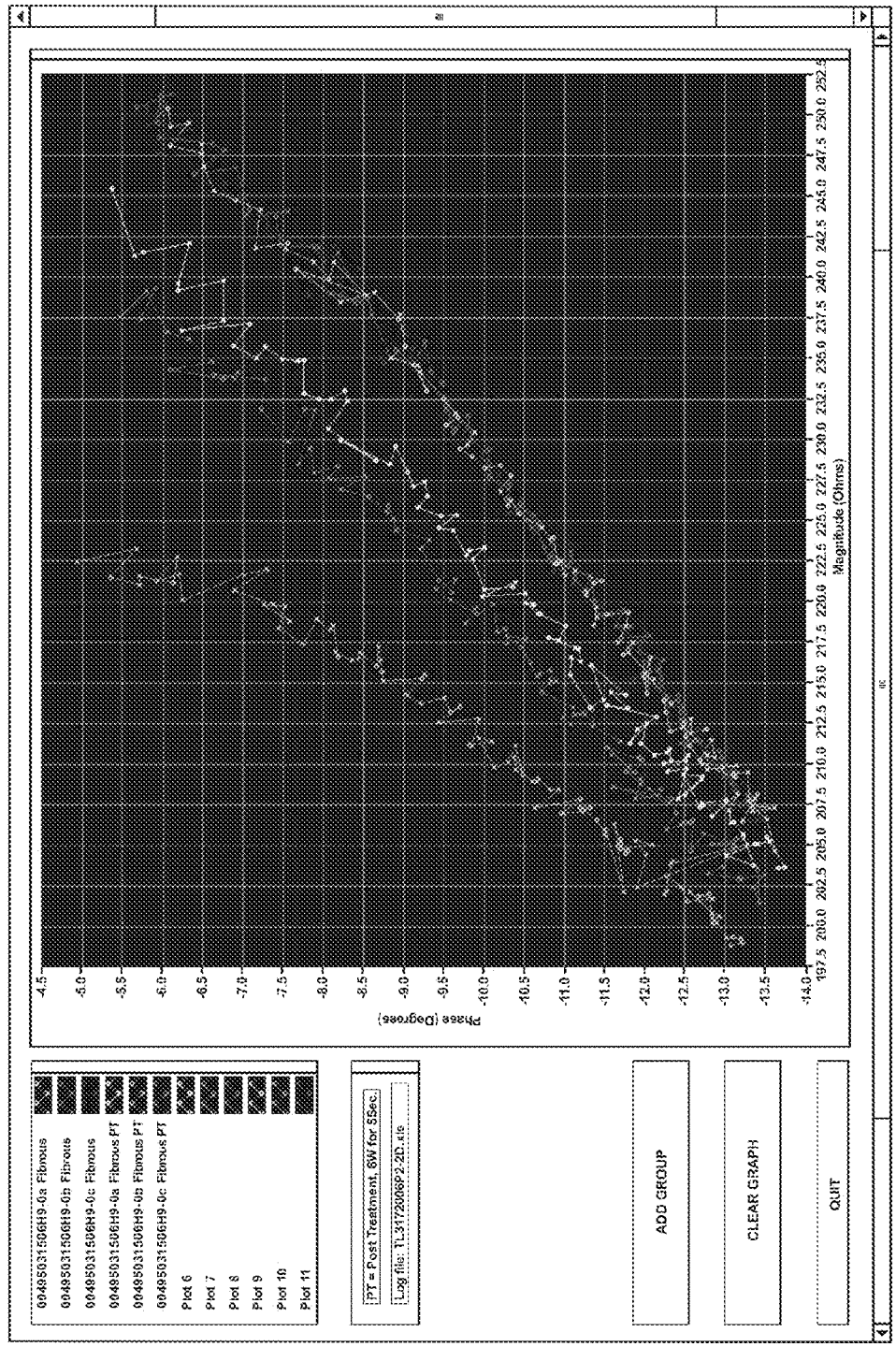
Figure 31H:
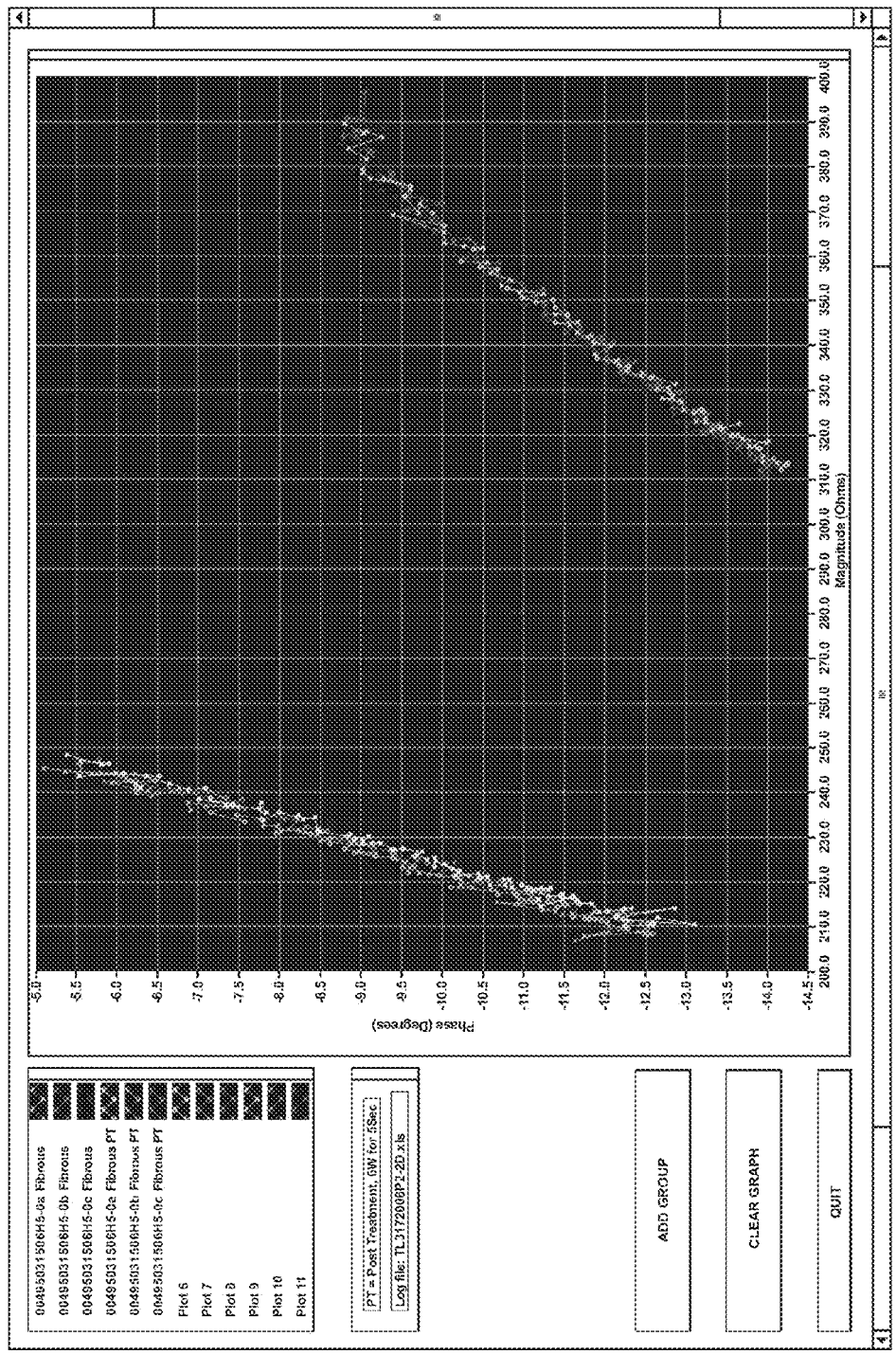
Figure 31I:
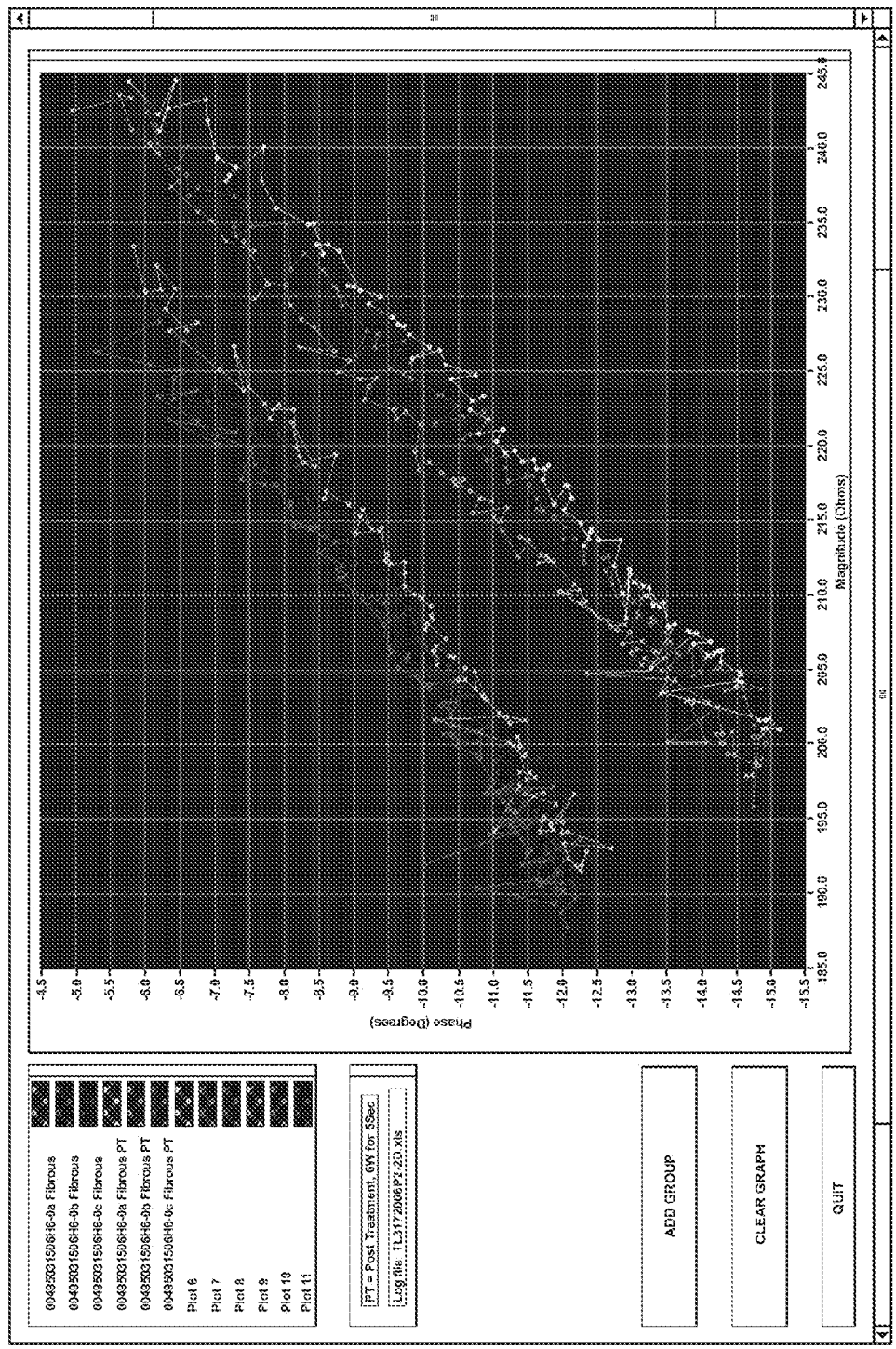
Figure 31J:
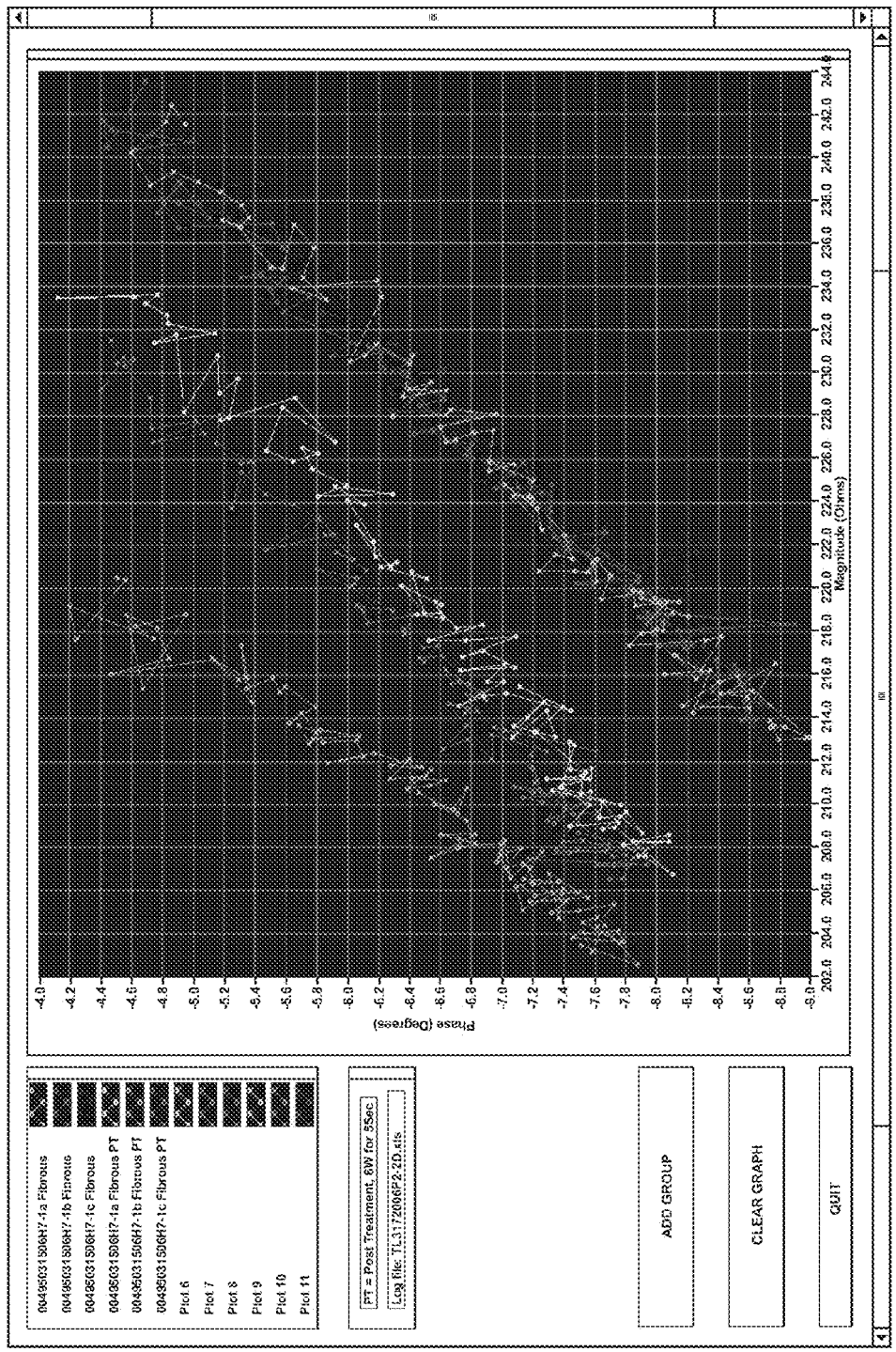

Referring now to FIG. 31E, relationships between healthy tissue (toward the right) and fibrous plaques (toward the left) can be identified from their associated tissue signature profiles or correlations, which differ significantly in both slope and magnitude. FIG. 31F shows relationships between correlations or profiles for fibrous tissue before treatment (left), fibrous tissue after treatment (right), and healthy tissue (center). FIGS. 31G-31J illustrate additional plots of relationships between profiles or correlations associated with fibrous tissues and treated fibrous tissues.

Figure 32:
FIG. 32 illustrate a variety of tissues for characterization and selective treatment by the system of FIG. 2.

Referring to FIG. 32 a severely diseased blood vessel with three basic categories of plaque can be seen: lipid rich (fatty) plaque, fibrous plaque, and calcified plaque or tissue. All may be present in one sample, and may also be present in the diseased tissue of (or adjacent to) one lesion, making the lesion hard to treat using conventional techniques. Through the tissue analysis techniques described herein, the correct prescription and dosage of energy can be targeted and delivered to effect a safe and appropriate (and often different) remodeling of the different tissue categories or types, at the appropriate locations of the constituent parts that make up each lesion.

Figure 32A:
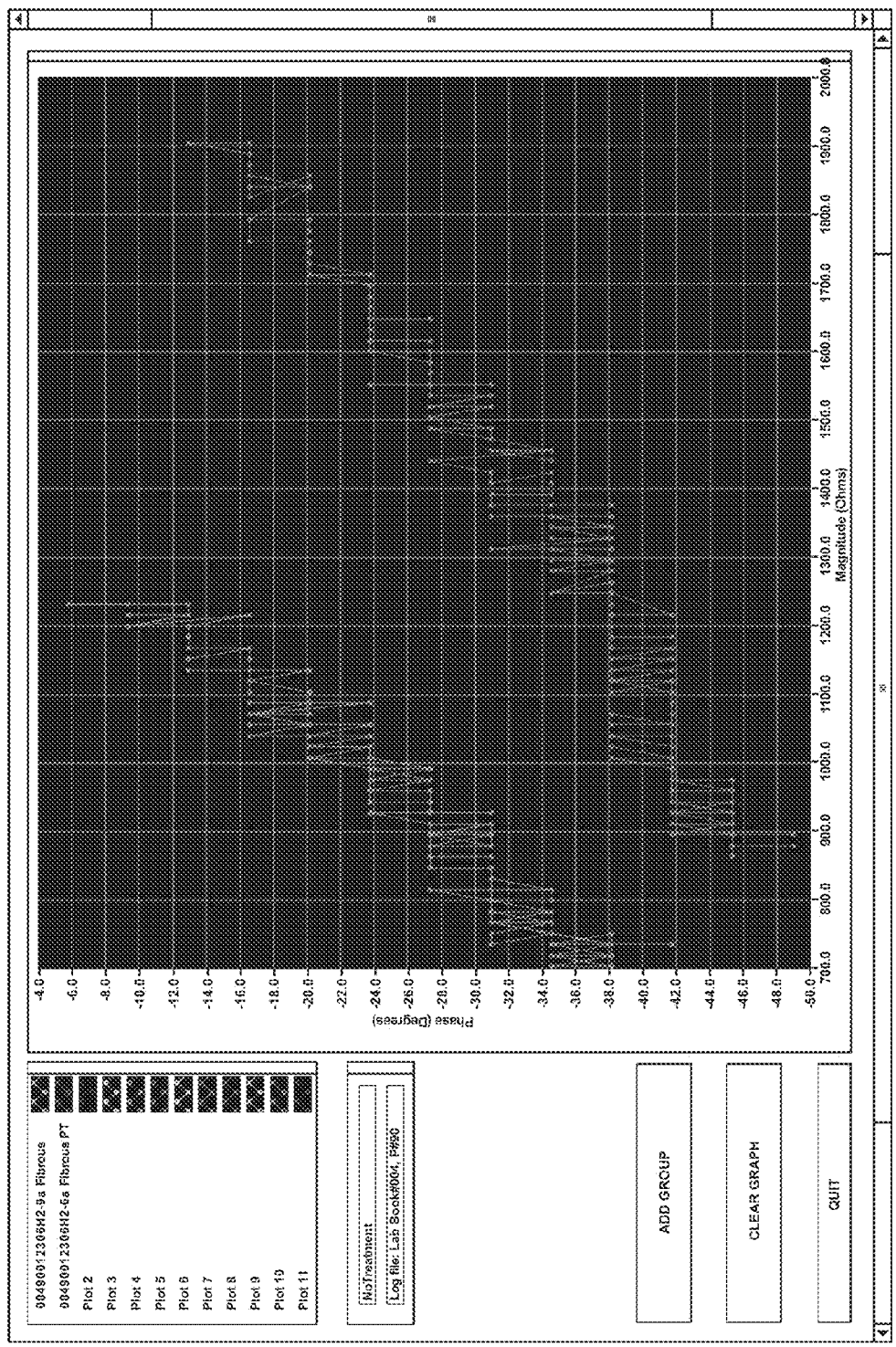
FIGS. 32A-32C illustrate changes in a relationship between phase angle and impedance in a frequency range associated with treatment of a tissue, along with histological images of the tissue before and after treatment.
Figure 32B:
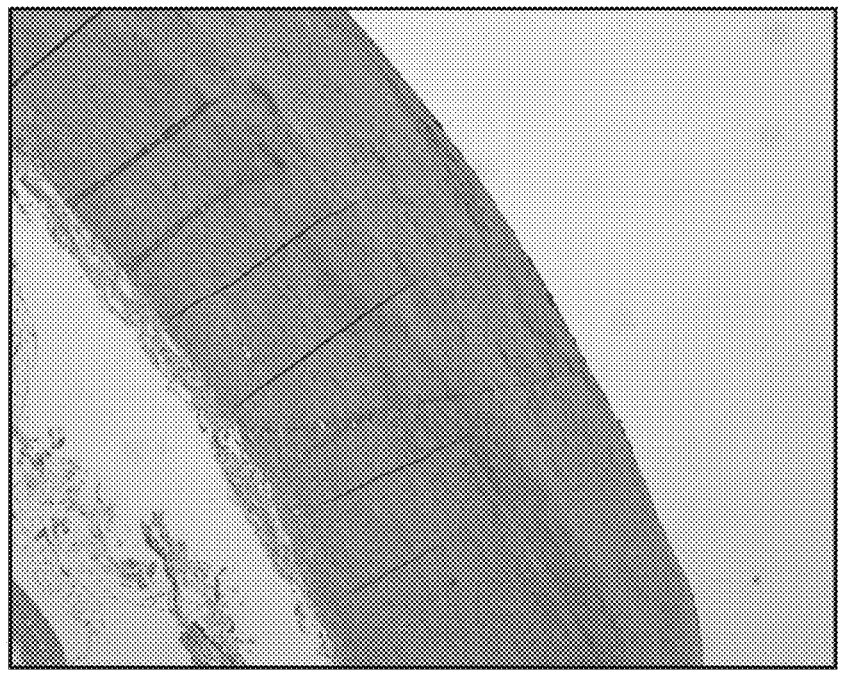
Figure 32C:

Referring now to FIG. 32A, this graph shows tissue signature measurements and tissue signature profile results obtained from a human aorta specimen, with these results for an engaged fibrous plaque before and after treatment. FIGS. 32B and 32C show histopathology slides of the tissue. The cracks visible on each slide may be artifacts of the mounting process. The nucleation or voids that show up in FIG. 32C, however, may indicate a remodeling of the tissue itself.

Figure 33:
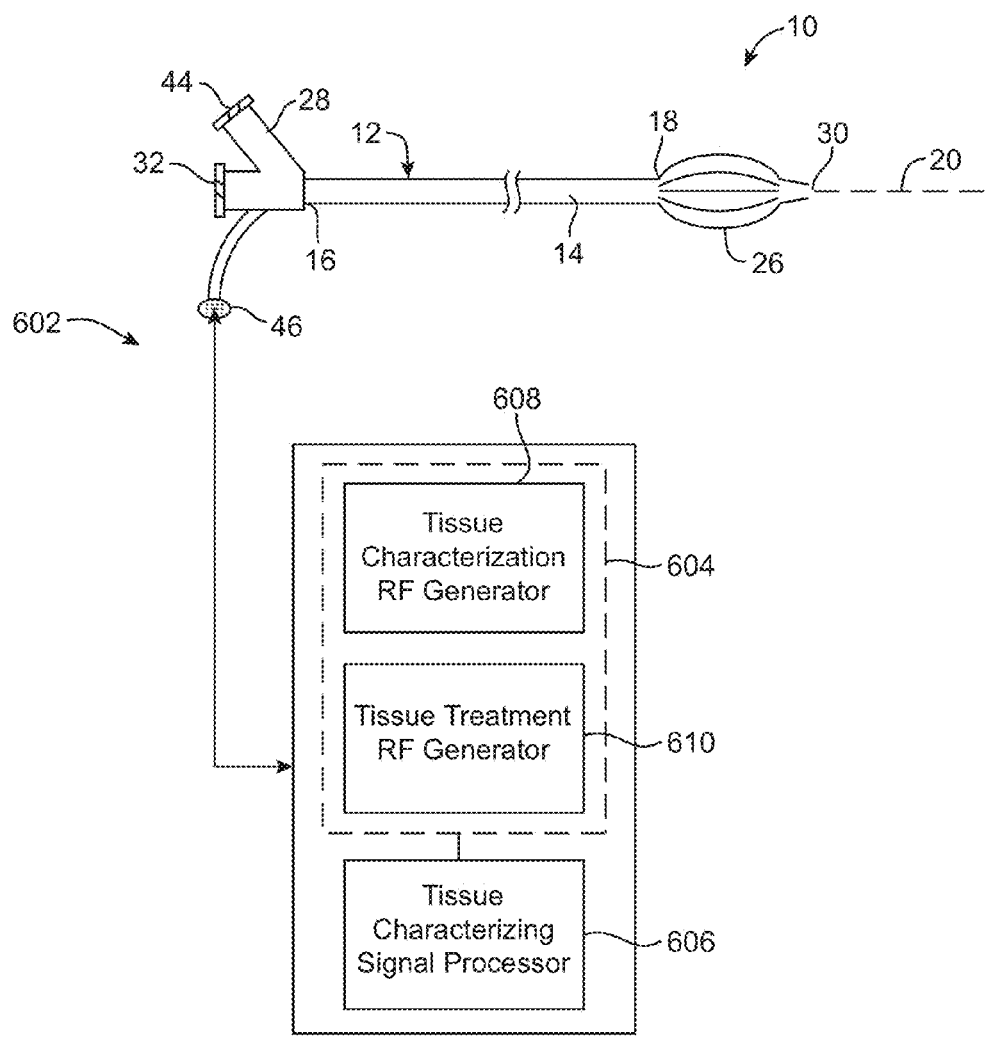
FIG. 33 schematically illustrates an exemplary embodiment of a system for characterizing a target tissue based on a frequency, impedance, and phase angle relationship, and for selectively treating the target tissue by applying a treatment potential that compensates for the phase angle of the target tissue.

Referring now to FIG. 33, an exemplary system 602 makes use of any of the probes described above (or any of a variety of alternative probes having electrodes) to characterize and selectively treat target tissues. The system includes an RF energy source 604 coupled to a processor 606. RF source 604 may have a relatively low power tissue characterization RF generator 608 and a higher power tissue treatment RF generator 610. Alternative embodiments may use the same circuitry for generating tissue characterization energy as for generating treatment energy, with the two treatment forms generally being applied in different modes.

Processor 606 of system 602 will often characterize tissues using a tissue signature profile correlation, as generally described above. In addition, processor 606 will determine an appropriate treatment energy form to selectively treat the target tissue or enhance the treatment of the target (tissue while limiting or inhibiting collateral tissue) damage. To provide these benefits, processor 606 will generally determine a frequency for the RF treatment energy and/or a phase of the RF treatment energy.

Figure 33A:
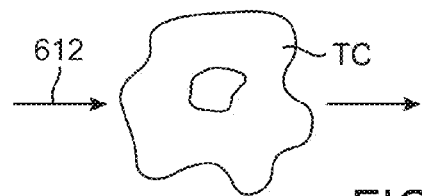
FIGS. 33A and 33B schematically illustrate a cell of a target tissue and an associated electrical circuit diagram of that tissue, respectively.
Figure 33B:
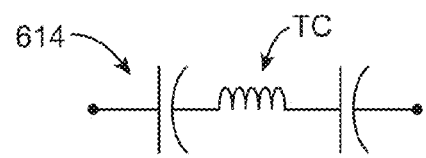

Selection of appropriate energy forms for heating of the target tissue may be generally understood with reference to FIGS. 33A and B and 34A and B. Referring first to FIGS. 33A and B, a target cell TC through which an RF current 612 passes may be represented by an electrical circuit model 614, as illustrated in FIG. 33B. Target cell model 614 includes a pair of capacitors (roughly corresponding with the cell walls) between which there is an inductor and/or resistor. Model 614 may help explain the characteristic relationship between frequency, impedance, and phase angle of a tissue, as cells of the same type may have generally similar individual electric circuit models with generally similar characteristics. Cells of different types may be modeled using the same types of electrical components, but the different cell types may have cellular walls with generally greater (or lesser) abilities to act as a capacitor, generally lower (or higher) resistances, and so on. Hence, while there may be significant variation among cells of the same type, the differences between different types of cells can be sufficient for the tissues to generate differing tissue signature profiles.

Figure 34A:
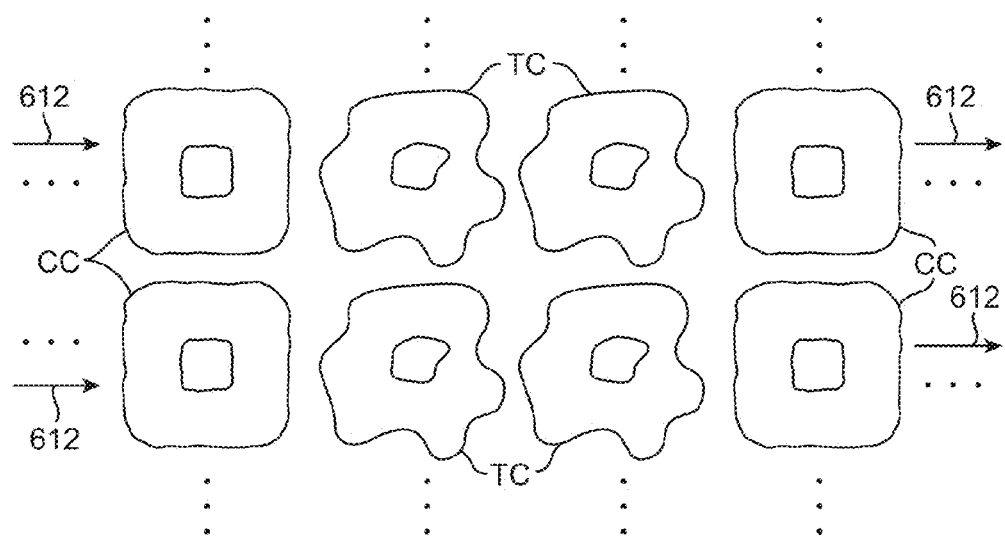
FIGS. 34A and 34B schematically illustrate a region of target tissue cells within a collateral tissue and an associated circuit diagram in which the target tissue cells and collateral tissue cells are included in a circuit with a probe and power source within the system of FIG. 33.
Figure 34B:
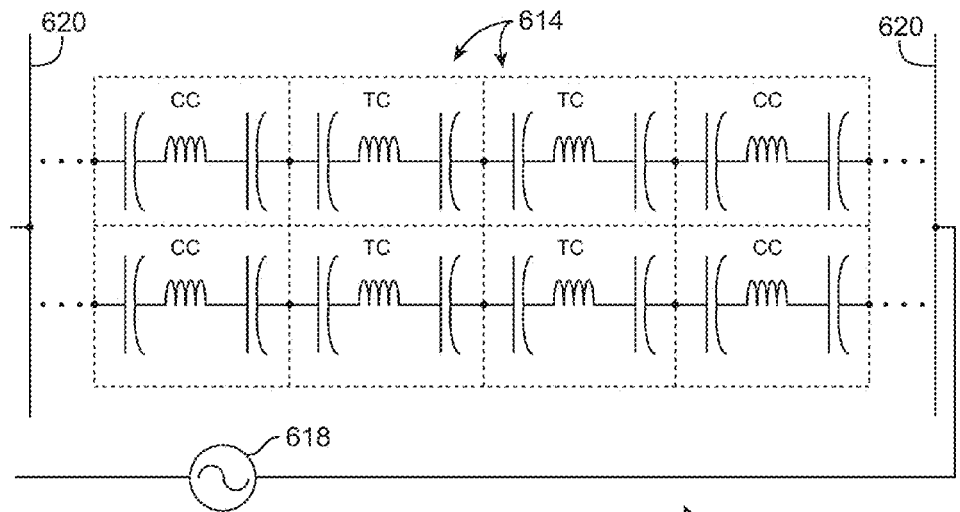

As illustrated in FIG. 34B, were electrodes to be applied on either side of a single target cell TC, the individual cell's electrical characteristics may produce a signature profile having differing phase angles and impedances associated with differing frequencies. A frequency could be selected for applying energy to the cell, and based on the relationship between frequency and phase angle, the power applied to the cell could be adjusted in phase to enhance the efficiency of heating that particular cell. For example, if at a given frequency, target cell TC has a phase angle of −14°, applying energy with a +14° phase angle could more effectively heat target cell TC than simply applying a standard zero phase angle RF energy at that frequency.

As can be understood with reference to FIGS. 34A and 34B, electrosurgical energy is typically applied to a number of cells simultaneously. In a given tissue structure, a three-dimensional volume of target cells TC may be disposed within a matrix of different collateral cells CC. A treatment current 612 may in part pass through both collateral cells CC and target cells TC in series, and may in part pass through these different cell types in parallel. Regardless, each individual cell included in a circuit 616 with a power source 618 and electrodes 620 may still be modeled as having similar simple electrical component models 614. Hence, the target cells 614 included in circuit 616 will be more efficiently and/or effectively heated by RF energy at a given frequency if the phase angle of power source 618 is appropriate for the target cell signature. As collateral cells CC may have significantly different characteristic phase angles at that frequency, they may be heated to a significantly lower extent than the target cells TC.

The model of FIGS. 34A and 34B is a simplification. For example, along with energizing each of the individual cells with electrical RF energy, heat flow will occur from the hotter cells to the adjacent cooler cells. Additionally, the target cells may have differing specific heats, electrical characteristics, and the like which make selective heating of the target cells challenging. Nonetheless, by selecting the appropriate phase angle, heating of the target cells may be enhanced. Additionally, by selecting frequencies at which the phase angles of the target cells differ significantly from the characteristic phase angles of the collateral cells, the selective heating benefits may be enhanced. Hence, referring to FIG. 31F, it may be advantageous to select a treatment frequency at which a collateral tissue signature profile (shown in green at the top of the chart) has a low phase angle while the tissue signature profile of a target fibrous tissue before treatment (shown in blue in the middle of the chart) has a high phase angle.

A variety of refinements may be included in the structure of system 602 and its use. Tissue characterization RF generator 608 may optionally comprise any of a wide variety of off the shelf variable frequency signal generators. Alternative proprietary variable frequency RF signal generators may also be used. Tissue treatment generator 610 will also typically comprise a variable frequency RF source, components and technology of which are well known and understood. The treatment RF generator source 610 may have a different or lower power than many existing variable frequency RF signal generators, so that a proprietary structure may be beneficial.

Processor 606 may be coupled to the circuits powered by the RF source(s) 604, 608, 610 by suitable sensors for monitoring the phase angle, magnitude, and the like to facilitate tissue type characterization. Processor 606 will also often transmit command signals to the RF source(s) so as to effect tissue characterization, to effect tissue treatment, to provide a user interface with the user of system 602, to integrate data regarding tissue types and treatment from system 602 with information from other tissue characterization and/or imaging modalities, and the like. As noted above, the target cell tissue signature profile may be altered during treatment. Hence, the processor 606 may intermittently interrupt tissue treatment to characterize the target tissue and/or monitor treatment. Processor 606 may modify the treatment frequency and/or phase angle in response to measured or estimated changes in the target tissue signature profile caused by the treatment. Processor 606 may also, for example, select frequencies and/or phase angles that differ somewhat from the ideal values for treatment of the target tissues so as to further limit heating of collateral tissues, or may select a convenient frequency (such as those designated by the Federal Communication Commission) to limit interference with radio communication systems, even though alternative frequencies may provide more selective heating of the target tissue and/or more limited injury to a collateral tissue. To limit interference with radio communication systems in general, some or all of the components of the system 602 may be shielded, such as by using the system in a room or enclosure which limits the escape of RF signals.

Figure 35:
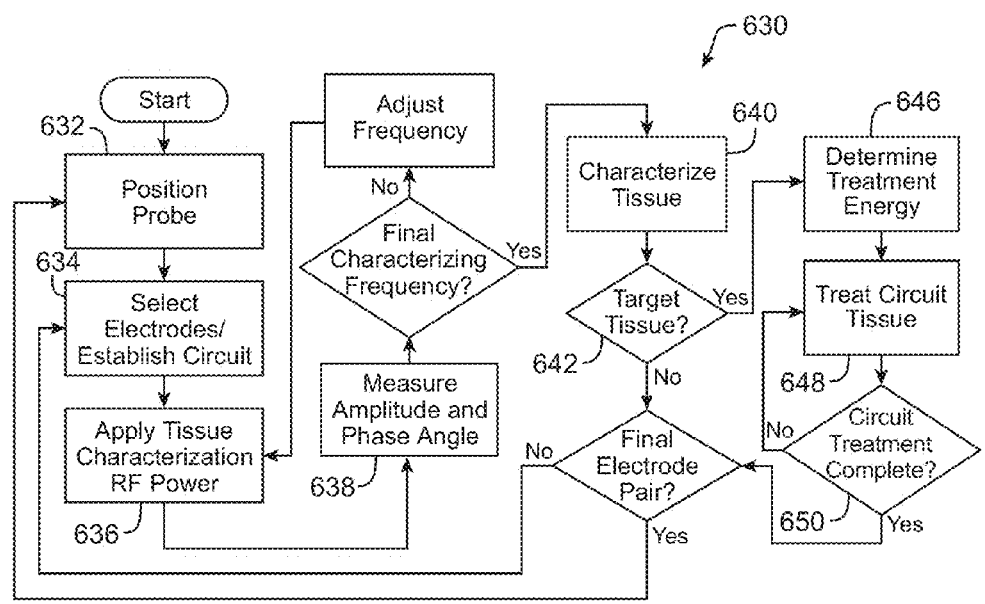
FIG. 35 is a flowchart schematically illustrating a method for characterizing a target tissue and selecting a form of electrical energy to enhance the treatment of the target tissue and inhibit injury to a collateral tissue using the system of FIG. 33.

Referring now to FIG. 35, an exemplary method 630 is shown schematically as starting with positioning of a probe 632. Prior to, during, and/or after positioning of the probe for the first time, the probe may be introduced into the body, electrodes of the probe may be deployed, and/or the like, as can generally be understood with the treatment methodology described above.

An electrical circuit is established 634. For probes having a plurality of alternative electrode pairs, the electrical circuit may be established by selecting one or more electrodes of the pair. Characterization and treatment will often be facilitated by positioning the electrodes near a target tissue and driving bipolar electrical alternating energy between the selected electrodes. Alternate embodiments may use monopolar probes.

A tissue characterization RF power 636 may be applied to the circuit, and an impedance amplitude and phase angle measured or determined 638. The measured amplitude and phase angle may be recorded and associated with a circuit frequency, and additional measurements taken until the desired data have been recorded.

Once the desired characterizing information has been obtained, the tissue can be characterized 640. If the characterized tissue is targeted for treatment 642, the appropriate treatment energy may be determined 646. If the characterized tissue is not targeted for treatment, an alternative pair of electrodes of the probe may be selected for tissue characterization, and/or a probe may be repositioned to a new location.

Determination of the treatment energy 646 will often comprise selecting a frequency and associated phase angle which compensates for the characteristic and/or measured phase angle of the target tissue. For example, if the target tissue has a characteristic or measured phase angle of −16° at a suitable treatment frequency, and if collateral tissues have phase angles of about −3° at that frequency, the determined treatment energy may have the frequency and a phase angle of +16° so that when electrical energy is converted to heat energy, the area under the superimposed voltage and current curves (when plotted on a magnitude vs. time graph) is enhanced or maximized.

The circuit is energized 648 so as to treat the tissue included within the circuit, often to heat the target tissue to a desired temperature and/or for a desired time so as to provide the desired therapeutic result. The system may determine whether treatment is complete by recharacterizing the tissue as described above, or based on dosimetry or the like. If the circuit treatment is complete 650, additional electrode pairs may be characterized and/or treated, and/or the probe may be moved to a new position. Once the final probe position has been treated, the treatment method can be halted.

Figure 36:
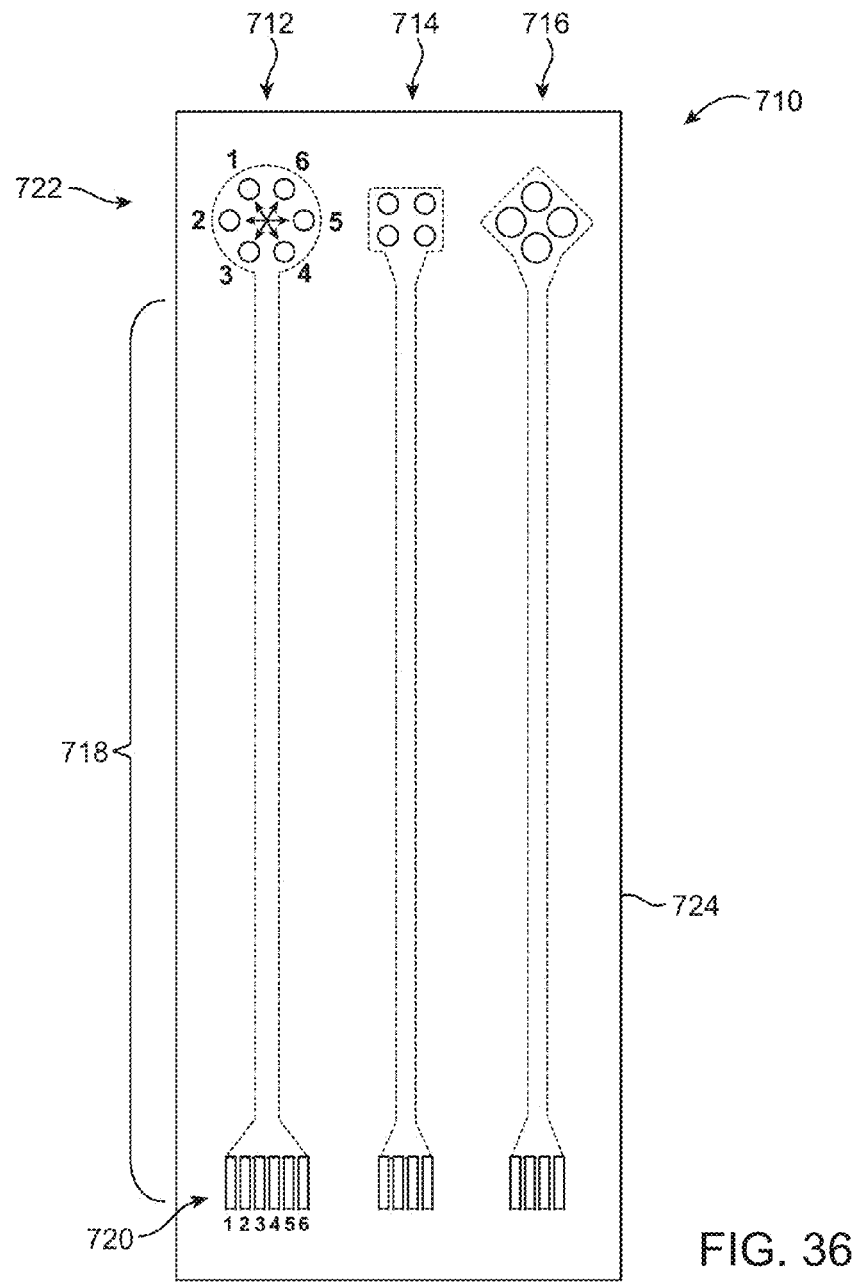
FIG. 36 shows 3 flex circuit structures which can each electrically couple a plurality of proximal electrical contacts with a plurality of electrode surfaces supported by an expandable balloon of a balloon catheter for use in embodiments of the invention, along with notations that can be used to understand an example of multiplexing of the electrodes.

Referring now to FIG. 36, an exemplary flex circuit panel 710 having flex circuits 712, 714, and 716 is shown. Each of the flex circuits include electrically conductive leads 718 that extend between proximal electrical contacts 720 and distal electrodes 722. Leads 718 are supported by a flexible polymer substrate 724, and the flex circuits may be used in catheter 12

(see FIG. 33), for example, by cutting the substrate around and/or between the electrical components of the circuit, mounting the electrodes to a radially expandable structure 26 (such as a basket or balloon), and extending leads 718 toward and/or along catheter body 14 for electrical coupling to processor 606 and RF source(s) 604, 608, and/or 610. One or more flex circuits may be mounted to the expandable structure, with the electrodes of each flex circuit optionally providing a grouping or sub-array of electrodes for treating an associated portion or region of a target tissue. Alternative sub-arrays may be provided among electrodes of different flex circuits, may be defined by programmable logic of the processor, and/or may comprise any of a wide variety of alternative electrode circuit structures, with the sub-arrays often being employed for multiplexing or treating the region of target tissue with a plurality of differing electrical energy paths through the tissue.

Still referring to FIG. 36, multiplexing between selected electrodes of an array or sub-array can be effected by selectively energizing electrode pairs, with the target tissue region for the sub-array being disposed between the electrodes of the pairs so that the energy passes therethrough. For example, a pair of electrodes selected from electrodes 1, 2, 3, 4, 5, and 6 of flex circuit 712 (with the selected electrodes optionally being positioned opposite each other) may be energized and then turned off, with another pair then being energized, and so forth. The firing order might be 1 and 4, then 2 and 5, then 3 and 6. Bipolar potentials between the electrodes of the pair can induce current paths in the same general tissue region, with the power dissipated into the tissue optionally remaining substantially constant. This provides a duty cycle of about ⅓ with respect to heat and/or losses at each electrode surface. The four electrode configurations of flex circuits 714 and 716 could be used in a similar manner with a 50% duty cycle. Monopolar energy might also be applied using a larger ground pad on the skin of the patient or the like, with the duty cycle optionally being cut in half relative to bipolar energy.

Some embodiments of the vascular treatment devices, systems, and methods described herein may be used to treat atherosclerotic disease by gentle heating in combination with gentle or standard dilation. For example, an angioplasty balloon catheter structure having electrodes disposed thereon might apply electrical potentials to the vessel wall before, during, and/or after dilation, optionally in combination with dilation pressures which are at or significantly lower than standard, unheated angioplasty dilation pressures. Where balloon inflation pressures of 10-16 atmospheres may, for example, be appropriate for standard angioplasty dilation of a particular lesion, modified dilation treatments combined with appropriate electrical potentials (through flex circuit electrodes on the balloon, electrodes deposited directly on the balloon structure, or the like) described herein may employ from 10-16 atmospheres or may, surprisingly, be effected with pressures of less than 5 atmospheres, optionally being less than 3 or 2 atmospheres, in some cases with an inflation pressure of about 1 atmosphere. Such moderate dilations pressures may (or may not) be combined with one or more aspects of the tissue characterization, tuned energy, eccentric treatments, and other treatment aspects described herein for treatment of diseases of the peripheral vasculature.

Still further refinement may be included in the methods and devices described herein. For example, the energy applied to an inner wall of a blood vessel may be varied axially and circumferentially about the vessel wall in response to variations in the thickness of plaques targeted for treatment. Where the tissue signature indicates that a target tissue is present at first and second locations, and where the tissue signature or an alternative diagnostic modality (such as intravascular ultrasound, optical coherence tomography, or the like) indicates that a thickness of the target tissue at the first location is greater than a thickness of the target tissue at the second location, a greater amount of treatment energy may be directed to the first location than is directed to the second location.

Figure 37A:
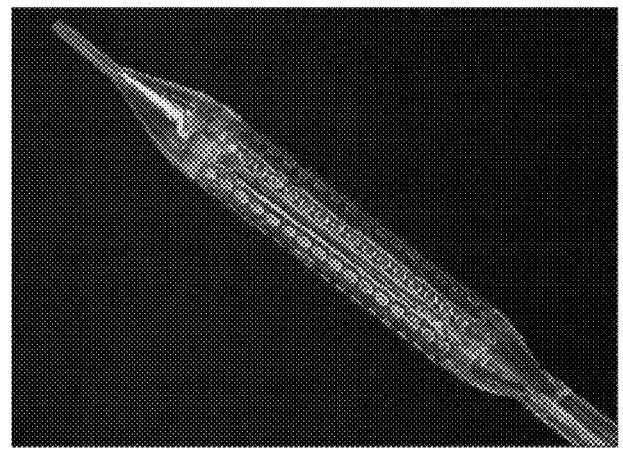
FIGS. 37A and 37B show an exemplary balloon catheter supporting electrodes and an exemplary RF generator structure, respectively, for use in the systems and methods described herein.
Figure 37B:

Referring now to FIG. 37A, an exemplary balloon catheter structure having an array of electrodes thereon can be seen. FIG. 37B illustrates an exemplary RF generator for energizing the electrodes of the balloon catheter of FIG. 37A. The balloon catheter and RF generator of FIGS. 37A and 37B were used in a series of experiments on animal models, with the balloons having diameter sizes ranging from about 3 mm to about 8 mm. The test subjects comprised Healthy domestic swine and Yucatan Mini-Swine. Atherosclerotic disease was induced (Injury & HFHC diet), to demonstrate the ability of a system including the balloon catheter and RF generator of FIGS. 37A and B to deliver controlled therapy to artery walls. Histology was obtained at post-treatment endpoints to determine the extent of tissue damage and the appropriate treatment dose ranges.

Two experimental branch options were included:
    Option 1: Injure swine arteries with balloon/3-5 months HFHC feed/treat with Minnow Catheter/Survive for 0-90 days
    Option 2: Treat healthy swine arteries with Minnow Catheter/Survive for 0-90 days Dose range and restenosis data were additional criteria.
    The target tissues were accessed and imaged as follows:
    Carotid cut down (to allow bilateral iliac and femoral arterial treatment)
    8F Cook Shuttle Sheath
    0.014"Cordis Stabilizer wire
    Boston Scientific 40 mHz IVUS catheter Catheter systems including the balloon catheter of FIG. 37A were used to treat selected treatment sites. Imaging was also performed using Ziehm, Siemens, and GE fluoroscopes. Additional experimental methods and materials included the following:
    Injury procedure (Fogarty balloon overstretch and denudation); survive up to 5 months
    Treat swine iliac/femoral artery; survive up to 90 days
    1-4 treatments per leg (average 3 per leg)
    Varied power/time protocols Data points were obtained using:
    Pre/Post Treatment Angiographic Evaluation
    Pre/Post Treatment IVUS Evaluation (majority)
    Pre Sacrifice Angiographic Evaluation
    Pre Sacrifice IVUS Evaluation (majority)
    Histopathology Distilled histopathology data were evaluated using the following criteria:
    Inflammation—all time points
        0=none
        1=scattered
        2=moderate infiltration
        3=aggregating
    Thrombus—only 7 day time points (n/a on <7 day time points)
        0=none-fibrin
        1=focal
        2=laminar
        3=thrombosis % Stenosis—begins to form at 14 days (n/a on 7 day time points)
0=0-25%
1=26-50%
2=51-75%
3=76-100%

Such distilled data may be among the most representative and/or predictive of actual treatment vessel results.

FIG. 38A summarizes the experiments that were performed. Certain treatment sites were excluded from the subsequent analysis based on the following criteria:
- (n=6) device malfunction (e.g., higher or lower power than intended, electrode delamination)
- (n=4) bussed electrodes—resulting in much higher power than anticipated
- (n=4) procedural complications (occlusions): 2 vessels were treated but distal vessels remained occluded from injury procedure (preventing distal flow and most likely resulting in occlusion of treated sites); 2 tandem sites severely dissected from injury procedure, most likely treated in false lumen
- (n=1) degenerated sample—tissue not fixed properly
- (n=7) no visible lesion (may be due to under-treatment, electrode conduction failure)
- (n=1) diffuse treatment—site treated twice (over-treated)

Figure 39:
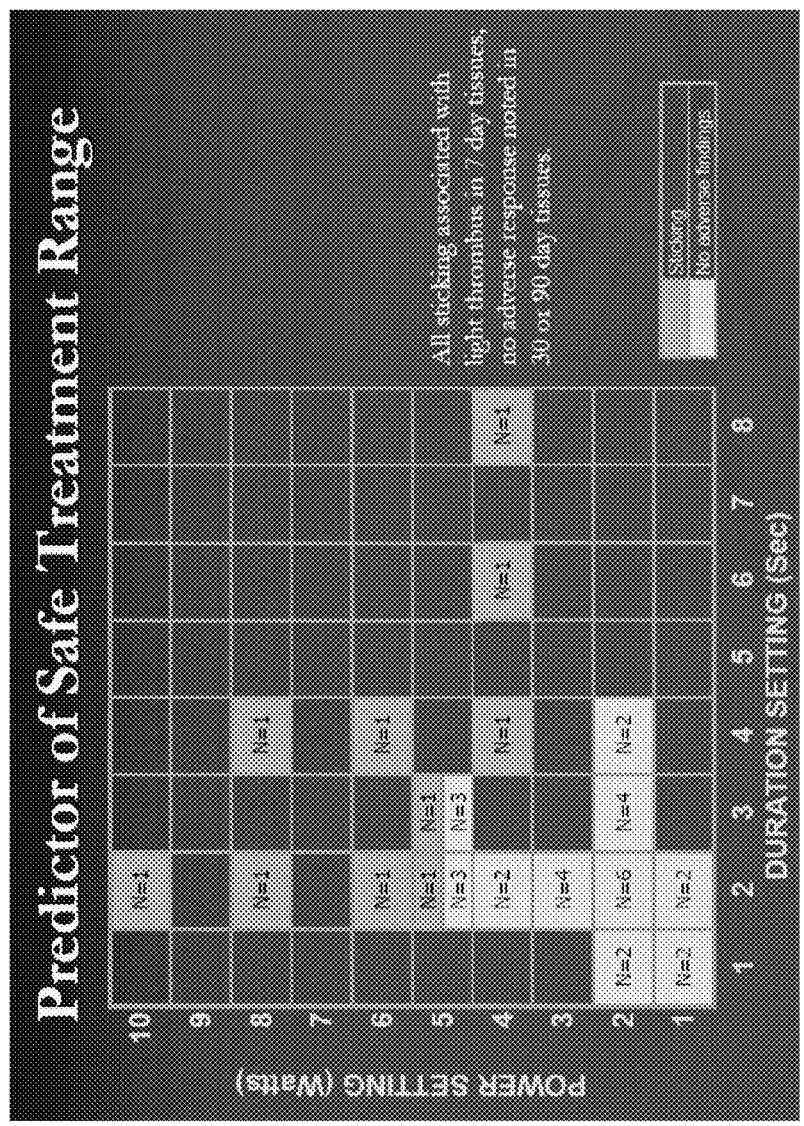
FIG. 39 shows effective treatment ranges of power and time identified using the experiments of FIG. 38A.

Total numbers of sites treated at each of a range of different powers and times are summarized in FIG. 38B. Safe and/or desirable treatment ranges or dosages for the animal treatment model are summarized in FIG. 39.

Figure 40A:
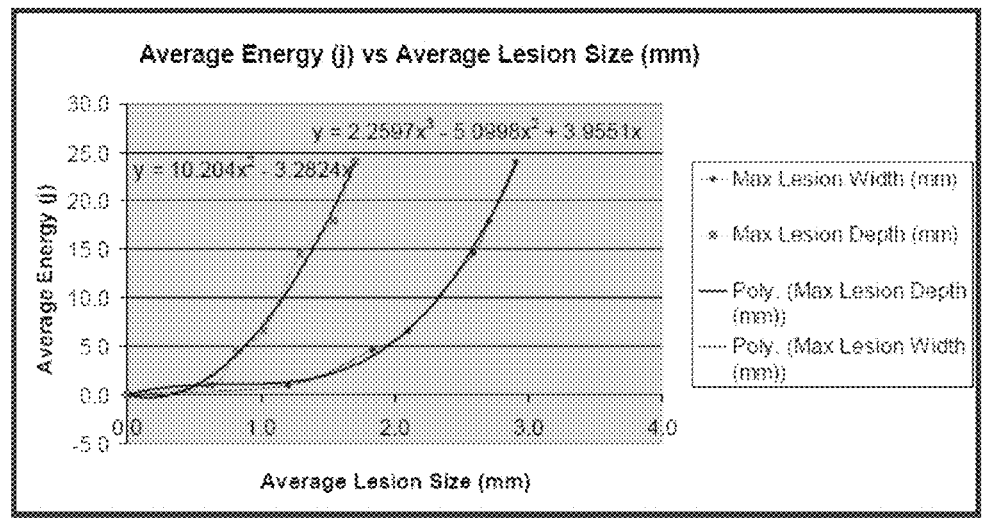
FIGS. 40A, 40B, 41, and 42 illustrate lesion sizes generated from the experiments.
Figure 40B:
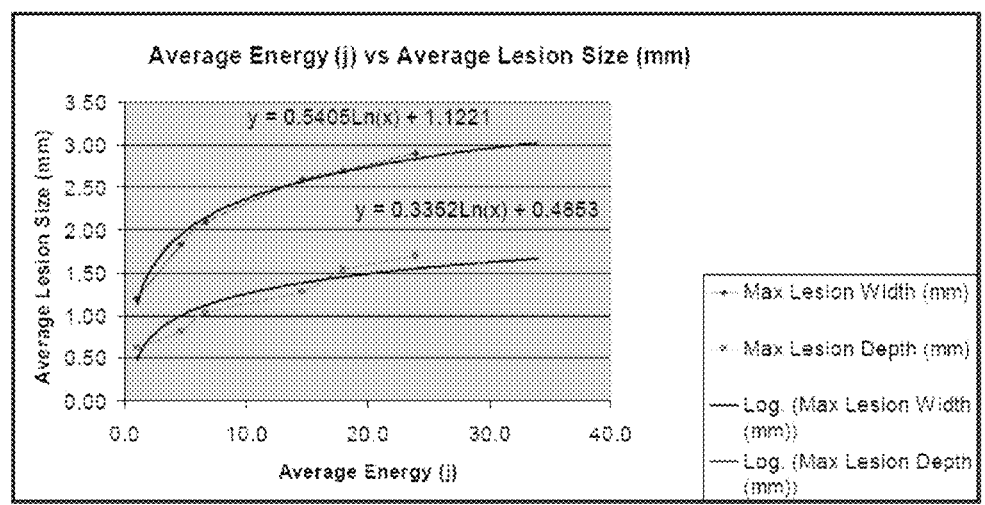
Figure 41:
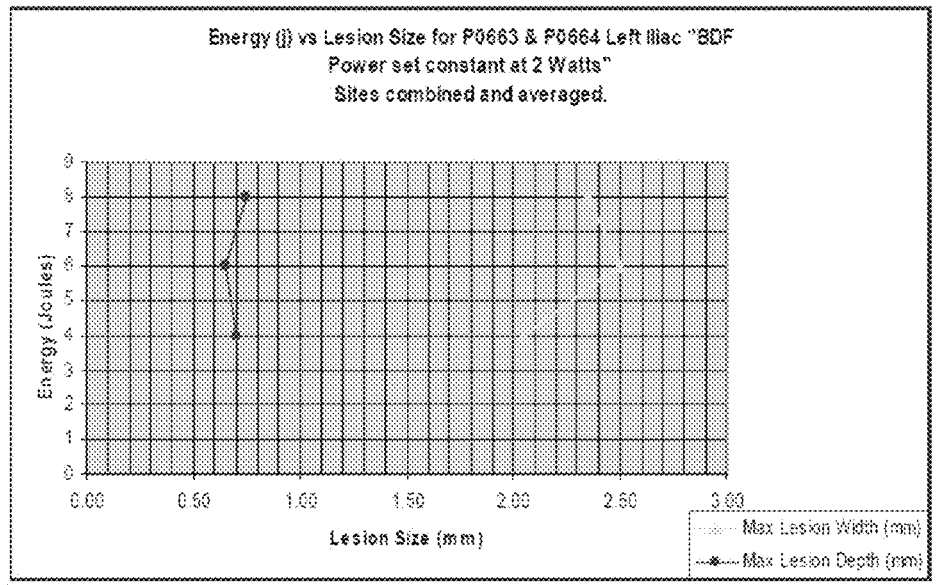
Figure 42:
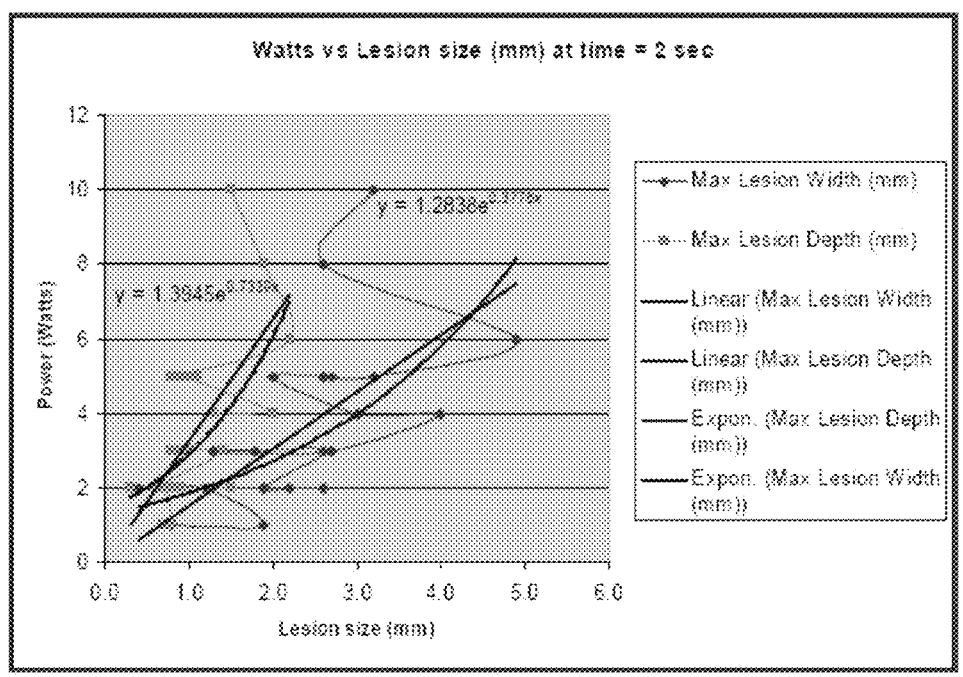
Figure 43:
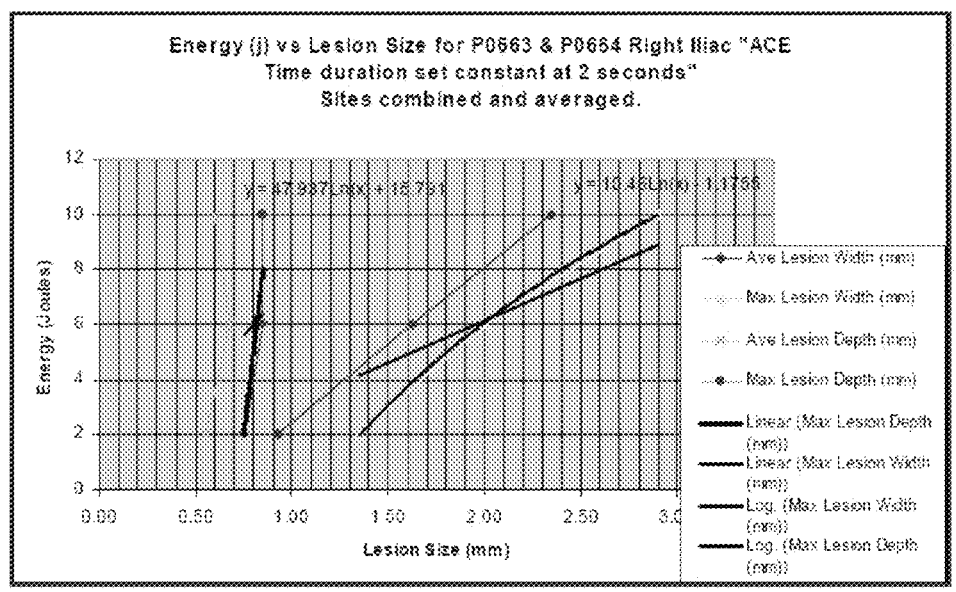
FIG. 43 illustrates additional lesion size data obtained from the experiments.

The size (depth and width) of lesions generated using different energies are summarized in FIG. 40A, while FIG. 40B illustrates average lesion size versus the average energy (forecasted). FIG. 41 illustrates, for treatments performed with a constant power (about 2 Watts), treatment energy as a function of lesion size. FIG. 42 illustrates, for a constant treatment time (of about 2 seconds), the relationship between treatment power and lesion size. A relationship between energy and lesion size when time is held constant (at 2 seconds) is seen if FIG. 43.

Figure 42A:
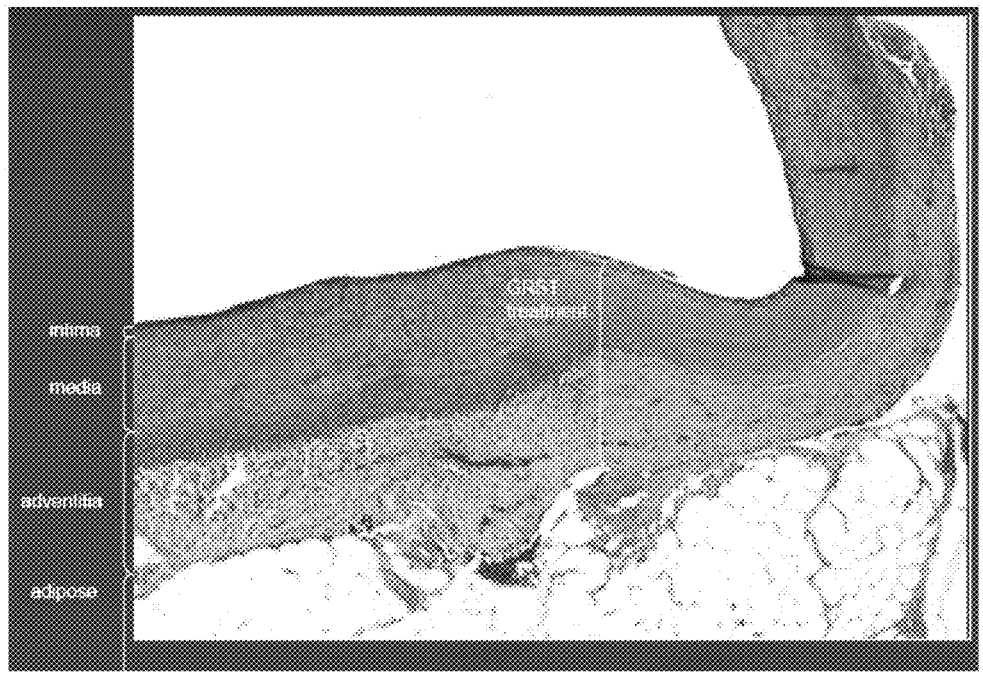
FIGS. 42A and 42B illustrate histology slides showing embodiments of treatments used in the experiments.
Figure 42B:
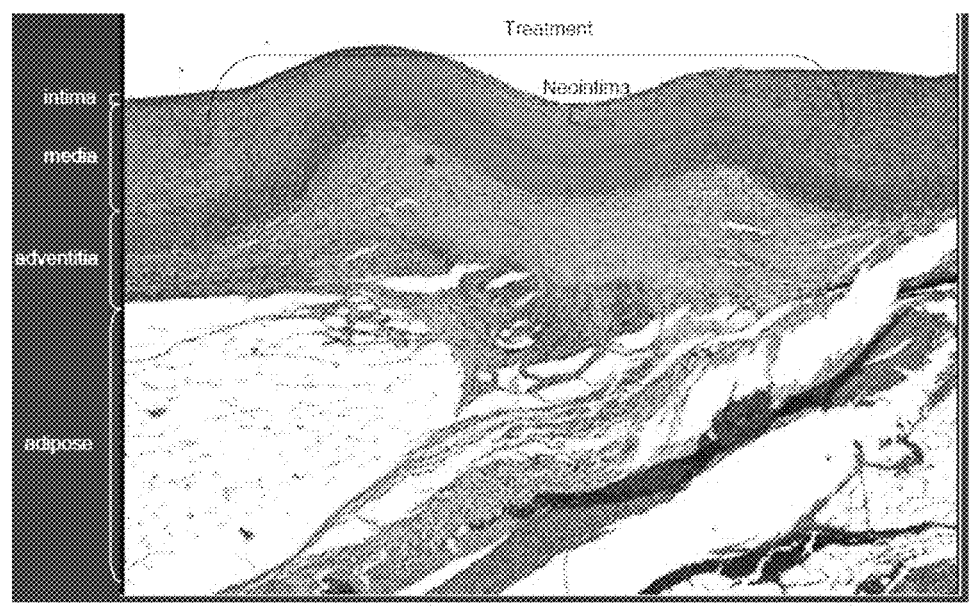

FIGS. 42A and 42B illustrate histopathology slides showing tissues of a vessel wall, and illustrate effects of some of the experimental embodiments of treatments on various tissue levels of the vessel wall.

In many embodiments, gentle heating energy added before, during, and or after dilation of a blood vessel may increase dilation effectiveness while lowering complications. In some embodiments, such controlled heating with balloon or other mechanical dilation may exhibit a reduction in recoil, providing at least some of the benefits of a stent-like expansion without the disadvantages of an implant. Benefits of the heating may be enhanced (and/or complications inhibited) by limiting heating of the adventitial later below a deleterious response threshold. Such heating of the intima and/or media may be provided using heating times of less than about 10 seconds, often being less than 3 (or even 2) seconds. Efficient coupling of the energy to the target tissue by matching the driving potential of the circuit to the target tissue phase angle may enhance desirable heating efficiency, effectively maximizing the area under the electrical power curve. The matching of the phase angle need not be absolute, and while complete phase matching to a characterized target tissue may have benefits, alternative systems may pre-set appropriate potentials to substantially match typical target tissues; though the actual phase angles may not be matched precisely, heating localization within the target tissues may be significantly better than using a standard power form.

Potentials driving a circuit for peak efficiencies in heating of the target tissues will not necessarily match minimized heating (or peak non-efficiencies) of the healthy collateral tissues. No single potential will even maximize desired heating, due in-part to the variability in the tissues in general, and due in-part to the various forms of disease tissues that may be present within the vessels. Healthy tissue may exhibit less variability in characteristics (including their phase angle characteristics) than the variety of different forms of vascular disease that might be targeted for treatment. For at least these reasons, it may be advantageous to select an electrical potential which is somewhat (or even very) inefficient at heating of the target tissue, so long as that energy heats the collateral tissue to a minimum or relatively low extent. In fact, a lack of efficiency in heating of the non-target tissues may be the primary aim in selecting an appropriate energy, as the energy can be negatively biased for heating the non-target tissues so that damage is inhibited when the target tissue is remodeled, even if the remodeling makes use of what would generally be considered a poor phase match to the target tissue. In such cases, the non-target tissue might be primarily, substantially, or even fully (to the extend possible) out of phase. Note that treatments of a patient may make use of a combination of phase matching energy to a target tissue for some tissues sites and/or a portion of a treatment, and phase mismatching to a non-target tissue for other sites and/or another portion of a treatment of the same site.

A variety of embodiments may take advantage of the structures and methods described herein, and may involve one or more of a variety of mechanisms for efficacy. For example, in some embodiments heating of collagen may unwind the triple helix, breaking the intermolecular cross-links of the hydrogen and disulfide bonds, thereby allowing remodeling and compaction to a gel-like state. Optionally, heating may melt lipids in fat cells, so that the fat cells shrink and the fatty acids (liquefied lipids) are expelled into the interstitial space. Proteins may be remodeled by breaking the ion-dipole, hydrogen, and Van der Waals bonds, thereby leading to the reforming and compaction of the denatured structure. In many embodiments, these or other mechanisms may occur or be initiated very quickly as the energy is absorbed, with substantial remodeling often taking place within about 2 seconds of initiation of the heating. Histological examination of treated tissues treated experimentally with the balloon-mounted electrode systems described herein has found, from 7 to 90 days post-treatment, absent/scant endothelium damage, absent/sparse/mild subendothelium inflammation, and absent/limited interstitial hemorrhage.

As the energies and powers for characterizing and/or treating tissues are relatively limited, the power source may optionally make use of energy stored in a battery, with the power source and/or associated controller optionally being contained within a hand-held housing. Use of such battery-powered systems may have benefits within crowded operating rooms, and may also help avoid inadvertent overtreatment. The batteries may be disposable structures suitable to be included in a kit with a single-use catheter, while the processor circuitry may be re-useable. In other embodiments, the batteries may be rechargeable.

Figure 44A:
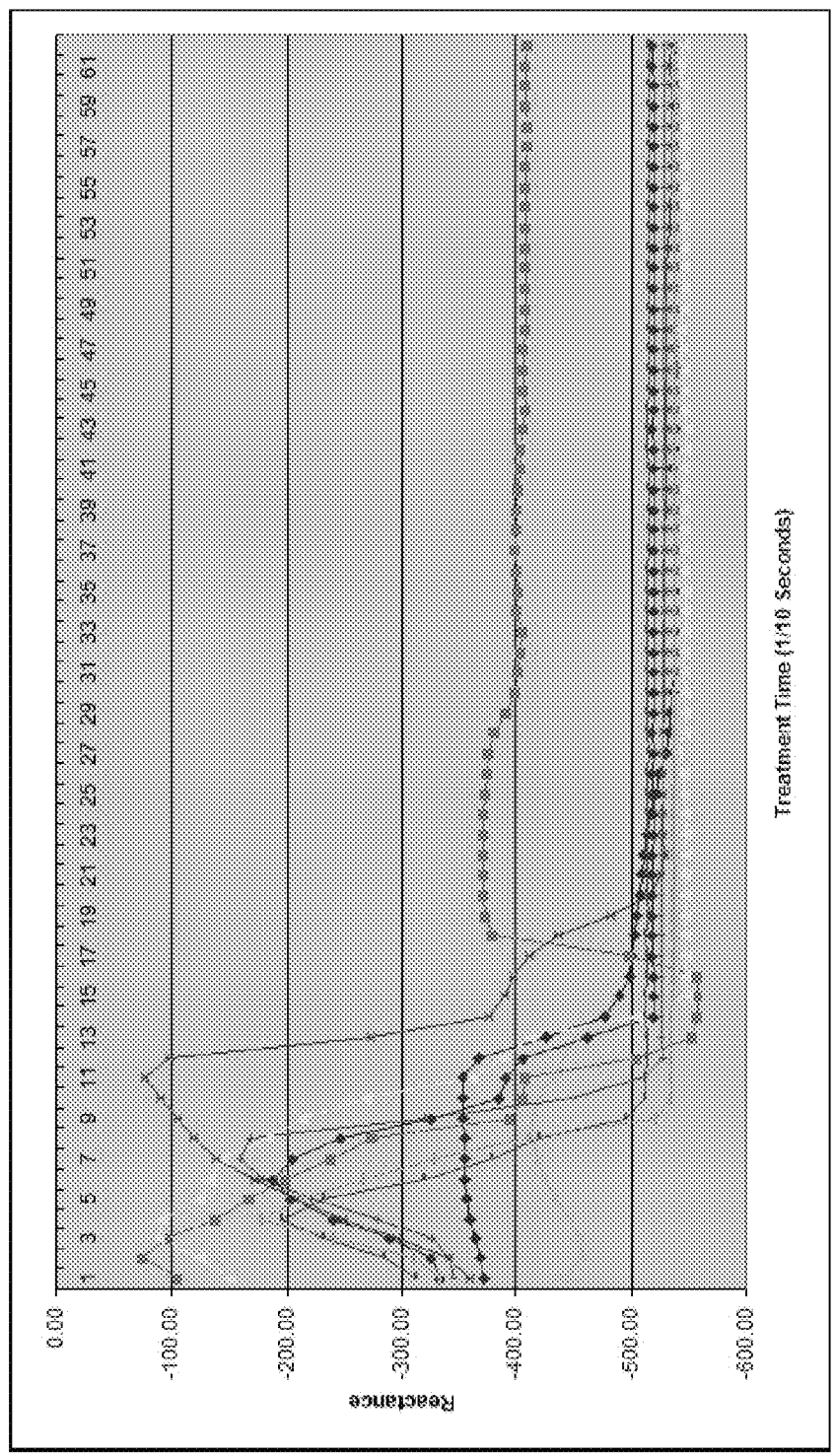
FIGS. 44A-44C illustrate reactance data obtained from the experiments, indicating that the imaginary portion of the circuit impedance can be used to determine when it is appropriate to terminate a treatment.
Figure 44B:
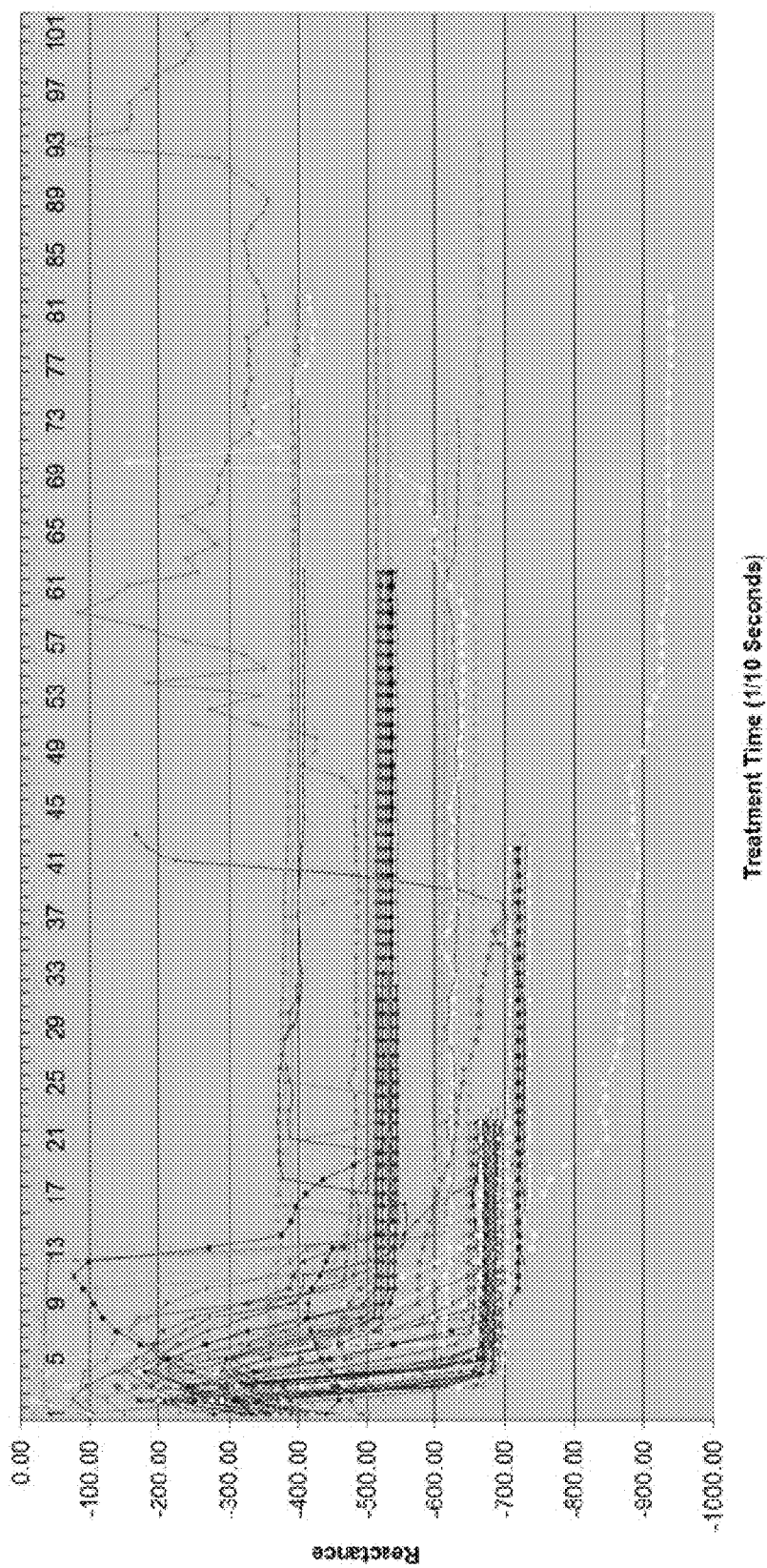
Figure 44C:
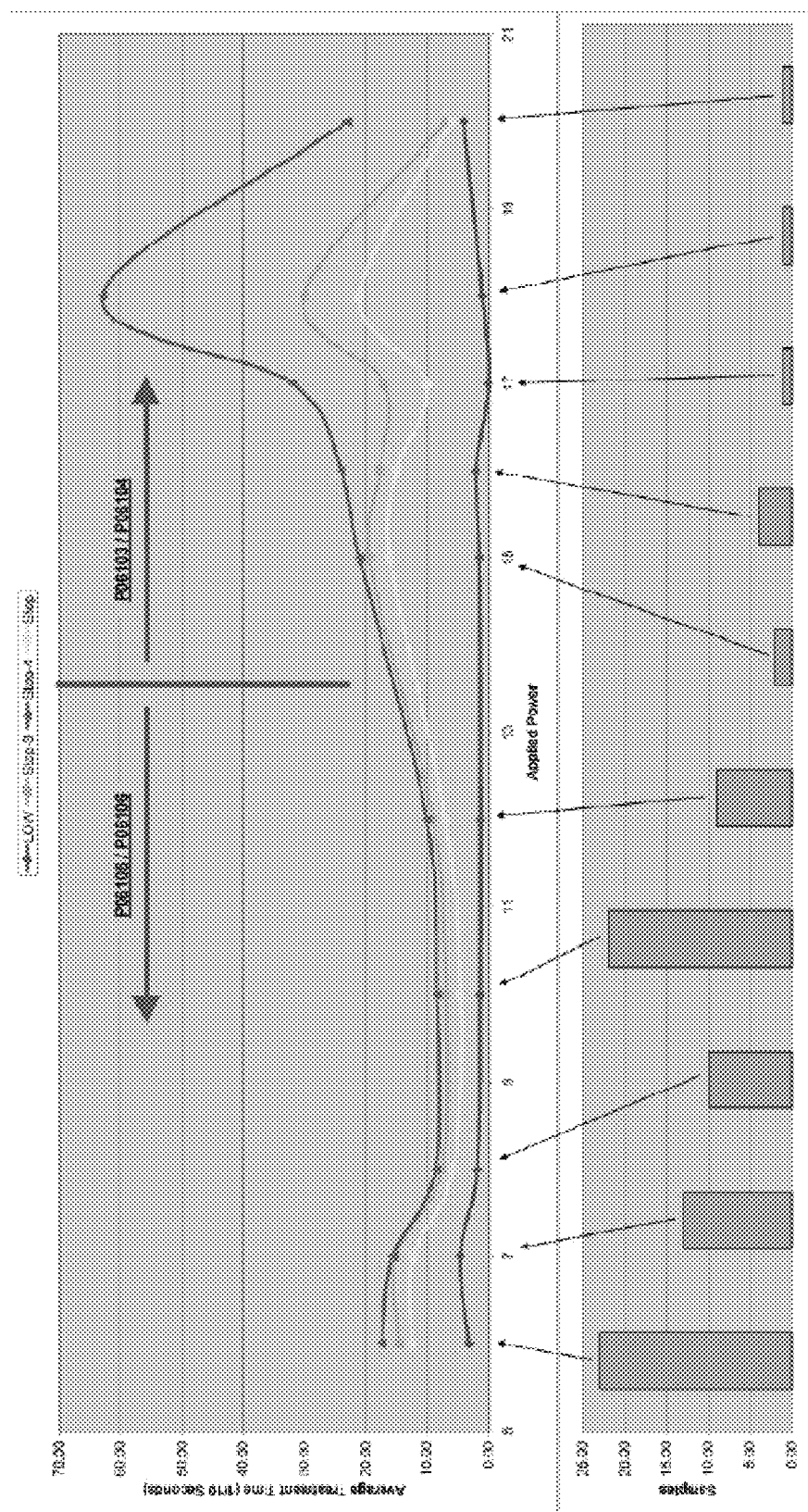

Referring now to FIGS. 44A-44C, relationships between applied power, time, and treatment status of experimental treatments can be better understood. FIG. 44A illustrates reactance versus treatment time for 10 electrodes at a single treatment site. The graph may be representative of typical reactance/time curves for other experiments, and/or that might be generated by some embodiments of clinical treatments using the techniques described herein. Reactance encompasses the imaginary component of impedance, or the resistance of a circuit to AC signals at a certain frequency, and is thereby closely associated with the phase angle. A composite graph showing a plurality of reactance versus time plots from a plurality of different subjects is shown in FIG. 44B. These plots show a sharp change (and particularly an increase in negative reactance) some time after the start of treatment, followed by stabilization of the reactance. The change or increase in negative reactance may represent a lipid phase change and/or shrinkage of tissues induced by RF heating. Hence, when the phase change is complete, the volume of lipids remains constant, resulting in the reactance stabilization.

The plots of FIG. 44A includes sites from test subjects P06103 and p06104 which included induced atherosclerotic disease, and sites or subjects from test subjects P06105 and P06106 which were generally health and free of such tissue. The diseased tissue was generally treated with higher power ranges from about 15 to about 20 Watts, while the healthy tissue was generally treated with lower power ranges from about 6 to about 12 Watts. These different tissue types generated different treatment reactance cycle profiles, as illustrated in FIG. 44C.

44C is a plot of applied power versus average treatment time (in the top portion of the graph), with the number of samples in time averaging shown in the bottom portion of the graph. Each curve (with its associated data points) on the graph represents a readily identifiable point or time in the treatment cycles, as follows: Blue (identified as "LOW" on the graph and generally found at the bottom of the graph) represents the lowest negative value on the reactance curve of FIG. 44B; Yellow (identified as "Stop") represents a transition during each treatment from a negative slope to a zero slope on the reactance curve; Orange (identified as "Stop 3") represents the point along the reactance curve, after the Yellow or Stop point, where two sets of consecutive reactance readings are within a threshold value so as to indicate stabilization; and Red (identified as "Stop 4") represents the point after the Yellow or Stop point where three sets of consecutive readings differ by less than the threshold.

FIG. 44C indicates identifiably different trends in the reactance treatment cycles between healthy and diseased tissue, and/or between the upper and lower bounds of healthy and diseased tissues. Healthy tissue may exhibit a decreasing trend whereas diseased tissue may show an increasing trend. This difference may be due to the increased volume of lipids that are being exposed to the energy when higher powers are used. These larger volumes of lipids may absorb more energy during the phase change process, and this may explain any increased treatment times for higher powers in diseased tissue.

Monitoring the tissue reactance and/or phase angle during treatment may be a viable indicator for an appropriate end of treatment, allowing treatment to the target diseased tissue to be terminated while inhibiting injury to collateral tissues. This data also indicates that appropriate heating times may be less than 10 seconds, being less than 5 seconds, and ideally being from about 0.5 seconds to about 3 seconds in many embodiments.

Figure 45A:
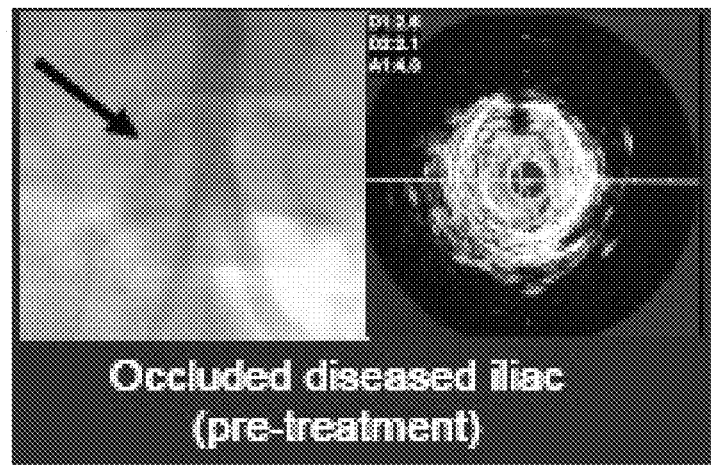
FIGS. 45A and 45B illustrate experimental test results, showing how an occluded vascular site (FIG. 45A) was durably increased size.
Figure 45B:
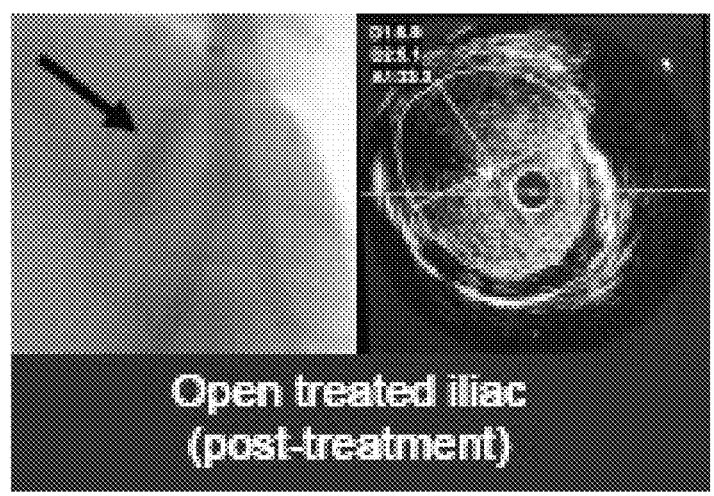

Referring now to FIGS. 45A and 45B, experimental test results show how an occluded vascular site (FIG. 45A, having an initial area of about 4 mm$^2$) was durably increased in size (FIG. 45B, to about 23 mm$^2$). These are exemplary results, based on experiments using about 60 sites in 13 pig iliac arteries, with the study extending from 7 to 90 days post treatment. FIGS. 45A and 45B demonstrate these results using angiographic and IVUS imaging.

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

What is claimed is:

1. A method for characterizing and treating a target tissue in a patient body, the method comprising:
    engaging a vessel wall with a plurality of electrodes by expanding a radially expandable structure disposed near a distal end of a catheter body within a blood vessel, the plurality of electrodes being circumferentially distributed about the radially expandable structure, wherein the radially expandable structure comprises a balloon and the plurality of electrodes comprise a plurality of flex circuits mounted on the balloon;
    energizing a circuit with a tissue characterizing energy, the circuit comprising the plurality of electrodes engaged against the vessel wall, the target tissue and a collateral tissue;
    characterizing the target tissue and the collateral tissue by measuring a phase angle of the circuit while the circuit is energized with the tissue characterizing energy;
    determining an appropriate treatment energy from the measured phase angle of the circuit; and
    energizing the circuit comprising both the target tissue and the collateral tissue with the appropriate treatment energy so that the treatment energy heats the target tissue to a target tissue treatment temperature and heats the collateral tissue to a collateral tissue temperature that is lower than the target tissue treatment temperature,
    wherein the target tissue of the circuit, if heated by energizing the circuit with a standard RF energy so as to heat the target to the target tissue treatment temperature, would result in the collateral tissue of the circuit being heated to a standard RF collateral tissue temperature that is higher than the collateral tissue temperature.

2. The method of claim 1, wherein determining the appropriate treatment energy comprises determining a treatment phase angle so as to compensate for the measured phase angle.

3. The method of claim 1, wherein the tissue characterizing energy comprises a plurality of frequencies, and wherein:
    for each of the plurality of frequencies:
    the collateral tissue of the circuit has an associated impedance magnitude and an associated phase angle; and
    the target tissue of the circuit has an associated impedance magnitude and an associated phase angle; and
    wherein the appropriate treatment energy is determined by determining a treatment frequency at which the associated target tissue phase angle differs sufficiently from the associated phase angle of the collateral tissue.

4. The method of claim 3, wherein the target tissue is characterized by applying a plurality of tissue characterizing energies of differing frequencies to measure a plurality of associated phase angles of the circuit.

5. The method of claim 1, wherein the target tissue treatment energy heats the target tissue to a treatment temperature at least 2° C. greater than a treatment temperature of the collateral tissue.

6. The method of claim 1, wherein the target tissue treatment energy heats the target tissue to the target tissue treatment temperature and heats the collateral tissue to the collateral tissue temperature, which is lower than the standard RF collateral tissue treatment temperature.

7. The method of claim 1, wherein the plurality of electrodes comprises an array of electrodes having selectively energizable electrode subsets, each subset comprising a single electrode or adjacent pair of electrodes, and wherein the circuit is:
energized with the treatment energy by sequentially energizing the subsets of the array of electrodes,
energized with the tissue characterizing energy by sequentially energizing the subset of the plurality of electrodes, or
energized with each of the treatment energy and the tissue characterizing energy by sequentially energizing the subset of the plurality of electrodes.

8. The method of claim 1, wherein the target tissue has an eccentric thickness about an axis of a body lumen, and wherein the circuit is energized with an eccentric energy in response to the thickness.

9. The method of claim 1, wherein the plurality of electrodes comprise an electrode array having axially offset electrodes.

10. The method of claim 1, wherein each of the plurality of flex circuits comprise bi-polar electrode pairs.

11. A method for characterizing and treating a target tissue in a patient body, the method comprising:
engaging a plurality of electrodes against a vessel wall of a blood vessel of the patient by expanding a radially expandable structure disposed near a distal end of a catheter, the plurality of electrodes circumferentially distributed about the radially expandable structure disposed near a distal end of a catheter body, so that the engaged plurality of electrodes define a plurality of separate circuits, each circuit of the plurality of circuits including a collateral tissue and the target tissue, wherein the radially expandable structure comprises a balloon and the plurality of electrodes comprise a plurality of flex circuits mounted on the balloon;
energizing a circuit of the plurality of circuits with a tissue characterizing energy, the circuit comprising selected electrodes of the plurality of electrodes, the target tissue and the collateral tissue;
characterizing the target tissue by monitoring an electrical characteristic of the circuit;
determining an appropriate treatment energy from the characterizing of the target tissue; and
energizing the circuit comprising both the target tissue and the collateral tissue with the appropriate treatment energy so that the treatment energy heats the target tissue to a target tissue treatment temperature and heats the collateral tissue to a collateral tissue temperature that is lower than the target tissue treatment temperature,
wherein the target tissue of the circuit, if heated by energizing the circuit with a standard RF energy so as to heat the target to the target tissue treatment temperature, would result in the collateral tissue of the circuit being heated to a standard RF collateral tissue temperature that is higher than the collateral tissue temperature.

12. The method of claim 11, further comprising halting the energizing of the circuit in response to a change in the electrical characteristic of the circuit.

13. The method of claim 11, wherein characterizing the target tissue includes measuring a phase angle of the circuit while the circuit is energized so as to generate a signature profile for the target tissue.

14. The method of claim 13, wherein the signature profile may be used to distinguish between healthy tissue, plaque, partially treated tissue and fully treated tissue.

15. The method of claim 11, wherein the tissue characterizing energy comprises a plurality of frequencies, and wherein:
for each of the plurality of frequencies:
the collateral tissue of the circuit has an associated impedance magnitude and an associated phase angle; and
the target tissue of the circuit has an associated impedance magnitude and an associated phase angle; and
wherein the appropriate treatment energy is determined by determining a treatment frequency at which the associated target tissue phase angle differs sufficiently from the associated phase angle of the collateral tissue.

16. The method of claim 11, wherein characterizing the target tissue comprises passing a current of the circuit energized with the tissue characterizing energy to the target tissue through the healthy tissue.

17. The method of claim 11, wherein energizing the circuit with the treatment energy so that the treatment energy heats the target tissue comprises passing a current of the energized circuit to the target tissue through the healthy tissue.

18. The method of claim 11, wherein the plurality of circuits comprise multiple separate circuits.

19. The method of claim 18, wherein the treatment energy is applied to each of the plurality of circuits from electrodes of the plurality of electrodes in contact with the collateral tissue.

20. The method of claim 19, wherein energizing the circuit with the appropriate treatment energy comprises energizing differing pairs of electrodes with RF energy at varying durations separated by resting period of varying duration.

21. The method of claim 11, wherein energizing the circuit with the appropriate treatment energy comprises selectively directing the treatment energy to an eccentric portion along a circumferentially engaged vessel wall, the circuit along the eccentric portion including both the target tissue and the collateral tissue.

22. A method for characterizing and treating a target tissue having both a diseased tissue and a healthy tissue in a patient body, the method comprising:
engaging a plurality of electrodes against the target tissue, the plurality of electrodes being circumferentially distributed about a radially expandable member disposed near a distal end of a catheter body, by expanding the radially expandable member in a body vessel of the patient, wherein the radially expandable structure comprises a balloon and the plurality of electrodes comprise a plurality of flex circuits mounted on the balloon;
forming a plurality of circuits, each circuit comprising selected electrodes, the diseased tissue and the healthy tissue;
energizing each circuit with a tissue characterizing energy;
characterizing the target tissue by measuring a phase angle of each circuit while the circuit is energized with the characterization energy;
determining which of the plurality of circuits includes diseased tissue; and
energizing circuits including diseased tissue with an appropriate treatment energy so that the treatment energy heats the diseased tissue to a diseased tissue treatment temperature and heats the healthy tissue to a healthy tissue temperature that is lower than the diseased tissue treatment temperature,
wherein the diseased tissue of the circuit, if heated by energizing the circuit with a standard RF energy so as to heat the diseased tissue to the diseased tissue treatment temperature, would result in the healthy tissue of the circuit being heated to a standard RF healthy tissue temperature that is higher than the healthy tissue temperature.

23. The method of claim 22, wherein determining the appropriate treatment energy comprises determining a treatment phase angle so as to compensate for the measured phase angle.

24. The method of claim 22, wherein the tissue characterizing energy comprises a plurality of frequencies, and wherein:
   for each of the plurality of frequencies:
   the healthy tissue of the circuit has an associated impedance magnitude and an associated phase angle; and
   the diseased tissue of the circuit has an associated impedance magnitude and an associated phase angle; and
   wherein the appropriate treatment energy is determined by determining a treatment frequency at which the associated diseased tissue phase angle differs sufficiently from the associated phase angle of the healthy tissue.

25. The method of claim 22, wherein characterizing the tissue includes differentiating between diseased tissue and healthy tissue.

26. The method of claim 25, wherein diseased tissue may include calcified plaque, fibrous plaque and lipid-rich plaque.

27. The method of claim 22, wherein characterizing the tissue includes differentiating between tissue that has not been treated or has been partially treated and tissue that has been appropriately treated.

* * * * *